US012810422B2

(12) United States Patent
Bagaméry et al.

(10) Patent No.: US 12,810,422 B2
(45) Date of Patent: Nov. 24, 2026

(54) METHOD FOR TRAINING A SYSTEM ADAPTED FOR AIDING EVALUATION OF A MEDICAL IMAGE

(71) Applicant: Mediso Medical Imaging Systems Kft., Budapest (HU)

(72) Inventors: István Bagaméry, Budapest (HU); Tamás Bükki, Szendehely (HU); Gábor Légrádi, Kesztölc (HU); Ákos Kovács, Budapest (HU)

(73) Assignee: Mediso Medical Imaging Systems KFT, Budapest (HU)

( * ) Notice: Subject to any disclaimer, the term of this patent is extended or adjusted under 35 U.S.C. 154(b) by 177 days.

(21) Appl. No.: 18/865,957

(22) PCT Filed: May 10, 2023

(86) PCT No.: PCT/HU2023/050025
§ 371 (c)(1),
(2) Date: Nov. 14, 2024

(87) PCT Pub. No.: WO2023/223060
PCT Pub. Date: Nov. 23, 2023

(65) Prior Publication Data

US 2025/0308019 A1 Oct. 2, 2025

(30) Foreign Application Priority Data

May 17, 2022 (HU) ..................................... 2200160

(51) Int. Cl.
*G06T 7/00* (2017.01)
*G06T 7/70* (2017.01)
(Continued)

(52) U.S. Cl.
CPC .............. *G06T 7/0012* (2013.01); *G06T 7/70* (2017.01); *G06V 10/30* (2022.01); *G06V 10/764* (2022.01);
(Continued)

(58) Field of Classification Search
CPC .................... G06T 7/0012; G06T 7/70; G06T 2207/20081; G06T 2207/30096;
(Continued)

(56) References Cited

U.S. PATENT DOCUMENTS 7,545,965 B2 6/2009 Suzuki et al.
9,332,953 B2 5/2016 Suzuki
(Continued)

FOREIGN PATENT DOCUMENTS

CN 107784312 A 3/2018
CN 109166161 A 1/2019
(Continued)

OTHER PUBLICATIONS

Uzunova, Hristina, et al. "Unsupervised pathology detection in medical images using conditional variational autoencoders." International journal of computer assisted radiology and surgery 14.3 (2019): 451-461. (Year: 2019).*
(Continued)

*Primary Examiner* — Utpal D Shah
(74) *Attorney, Agent, or Firm* — Wood Herron & Evans LLP

(57) ABSTRACT

The invention is a training method for training a system adapted for aiding evaluation of a medical image, during which a processing unit, an annotator unit, and an auxiliary unit for generating pseudo images are trained by independent pre-trainings. In a first cycle transferring data packets obtained by applying processing and annotator units on pseudo images and lesion location data packets correspond-
(Continued)

ing to pseudo images to ROC unit, AUC parameter is determined. In a further cycle, building an AUC of the first cycle into joint-training loss functions of the processing unit and the annotator unit. The method further comprises training the joint-training functions of the processing unit and the annotator unit. The method further comprises applying the processing unit and the annotator unit on the pseudo images based on the lesion location data packets such that AUC is determined.

16 Claims, 19 Drawing Sheets

(51) Int. Cl.
*G06V 10/30* (2022.01)
*G06V 10/764* (2022.01)
*G06V 10/774* (2022.01)
*G06V 10/776* (2022.01)
*G16H 50/20* (2018.01)

(52) U.S. Cl.
CPC .......... *G06V 10/774* (2022.01); *G06V 10/776* (2022.01); *G16H 50/20* (2018.01); *G06T 2207/20081* (2013.01); *G06T 2207/30096* (2013.01); *G06V 2201/03* (2022.01)

(58) Field of Classification Search
CPC .......... G06T 2207/20084; G06V 10/30; G06V 10/764; G06V 10/774; G06V 10/776; G06V 2201/03; G06V 10/82; G06V 10/00; G16H 50/20; G06N 3/0455; G06N 3/0475; G06N 20/00; A61B 5/00; A61B 5/0013
See application file for complete search history.

(56) References Cited

U.S. PATENT DOCUMENTS

| | | | |
|---|---|---|---|
| 9,730,660 B2 | 8/2017 | Suzuki | |
| 9,953,246 B2 | 4/2018 | Bouchard et al. | |
| 10,032,256 B1 | 7/2018 | Anaya et al. | |
| 10,445,879 B1 | 10/2019 | Fuchs et al. | |
| 10,722,180 B2 | 7/2020 | Zhang et al. | |
| 2009/0327176 A1 | 12/2009 | Teramoto | |
| 2011/0280457 A1 | 11/2011 | Nielsen et al. | |
| 2013/0051516 A1 | 2/2013 | Yang et al. | |
| 2018/0018757 A1 | 1/2018 | Suzuki | |
| 2018/0082443 A1 | 3/2018 | Risman et al. | |
| 2018/0240219 A1 | 8/2018 | Mentl et al. | |
| 2018/0286038 A1 | 10/2018 | Jalali et al. | |
| 2019/0035118 A1 | 1/2019 | Zhao et al. | |
| 2019/0073569 A1 | 3/2019 | Ben-Ari et al. | |
| 2019/0108634 A1 | 4/2019 | Zaharchuk et al. | |
| 2019/0156524 A1 | 5/2019 | Park et al. | |
| 2019/0340752 A1 | 11/2019 | Brestel et al. | |
| 2019/0365341 A1 | 12/2019 | Chan et al. | |
| 2020/0043204 A1 | 2/2020 | Fu et al. | |
| 2020/0065940 A1 | 2/2020 | Tang et al. | |
| 2020/0074234 A1 | 3/2020 | Tong et al. | |
| 2020/0175397 A1* | 6/2020 | Wang | G06F 16/285 |
| 2021/0312227 A1* | 10/2021 | Moradiannejad | G06F 18/214 |
| 2025/0292407 A1* | 9/2025 | Nketiah | G06T 7/0014 |
| 2026/0120864 A1* | 4/2026 | Ocampo | G06N 3/08 |
| 2026/0187984 A1* | 7/2026 | Chen | G06V 10/774 |

FOREIGN PATENT DOCUMENTS

| | | | |
|---|---|---|---|
| EP | 3367329 A1 | 8/2018 |
| EP | 3576020 A1 | 12/2019 |
| WO | 2016/033458 A1 | 3/2016 |
| WO | 2018/200493 A1 | 11/2018 |

OTHER PUBLICATIONS

Chen, Xiaoran, and Ender Konukoglu. “Unsupervised detection of lesions in brain MRI using constrained adversarial auto-encoders.” arXiv preprint arXiv:1806.04972 (2018). (Year: 2018).*

Chao Gou et al: “Parallel Medical Imaging: A New Data-Knowledge-Driven Evolutionary Framework for Medical Image Analysis”, arxiv.org, Cornell University Library, Mar. 12, 2019.

G. Litjens et al., A survey on deep learning in medical image analysis, Medical Image Analysis 42, pp. 60-88 (2017).

Lovedeep Gondara, Medical image denoising using convolutional denoising autoencoders, arXiv:1608.04667v1, Aug. 16, 2016.

Aggarwal, C. C.: Neural Networks and Deep Learning. Chaco: Springer, p. 357 (2018).

John A. Swets, ROC Analysis Applied to the Evaluation of Medical Imaging Techniques, Investigative Radiology, vol. 14, p. 109, (1979).

J. Lehtinen et al., Noise2Noise: Learning Image Restoration without Clean Data, (2018).

S. Soltanayev et al, Training and Refining Deep Learning Based Denoisers without Ground Truth Data (2019).

P. Rajpurkar, Cardiologist-Level Arrhythmia Detection with Convolutional Neural Networks, (2017).

A.Y. Hannun et al, Cardiologist-level arrhythmia detection and classification in ambulatory electrocardiograms using a deep neural network, Nature Medicine 25, 65-69 (2019).

PCT/HU2023/050025 International Search Report Sep. 11, 2023.

PCT/HU2023/050025 Written Opinion Sep. 11, 2023.

* cited by examiner

950

945

960

962

964

966

968

970

METHOD FOR TRAINING A SYSTEM ADAPTED FOR AIDING EVALUATION OF A MEDICAL IMAGE

This application claims priority, as a national phase application under 35 U.S.C. § 119 and/or 35 U.S.C. § 120, to PCT Application No. PCT/HU2023/050023, filed May 10, 2023, which claims priority to Hungarian Application No. P2200160, filed May 17, 2022, each of which is expressly incorporated by reference herein, in its entirety.

TECHNICAL FIELD

The invention relates to a training method for training a system adapted for aiding evaluation of an input medical image, to a system trained by means of the method, and to a configuration method adapted for configuring the system.

BACKGROUND ART

Neural networks (for short: NN-s) are widely used in the field of medical imaging and image evaluation. An overview is provided for example by the study of G. Litjens et al., *A survey on deep learning in medical image analysis*, Medical Image Analysis 42, 60-88 (2017).

Neural networks applied in the field of noise filtering operate typically (but not exclusively) as autoencoders (on the construction of convolution autoencoder networks see: https://towardsdatascience.com/auto-encoder-what-is-it-and-what-is-it-used-for-part-1-3e5c6f017726; Lovedeep Gondara, *Medical image denoising using convolutional denoising autoencoders*, arXiv: 1608.04667v1, 16 Aug. 2016; Aggarwal, C. C.: *Neural Networks and Deep Learning*. Cham: Springer, page 357 (2018).), which involves multiple rounds of resampling the input image to lower resolutions. Based on the images received during the training process, neural networks learn characteristic structures and patterns, for example in the case of planar bone images the ribs, vertebrae, pelvic bone, and characteristic patterns of accumulations and structural patterns.

During the filtering process the autoencoder network synthesises images from the learned patterns, finally resizing the images to their original resolution, thereby restoring filtered images with a contrast that is similar or better than the original and thus significantly improving the signal-to-noise ratio. Therefore, unlike in the case of low-pass or band-pass filters operating in the "conventional" frequency space, noise filtering is not carried out by reducing high-frequency components.

Known technical approaches in the field of convolutional neural noise filtering (and other quality improvement) are disclosed in the following documents: US 2019/0035118 A1, US 2018/0240219 A1; EP 3 367 329 A1; US 2019/0108634 A1; WO 2018/200493 A1; U.S. Pat. No. 9,730,660 B2; US 2013/0051516 A1; U.S. Pat. No. 9,332,953 B2; U.S. Pat. No. 7,545,965 B2; CN 109166161 A; U.S. Pat. No. 10,032,256 B1; US 2020/0065940 A1; US 2020/0074234 A1; WO 2016/033458 A1; U.S. Pat. No. 9,953,246 B2; while the documents related to filtering reconstructed volumes are: US 2019/0156524 A1, US 2019/0035118 A1 (this document can be included also here beside above); US 2020/0043204 A1; US 2019/0365341 A1 and US 2018/0018757 A1.

Image filters based on neural networks enhance (pick up, separate) the structures from the noise, thereby significantly improving the signal-to-noise ratio of the images. In the case of planar, for example bone scintigraphy investigations it can be observed on the basis of feedback received from physicians experienced in medical records that makes medical record making (keeping) much easier utilising images filtered by such networks, because the lesions (for example, abnormal accumulations; we often use in the description the accumulations as examples, but these findings can usually be generalised to any type of structural difference (deviation); in necessary cases it can also be determined from the context that they are normal or abnormal accumulations) can be localised easier anatomically, even in lack of a CT. In addition to that, it seems that by the help of these a significant reduction of the activity injected to the patient and of measurement time can be made.

The trained neural network picks out supposed structures from the noise based on the images it "saw" during the training (training process). Although the filtered images have low noise and are of enhanced contrast, there is a danger that the NN-based filter removes certain abnormal accumulations (this is the so-called "false negative" diagnosis), or introduces abnormal accumulations, for example generates false bone metastases from the noise (this is the so-called "false positive" diagnosis). Because of that, the filtered image processed for the physician making medical record is not in itself sufficient for assuring the clinical/diagnostic value of the method. Similarly, the filtered image in itself does not allow such an adjustment of the algorithm that can demonstrably improve the diagnostic value, or that can allow for determining to how much the proportion of activity and measurement time can be lowered to still preserve the diagnostic value of the examination.

A known method for examining the diagnostic value of medical images is ROC analysis (ROC curve: receiver operation characteristic curve, see for example: John A. Swets, *ROC Analysis Applied to the Evaluation of Medical Imaging Techniques, Investigative Radiology*, vol 14, p 109, (1979)), which shows that it is not possible to characterise a medical imaging method (or other medical diagnostic test) by assessing only a single characteristic diagnostic parameter, e.g. the true positive rate or the false positive rate.

In US 2011/0280457 A1 and U.S. Pat. No. 10,445,879 B1 medical applications are disclosed wherein the ROC analysis is applied for evaluating and comparing results, for example for evaluating the performance of different models. Similar approaches are disclosed in US 2018/0082443 A1, US 2019/0340752 A1 and U.S. Pat. No. 10,722,180 B2.

For example, in ROC analysis the characteristic curve of the imaging is plotted in connection with the true positive rate, i.e., the sensitivity, and the false positive rate (1−specificity, that is, the specificity value subtracted from unity), cf. FIG. 6. Sensitivity is the probability of the positive outcome of a diagnostic test for a patient who has the disease (its formula is: TP/(TP+FN)). Specificity is the probability of the negative outcome of a diagnostic test for a patient without the disease (its formula is: TN/(TN+FP); according to the notations in the formulas TP: true positive, FN: false negative, TN: true negative, FP: false positive). Each test characterised this way has a corresponding operating point (workpoint) which determines the sensitivity-specificity pair applied in the given test or method.

In US 2019/0073569 A1 a neural network-based approach for classifying medical images, particularly mammograms is disclosed for weakly labelled and imbalanced data sets. In the document two partial networks (a scanning network and a classification network) are applied which can also be implemented applying a common network. The "scanning network" is adapted for determining the arrangement (layout) of features in the image, while the "classification network" determines (typically for the entire image) if the image contains a difference (deviation) of a given type. The application of the AUC ("area under the ROC curve") parameter for classification is disclosed for correcting problems caused by unbalanced data. In other fields, the AUC parameter is utilised in a similar way in case of unbalanced data in CN 107784312 A and US 2009/0327176 A1.

In US 2018/0286038 A1 a neural network-based machine learning approach is disclosed that is adapted for the label-free ("unsupervised") classification of cells. In this approach, the training is aimed at maximising the area under the ROC curve (AUC) by feeding back the AUC parameter to a given level of the neural network that is responsible for classification (see FIG. 5 and paragraph [0077] of the document, where it is spelled out that the training process utilising the AUC parameter cooperates with the decision making layer).

In accordance with the application frameworks, in US 2018/0286038 A1 the ROC is the indicator of the performance of the classification module. Because the AUC gradient is not well-behaved, according to the application framework a genetic algorithm is applied for the supervised learning of the entire system, which is able to find the local extrema of the typically multidimensional configuration space even in case the applied cost function is discontinuous, noisy, and contains a large number of difficult-to-be-discovered local extrema. Similarly, in US 2020/0175397 A1 the result of the ROC/AUC test is utilised for improving classification accuracy.

Currently, the training of neural network-based image processing systems typically requires thousands of images. In the known approaches, in case this training database is modified, is complemented, or the parameters of the scanning camera, the medical scanning protocol or the parameters of the neural network are changed, then naturally the clinical evaluation of the imaging/image processing device must also be redone, otherwise the clinical value of the readjusted, reconfigured, improved system cannot be assured.

According to the known approaches, this repeated verification requires significant medical resources each time it has to be carried out. These factors drastically increase the development costs and the costs related to the continuous quality assurance of such diagnostically valuable, artificial intelligence-containing (e.g. NN-based software) systems (FDA: *Artificial Intelligence and Machine Learning in Software as a Medical Device*, https://www.fda.gov/medical-devices/software-medical-device-samd/artificial-intelligence-and-machine-learning-software-medical-device), to an extent that within the known approaches the production of software possessing assured clinical value is rendered practically impossible.

In relation to these known approaches another problem area arises, namely that for producing the filtered images (or, in general, images transformed applying any type of image transformation process) relevant from the aspect of diagnostic value a so-called "ground truth" should be determined, i.e. that what is the truth, a starting base: i.e. whether there can be found a different (having deviation) from normal accumulation/structure (generally: lesion) at the location where there is such a structure shown by the filtered image that may have earlier been masked by noise, or whether the filter (or the image processing system) has possibly removed such entities. Statistical evaluation and a correctly performed ROC analysis would also require the same information, which according to the medical consensus can be assuredly provided only by histopathological examination.

However, it has been proven that it is possible to design a neural network that is able to learn effectively even in case this "ground truth" is not available, or it is noisy, i.e., is not known assuredly (J. Lehtinen et al., *Noise2Noise: Learning Image Restoration without Clean Data*, (2018), arXiv: 1803.04189v3 29 Oct. 2018; S. Soltanayev et al, *Training and Refining Deep Learning Based Denoisers without Ground Truth Data* (2019), arXiv: 1803.01314v4, 22 Apr. 2021).

In order to increase the performance of the neural network in such a case to a level similar to the performance (error rate) of an average physician, it is for example required that the consensual expert opinion of several physicians be obtained for at least the images applied for verification.

An example is known where the diagnostic value of a neural network trained in such a way is able to surpass the diagnostic performance of an average physician (P. Rajpurkar, *Cardiologist-Level Arrhythmia Detection with Convolutional Neural Networks*, (2017), arXiv: 1707.01836v1, 6 Jul. 2017; and A. Y. Hannun et al, *Cardiologist-level arrhythmia detection and classification in ambulatory electrocardiograms using a deep neural network*, Nature Medicine 25, 65-69 (2019)).

However, this may further increase the training, tuning and clinical verification costs in case we stick to an assured diagnostic value, because each image (at least the images of the test database) would have to be individually examined by a group made up of several physicians who would have to mark and classify the differences and suspected accumulations. Moreover, the costly medical verification procedure would have to be repeated each time the recording protocol is modified (new collimator, isotope or ligand, modified measurement time or injected activity), and also for a different patient population.

According to the application in nuclear medicine, it is also a problem that the intrinsic variability of widely used methods is not known. Or, to put it in another way, in the known approaches it cannot be safely determined if the different results obtained from two subsequent measurements can be explained by methodological limitations or by a change in the patient's state.

In view of the known approaches, there is a need for a system adapted for aiding the evaluation of medical images that performs its tasks more effectively compared to the existing solutions.

DESCRIPTION OF THE INVENTION

The primary object of the invention is to provide a system for aiding the evaluation of a medical image and a training method for training the system, which are free of disadvantages of prior art approaches to the greatest possible extent.

The object of the invention is that by providing a system for aiding the evaluation of medical images a reliable (safe), clinically verified solution can be made available to physicians making medical record (i.e., to have a tool with such functionality) that aids them in making the medical recording more reliable, easier and more transparent, such that a responsible diagnosis of the patient can be made more quickly and with improved reliability.

The objects of the invention can be achieved by providing the training method according to claim 1, the system according to claim 12, and the configuration method according to claim 16. Preferred embodiments of the invention are defined in the dependent claims.

The invention provides a solution for the challenges described in the introduction. With the help of the training method according to the invention, the system according to the invention makes it possible to provide physicians making medical record with a reliable, clinically verified solution that helps them make a diagnosis more quickly and more reliably (i.e., in general, it helps evaluation).

Thus, the system according to the invention—by applying machine learning, preferably neural networks for image processing—only aids in making the diagnosis (by marking the accumulations, or more generally, structural differences that are suspect). Accordingly, the system according to the invention is a "medical diagnosis aiding" system—or more generally, a system adapted to aid clinical evaluation—and thus provides results of this type (in other words, it falls to the field of CAD, i.e. computer aided diagnostic tools). To put it in another way, as it is spelled out in detail below, the system is adapted to discover the accumulations/differences (generally: lesions) that different from normal, and leaves it to the physician making medical record to make the diagnosis. It thereby becomes a tool that aids (rather than replaces) the physician.

Extremely preferably, the system according to the invention allows that the clinical value of the system can be assured during the development and the service life (utilisation) of the product in a cost-effective manner. Preferably, it also allows for determining the diagnostic variability of a given examination, and knowing of the error of repeatability, thereby enables to accurately track the state of the patient.

The system according to the invention preferably also allows that a medically verified state of the system can be maintained automatically also in the case of changing the examination protocol or the patient population, without incurring significant additional costs.

The system according to the invention preferably also allows the evaluation of the chosen therapeutic pathways in general, and in particular, i.e., with regard to the given patient, thereby allowing, with the help of the results provided by the system (applying a CAD-"computer aided diagnosis"-approach) the treating physician to choose the most effective therapeutic pathway for the patient.

According to the inventive idea, a system adapted to provide a solution to the issues described above is provided by the cooperation of multiple machine learning units (for example such units implemented by neural networks, or for short, neural networks), i.e., their sequential and joint training, which system is able to assure the clinical diagnostic value of the imaging apparatus and of the images processed by it.

The invention can be applied in all fields of medical diagnostic imaging, i.e., for example for planar images recorded with gamma cameras (e.g. bone scintigraphy), images recorded by SPECT (Single Photon Emission Computed Tomography, cross-sectional imaging) and PET (positron emission tomography) imaging, as well as for images recorded applying CT (computer tomography) and MRI (magnetic resonance investigation), and images produced applying optical and ultrasonic medical imaging methods. Accordingly, the applicability of the invention is independent from the imaging modality, i.e., the invention—starting, typically, from the training method—can be applied with all imaging modalities.

Hereinafter, the solution according to the invention will be described typically in relation to images recorded by gamma camera and SPECT imaging; also returning later on to the possibilities for generalisation. All such features that can be possibly applied for every modality and can be considered as generic features from the aspect of the invention are meant to be—modality- and application-independent—generic features, even if they are described in relation to a given modality, application, or specific feature.

During an imaging process applying gamma cameras, the gamma radiation emitted from the patient's body is detected typically by means of a collimator device and a gamma detector, thereby mapping the distribution of the activity that was injected into the patient and is bound to tissue structures; such is for example planar bone scintigraphy (in relation to which illustrative results are detailed below). If the gamma camera is rotated around the patient, such projectional images can be recorded from multiple directions, and can be applied for reconstructing the 3D distribution of the activity inside the patient. This latter technique is called SPECT imaging.

The projectional images gathered during planar and SPECT scans are burdened with significant noise. The less activity is injected into the patient and the shorter the scanning time, the more significant the noise. The same can be stated for PET imaging. In case of CT, measurement noise increases with reducing the radiation load on the patient, i.e., the emitted power of the X-ray source. In case of MRI, the noise increases with increasing imaging speed, i.e., with the reduction of scanning time.

Elevated noise levels increase the probability of the physician making medical record believes that the noise is an abnormal accumulation or difference (this is a so-called "false positive" diagnosis), and noise also makes the detection of small-size accumulations/differences uncertain. However, for reducing the radiation load on the patient (in case of gamma camera/SPECT/PET/CT), and for reducing scan time and for providing better exploitability of the scanning apparatus it is an important goal to reduce the activity to be injected into the patient (gamma camera/SPECT/PET), as well as the radiated power (CT) and thus the dose received by the patient, as well as the measurement time. A solution is given for this by the processing (typically in some sense, noise filtering and/or essence enhancing function, see below) according to the invention of the gathered projectional images, of the measured raw data, and of the 3D volumes generated during the image reconstruction process.

BRIEF DESCRIPTION OF THE DRAWINGS

Exemplary preferred embodiments of the invention are described below with reference to the following drawings, where.

MODES FOR CARRYING OUT THE INVENTION

The invention relates to a training method for training a system adapted for aiding evaluation of an input medical image (the invention also relates to embodiments of the system, see below), wherein the system comprises

Figure 3A:
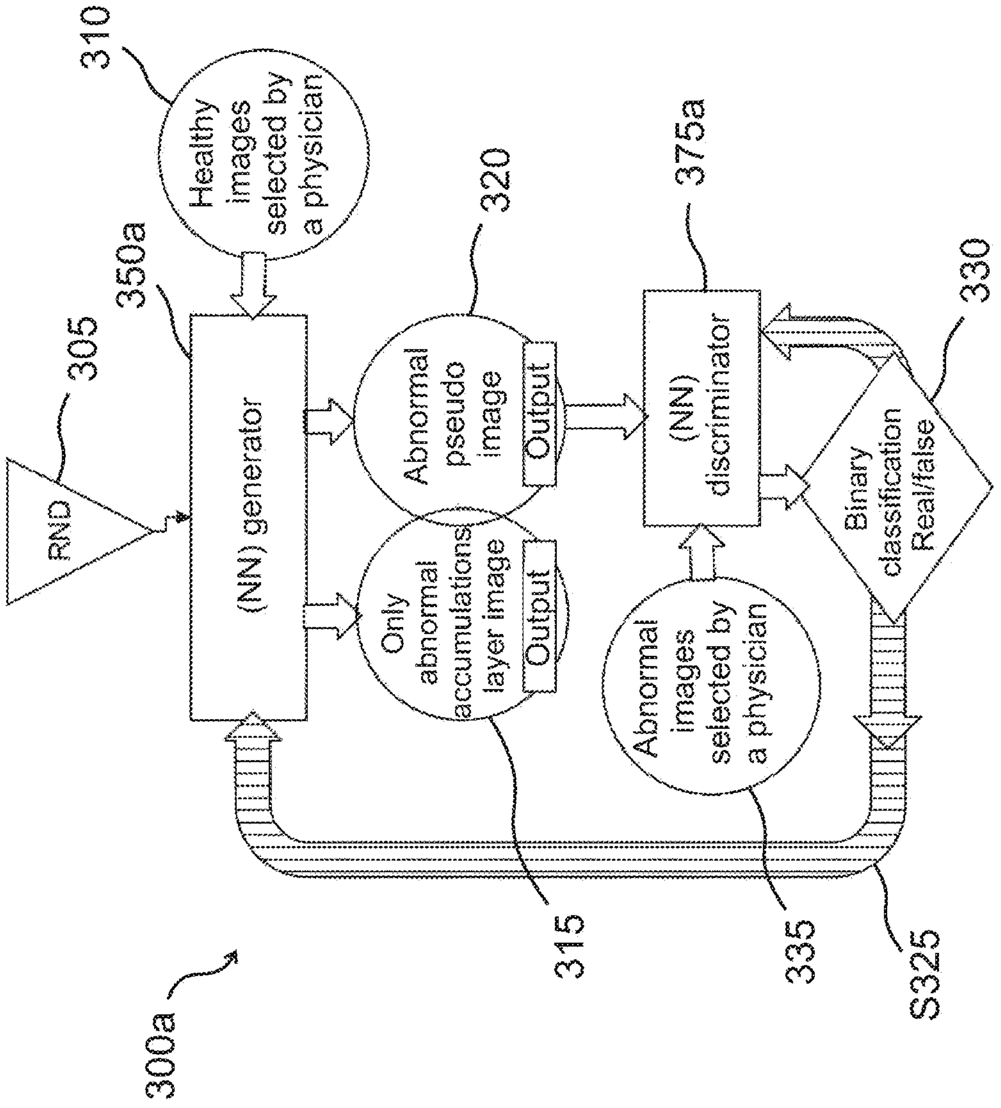
FIG. 3A is a flow diagram illustrating the training of an auxiliary unit in a first embodiment of the method according to the invention.
Figure 3B:
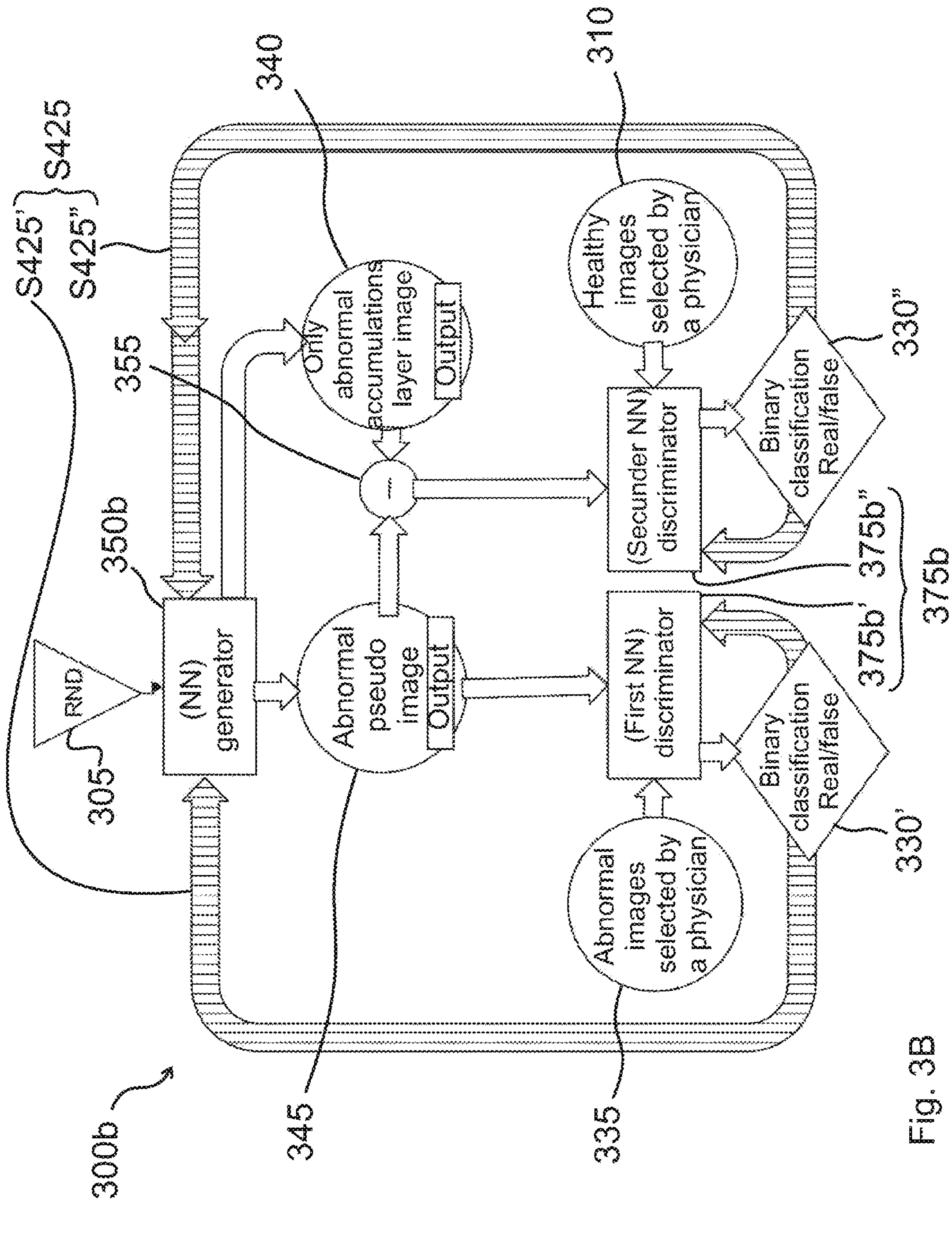
FIG. 3B is a flow diagram illustrating the training of an auxiliary unit in a second embodiment of the method according to the invention.
Figure 5:
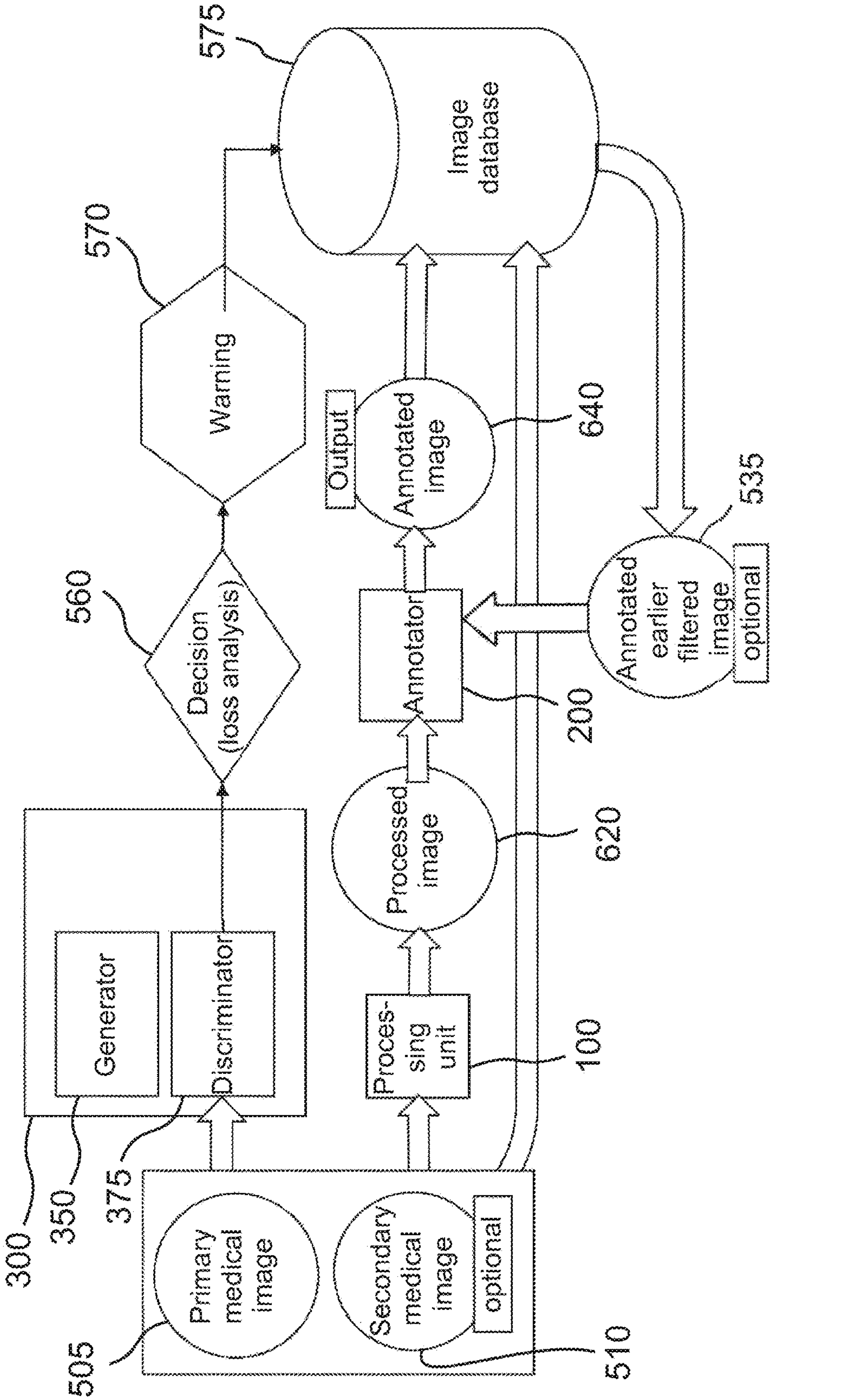
FIG. 5 is a flow diagram illustrating the operation of the system according to the invention in an embodiment trained by the training method.

- a processing unit (module; in an embodiment, a processing unit 100, see FIG. 1, in connection with that the embodiment is described in detail below) based on machine learning (or, for short-together with similar units-machine-learning processing unit) adapted for generating a processed image from an input medical image, and
- an auxiliary unit having a discriminator subunit (submodule) based on machine learning, adapted for determining a discriminability result by subjecting the input medical image to a discriminability test (in an embodiment, an auxiliary unit 300; for its other illustrated embodiments see FIGS. 3A-3B, in relation to which the embodiments will be described in detail below; such a system is trained that has a discriminator subunit adapted for supplying a discriminability result based on a discriminability test, in relation to which see the description of the system and FIG. 5).

The system according to the invention is therefore adapted for aiding evaluation of a medical image; it could also be termed a system for aiding the evaluation of a medical image. In relation to aiding evaluation, reference is made to the description of CAD systems included above, according to which the system aids (helps) the evaluation, i.e., adapted for supplying information contributing to the evaluation (by means of the processing unit or by the annotator unit).

The processing unit is therefore adapted for generating a processed image from an (input) medical image, and, as it will be described below, may perform various processing tasks. The input medical image applied as the input is a medical image generated by medical imaging (in other words, by a medical imaging system, apparatus, or device). The adjective "medical" is included in its name in order to refer to medical imaging.

However, according to that the processing unit is based on machine learning, processing "introduces" artificial intelligence into the processed image, i.e., processing is performed in an "intelligent (smart)" (trained) manner in accordance with the goal set before it, i.e., such that the content of the input image is modified, enhanced in accordance with a specific aspect. In accordance with the joint training (see below), the AUC parameter also reacts, i.e., the effectiveness of the processing unit in performing its tasks can be verified.

In other words, certain image features are "picked up" (enhanced) by the processing unit (in many cases by applying noise filtering or noise reduction in the general sense of the term), such that the structural features that are diagnostically important from the aspect of evaluation are discriminated (differentiated) more, i.e., it performs a kind of essence enhancing (emphasizing); it is adapted for improving (increasing) the signal-to-noise ratio.

In the course of the training method according to the invention

- such an auxiliary unit is applied which has a generator subunit (see e.g. generator subunits 350, 350*a*, 350*b* below in the embodiments of FIGS. 3A-3B; in this case therefore the auxiliary unit also has a generator subunit in addition to the discriminator subunit) based on machine learning, adapted for generating
  - auxiliary pseudo images (see e.g. auxiliary pseudo image 515 in FIG. 4)
  - and first lesion location data packets corresponding to each, respectively, and determining location of one or more lesion possibly present in the auxiliary pseudo images (an exemplary visual representation of such a data packet is an auxiliary lesion image 517 shown in FIG. 4; it can also be said that they are pseudo images possibly comprising at least one lesion, and first lesion location data packets corresponding to the respective pseudo images and determining the location of one or more lesion possibly present in the respective pseudo images), and
- is, furthermore, applied
  - an annotator unit based on machine learning, adapted for identifying a lesion and for generating an annotation result dataset comprising a second lesion location data packet determining location of the one or more lesion possibly identified (in an embodiment see in FIG. 2, in relation to which the embodiment is described in detail below, see also an annotator unit 200 in FIG. 5), and
  - and a ROC unit adapted for determining an AUC parameter characteristic of a diagnostic value (in an embodiment, see an ROC unit 500 in FIG. 4).

The annotator unit is adapted for identifying a lesion in an input image fed to its input. The image fed to its input can be called an annotator input image (it is an image that comes from the processing unit, i.e., the processed image). The second lesion location data packet defines the location of one or more identified lesions (if such lesions exist).

Instead of "the one or more lesion possibly present/possibly identified" above it could also be said that lesion(s) having natural number or non-negative integer number, where natural numbers are taken to include zero and positive integers, i.e., put in another way, non-negative integers (because there can also be zero lesions).

The first lesion location data packet preferably has an image representation, where the lesions possibly contained therein have image visualisation; this is called an auxiliary lesion image. In the auxiliary lesion image (i.e., in the lesion image coming (originating) from the auxiliary unit; the attribute (adjective) "auxiliary" can be omitted) in the case of certain imaging modalities the lesions show up as accumulations (in other cases, as other structural differences), so a lesion image can also be referred to as "abnormal accumulation (difference) image" or "abnormal accumulation (difference) layer image", where the attribute "layer" indicates that the image only shows the abnormal accumulations (differences); the attribute "layer" may also be applied for the lesion image. Accordingly, considering the totality of lesions as a set, this basically comprises lesions, but it can also be empty: in such a case it does not comprise any lesions, i.e., there are no lesions can be identified; the set may also comprise one or more lesions, when the set is non-empty. The first lesion location data packet can be considered a mapping of the pseudo image to a subspace.

The role of the auxiliary unit is to keep under control the diagnostic value. During joint training (joint-training, collective training, common training, together-training), this unit is applied for improving the diagnostic value such that the trained system has as high an AUC value as possible (in other words, the image processing devices—i.e., the processing and annotator units—are measured and further trained such that their diagnostic value is improved), however, in the following such applications are also described wherein the auxiliary unit plays a role in preserving the diagnostic value.

Thus, the auxiliary unit preferably comprises a generator subunit (adapted for carrying out the training method, and, also in an embodiment of the system according to the invention, intended for use) and a discriminator subunit (both during the training method and during use), the term "auxiliary unit" is used as a collective name. The prefix "sub" can be omitted from the terms "generator subunit" and "discriminator subunit," or these can be simply called a "generator" and a "discriminator." In the case of the generator subunit it was specified that it is adapted for generating an auxiliary pseudo image (in relation to the term "pseudo image" see other considerations below); we will see that the generator subunit can have such a role at various phases (stages), so accordingly it may get further attributes (joint-training, pre-training, checking).

Also, due to its role played in joint training, the auxiliary unit can also be called a joint training (auxiliary) unit, or, due to its role played in the evaluation (in keeping it under control, see above) of diagnostic value, a medical evaluation unit (based on that, it could be called, for short, a MedEval unit based on the name of medical evaluation; the prefix NN can also be included before its name). However, the attribute "medical" included in its name indicates that this unit incorporates medical knowledge, and, accordingly, it can simply be called a medical auxiliary unit.

The ROC unit can also be called an ROC generator. It could also be named a (ROC) verification or comparison unit. The AUC parameter can also be called a diagnostic parameter (this nomenclature is in line with the fact that the higher the value of the parameter within the 0-1 range, the higher the diagnostic value of the results). Of course, the higher the diagnostic value, the better the system according to the invention in providing aid in making a diagnosis (cf. the CAD—computer aided diagnosis—approach).

The respective embodiments of the training method are of course able to train a system comprising one or more of these latters (i.e., the components have a function not only in the training method but are also included in the system ready for use, see the related considerations below). The system put into use and deployed to the user therefore comprises minimally the processing unit, as well as the discriminator subunit of the auxiliary unit.

It was shown above in connection with a number of units, that those are based on machine learning (briefly: machine learning), i.e., they are based on artificial intelligence and can be trained. The applied machine learning approach is, in many cases, an approach based on neural networks; many units are described in this approach. It is thus important to emphasise that the description based on a neural-network approach is not considered to be restrictive, i.e., at the generic level of the invention these components are based on machine learning. Besides that, as a typical example of the processing unit a filter is brought in, describing several features thereof in relation to the filter; however, a number of these disclosures can also be applied to the processing unit in general—in case the particular features allow for such generalisation.

Figure 4:
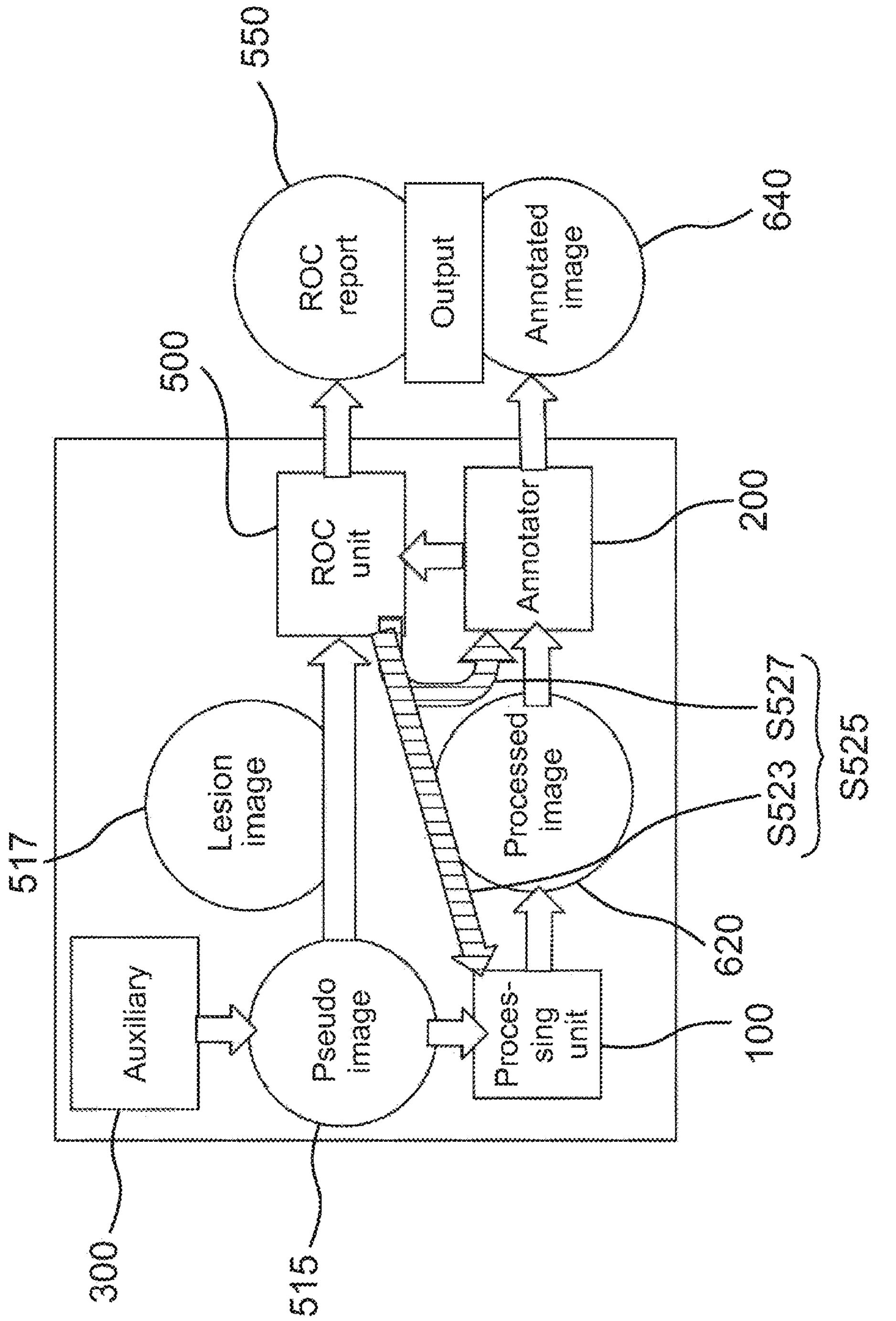
FIG. 4 is a block diagram illustrating an embodiment of the training method according to the invention.

The training method according to the invention comprises the following steps:

in a pre-training step the processing unit is trained applying (by means of) processing unit pre-training, the annotator unit applying annotator unit pre-training, and the discriminator subunit and generator subunit of the auxiliary unit applying auxiliary unit pre-training, wherein the processing unit pre-training, the annotator unit pre-training, and the auxiliary unit pre-training are independent of each other (the processing unit, annotator unit and auxiliary unit pre-trainings are illustrated in respective embodiments in FIGS. 1, 2, and 3A-3B; the pre-trainings could also be indicated with numerals—for example, first, second, third pre-training—in which case, of course, the numbers do not refer to succession; subjecting the processing unit, the annotator unit, and the auxiliary unit to separate pre-training involves that these units are based on machine learning, i.e., they can be trained by machine learning; pre-training can also be called preliminary machine learning), in a first cycle of a joint training (for the illustration of the joint training step S525 in an embodiment see FIG. 4; it can equally be called a joint training step or joint training) after (succeeding) the pre-training step for the respective joint-training auxiliary pseudo images generated by the generator subunit of the auxiliary unit trained applying auxiliary unit pre-training (by the generator subunit, trained applying auxiliary unit pre-training, of the auxiliary unit), by transferring (passing on, handing over/on) to the ROC unit, a second lesion location data packet determined by successive application of the processing unit and the annotator unit (in this order) and a respective first lesion location data packet corresponding to each joint-training auxiliary pseudo image (as it is illustrated in the figures, in certain embodiments, preferably, a lesion image-providing an image representation of the first lesion location data packet-corresponds to the pseudo images, the lesion image is typically, like in the embodiments of FIGS. 3A-3B, generated by the generator subunit together with the pseudo image itself; so, applying an extended term, the generator subunit could also be called a "pseudo image and lesion image generator")

determining a value of the AUC parameter by means of the ROC unit for the joint-training auxiliary pseudo images based on a comparison of the first lesion location data packet and the second lesion location data packet generated for each joint-training auxiliary pseudo image (comparing, of course, the data packets corresponding to each other).

Based on the description of joint training described above, it is noted that the ROC unit is thus applied for comparing the first and second lesion location data packets (for the process of this comparison in an embodiment see below), to put it simplified, the ROC unit examines whether the lesions (for example abnormal accumulations) defined by the first lesion location data packet essentially functioning as "ground truth", as well as preferably by the auxiliary lesion image (this image specifies, based on the available lesion image, the results the annotator should come up with) defined by it can be found among the lesions defined by the second lesion location data packet originating from the annotator, and vice versa, i.e., it examines how well the annotator did its job (has it found all lesions, has it introduced "false" lesions, that is, lesions not appearing in the auxiliary lesion image).

It is noted that according to the above an annotator unit is applied in the course of the training method, i.e., it takes part in the training that first involves pre-training it individually, while later on it also plays an important role in joint training. However, the annotator unit does not necessarily form a part of the installed (deployed) system, because, in accordance with the training, the processing unit also has a separate output, so it is independent of the training whether the system according to the invention supplied to the user is "stripped down" in comparison to the training configuration in that it does not comprise the annotator unit (for a discussion of related aspects see also further below).

In connection with the pre-training it is noted that, in order to make a decision on when to stop the training, accuracy is measured in the course of pre-training, preferably on a test set, stopping the process by a suitable method if the desired accuracy has been reached, or if it is clear that the network does not learn further (see: J. K. Terry et al.: Statistically Significant Stopping of Neural Network Training, arxiv: 2103.01205v3, 28 Jul. 2021, see also below the discussion on stopping the training).

The application of a machine learning unit (for example, neural network) in the generator subunit results in that the subunit generates images resembling the images included in the training database. Accordingly, it essentially generates a coherent database of (auxiliary) pseudo images into which medical expertise is "injected" by the training. In such a manner, an image database appropriate for the given task can be generated, which database can be utilised for joint training according to the objects of the invention. In other words, "on-demand" images are generated for the joint training.

The (auxiliary) pseudo images are therefore generated images—in other words, synthesised images—that are generated by a machine learning generator subunit. Reference can be applied for image generation (see the embodiment of FIG. 3A), but generating can be performed without reference, preferably based on a noise input.

The contents of the pseudo images to be generated by the machine learning generator subunit are established in the course of the training process (i.e., using the terminology applied in this description, in the course of pre-training). These artificially generated images are called pseudo images on the basis of this generation scheme, but terms like "generated image" (an image generated by a machine learning or machine-learning based generator subunit) or "synthesised image" (an image synthesised by the said generator subunit) can also be applied.

It is noted that the attribute "pseudo" could also be included in the term applied for images generated (output) by other machine learning units (neural networks), however, for labelling further other differentiation is applied. The attribute "auxiliary" is used in the term referring to the pseudo images originating in the generator subunit of the auxiliary unit—and to the lesion images corresponding thereto—in this sense, i.e., referring to the fact that they originate from the auxiliary unit. The attribute "auxiliary" has no role other than this, i.e., instead of "auxiliary," other terms could also be used, such as "first," or the term "auxiliary unit pseudo image" could also be used. However, without explicitly saying otherwise, the term "pseudo image" is meant to refer—as a kind of abbreviation—to the images generated by the generator subunit.

It is further noted that in some sense, auxiliary unit pre-training links together the discriminator subunit and the generator subunit of the auxiliary unit, because the collective term (umbrella term) "auxiliary unit pre-training" is applied to refer to the pre-training of these subunits. As it will be apparent from FIGS. 3A-3B below, pre-training can preferably be implemented in such a manner that the pre-training processes of the discriminator and generator subunits are related (they essentially learn in competition with each other, see below), but this is not generally required in the invention. Therefore, such a pre-training scenario can also be applied for the discriminator and generator subunits wherein the auxiliary unit pre-training comprises two (even independent from each other) parts: discriminator subunit pre-training and generator subunit pre-training (such a scenario is applied e.g. with an auxiliary unit implemented by a Variational Autoencoder, see below).

Above, the content of the first cycle of joint training has been given. In the method according to the invention, in at least one further cycle of joint training (see also in an embodiment in FIG. 4)

training of the processing unit and of the annotator unit is performed (training is performed on (in) the processing unit and on (in) the annotator unit; it is performed that the processing unit and the annotator unit are trained) applying a value of the AUC parameter determined in the previous cycle in a respective AUC parameter dependent term (member) of a processing unit joint-training loss function and of the annotator unit joint-training loss function (this step could also be called the step corresponding to substituting the AUC parameter value; see also the description below related to the joint-training loss function), and then (thereafter)

by transferring to the ROC unit for the joint-training auxiliary pseudo images a respective second lesion location data packet determined by the successive application of the processing unit and the annotator unit, and a respective first lesion location data packet corresponding to each of the joint-training auxiliary pseudo images, a value of the AUC parameter is determined.

According to the above, it is included into the name of the joint-training loss function whether it is a processing unit/annotator unit joint-training loss function according to the unit it corresponds to (this convention is also followed in the name of other loss functions; it can, however, be omitted in clear-cut cases).

A more detailed disclosure related to the joint-training loss functions is included below. In this disclosure we will provide potential generalisations of the AUC parameter dependent term, i.e., describe the manner it can depend on the AUC parameter (the AUC parameter dependent term preferably has such a dependence on the value of the AUC parameter that it has a local extremum for the unit value of the AUC parameter—i.e., for AUC=1).

In the following, the details of the case are described wherein the first lesion location data packet has an image representation this is the (auxiliary) lesion image. Above the lesion image that originates in the generator subunit has been introduced, which is a "layer image" in the sense that it represents, for example, the location of the lesions by preserving only the lesions from the (auxiliary) pseudo image, i.e., if all the other features of the pseudo image are deleted (for example image details corresponding to the skeleton), then this lesion image is obtained. In a reverse manner, this can also be formulated as follows: if the layer image (auxiliary lesion image) is subtracted from the pseudo image, then this leads to removing the lesions (for example, abnormal accumulations), thereby obtaining the healthy image (cf. FIG. 3B, where the subtraction step represents precisely that: if the abnormal accumulation layer image representing the lesion image is subtracted from the pseudo image, then this is obtained).

Accordingly, the (joint-training) auxiliary lesion image generated by the generator subunit preferably has image representation, i.e., it shows the lesions themselves according to their locations, i.e., at the locations where they can be found in the pseudo image. Besides that, the auxiliary lesion image can have other representation, thus it is not a generic requirement for example that by subtracting it from the pseudo image the healthy image should be obtained. Other such representations are also conceivable wherein by including, for example, another converting unit downstream of the generator subunit an essentially mask-like image can be obtained that takes a specific value—which is of course different from the values corresponding to the background of the image—at the locations of the lesions, while at other regions it does not incorporate any information (i.e., in such regions only the generic—for example, image—background is present).

For a comparison with the first lesion location data packet—which in the above-described case is specified by means of the auxiliary lesion image—the ROC unit also receives from the annotator a second lesion location data packet, some features of which are described below.

The annotation result dataset that involves (comprises) the second lesion location data packet is the output result of the annotator unit. It is the second lesion location data packet that is transferred by the annotator to the ROC unit (i.e., generally, the annotator identifies the second lesion location data packet, that is, it transfers the information required for identifying it; in other words, the annotator identifies the annotation result dataset the subset which corresponds to the second lesion location data packet, this task is assigned to the annotator rather than to the ROC unit; therefore by identifying this subset it can even transfer the entire annotation result dataset), which then compares it with the first lesion location data packet, for example, lesion image; as well as the image which has a role in pre-training and which is received by the physician during use as an output from the annotator unit is also a representation of this.

In the course of joint training, therefore, the annotator unit supplies data to the ROC unit in the form of the second lesion location data packet, for comparing in the ROC unit with the first lesion location data packet.

The second lesion location data packet originating from the annotation result dataset may have a different representation from the representation of the first lesion location data packet (and thus the lesion image). This is because due to its function the annotator unit is able to determine the location of the particular lesions.

The annotation result dataset defining the second lesion location data packet can be mapped, projected to a subspace in various manners. In use, the annotator unit (if it is a part of the system) outputs an image which such a representation-indicating, for example on a skeleton, the detected lesions, and possibly also indicating non-abnormal differences without regard to they not being lesions (cf. the right side of FIG. 15, where the bladder being a non-abnormal accumulation is also marked) that a user, a physician is able to interpret; this will be the annotated image (cf. FIG. 2). This is a mapping (visual representation) of the abstract annotation result dataset, which can be generated on the basis of the information contained in the annotation result dataset (the second lesion location data packet will be responsible for determining the location of the lesions also in this representation).

In accordance with the definition of the method included above, the lesion is the selected entity—in order to specify the diagnostic value—of which the recognition is made much more effective during joint training. Generally speaking, it can be said that finding (searching) of the entities appearing in the first lesion location data packet, i.e., preferably, in the auxiliary lesion image, is made more effective, and that these entities that appear therein at the level of the data are the lesions.

As it is also detailed, in addition to that the annotator may also learn to identify other (normal) structural changes in the annotated image; this can be facilitated by the pre-training of the annotator, and also by the optionally applied classification.

The annotation result dataset defines (contains) information—by its definition and due to its purpose for generating—related to the location of the detected lesions, i.e., it defines the second lesion location data packet.

The second lesion location data packet may have various representations (i.e., image and simply data representations, see also a representation described in detail below), where the location of each of the lesions is specified in some way, for example by defining a bounding box, an enveloping contour or enveloping set encompassing the lesion; or for example the representation with numerals described below (these representations can be applied in 2D and also in 3D).

The second lesion location data packet can also be considered a mapping of the annotation result dataset to a subspace; the function of the neural network of the annotator is to find this mapping. The annotator therefore provides information on the location of the lesions, even in form of islands (see above, for example by specifying "bounding boxes"). The ROC unit is able to perform image comparison, even a pixel-level comparison.

The annotation result is a dataset (in other words, the annotation dataset, i.e., the entirety of the data generated by the annotator). An image provided with annotations (alternatively: annotated image) is a mapping of this dataset to another subspace. In this, not only the lesions are marked but normal accumulations may also be marked therein (cf. FIG. 12 and the right subfigure of FIG. 15, which illustrates a typical annotation result, i.e., a typical annotated image). The annotator therefore produces such an annotation result dataset that for example has the two above-described typical subspace mappings. That is, it also defines the locations of the lesions, i.e., the second lesion location data packet can be obtained from it.

Accordingly, the second lesion location data packet generated by the annotator unit preferably contains information only on the location of the lesions (i.e. it specifies their location, typically indicating that simple background is present in the remaining parts; if no lesion can be identified, then only background, i.e. a state with no lesions, is designated in the lesion location data packet for the entire observed region). Similarly, the auxiliary lesion image contains information only at the lesion locations (there is typically a neutral background in other regions of these images also, see also below).

Figure 13:
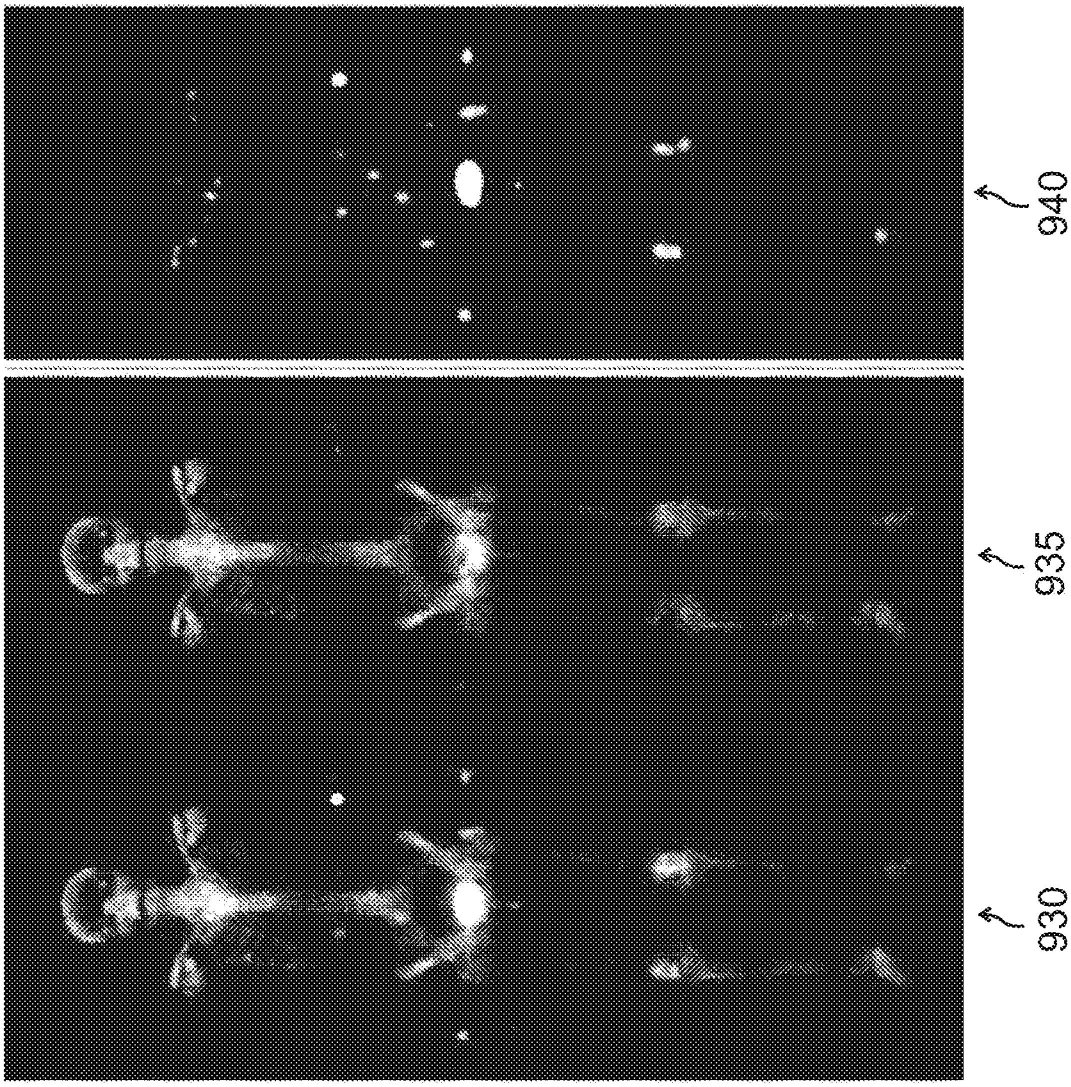
FIG. 13 illustrates various visualisations and accumulations.

The second lesion location data packet may have a representation that comprises 1-s at the pixels corresponding to lesion locations, and 0-s everywhere else (this is true if no classification is applied, but instead, as a more general case, the location of the lesions is determined simply; alternatively, for example analogously to the right image of FIG. 13, the background can be black and the lesion locations can be marked with a single colour, for example white). In such a case everything that the annotator marks as a lesion will be included in the image.

Figure 12:
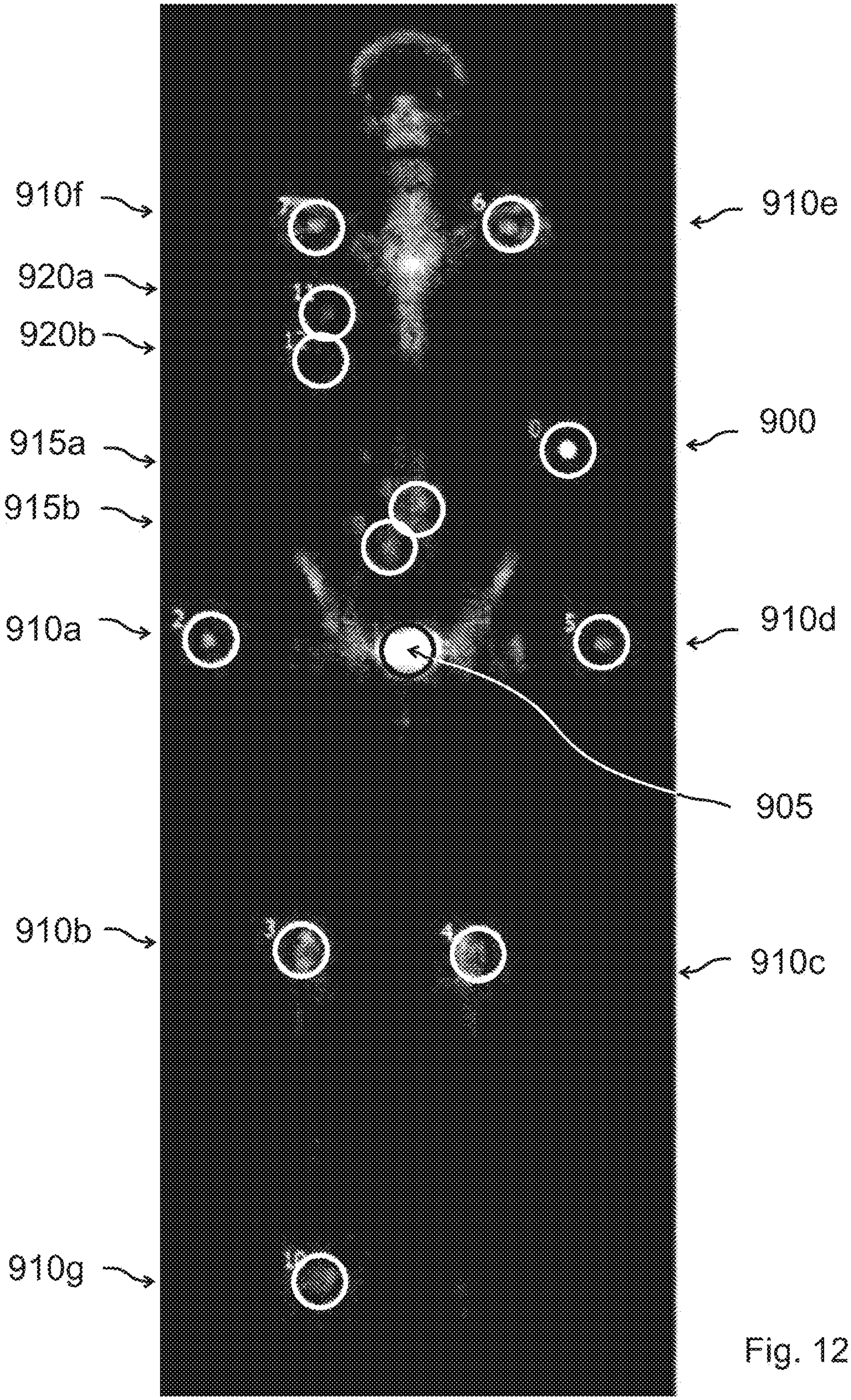
FIG. 12 shows accumulations in an exemplary image.
Figure 15:
FIG. 15 shows accumulations and also visualising a group of thereof.

In case classification is applied, in this representation there are not only 0-s and 1-s on the image as the different classes are by way of example denoted with other numbers (e.g. 1, 2, 3, etc.) against the background that is represented by 0-s (or with different colours, cf. FIGS. 12 and 15—in the former, by associating reference signs with the colours, an interpretation not involving colours is also made possible). In this representation, therefore, the location of the lesions is defined by that where there are non-0 values (values different from 0) in the lesion image (0-s are the background, while other numbers are classification information that can preferably be transferred). We shall later on return to the issue of classification, i.e., how the lesion candidates are classified into groups. A general trait of the representations involving numbers and colours is that a single type of information—for example a colour, numeral, or something else—is used in each pixel to denote a single type of entity (based on that, in the absence of classification, each lesion is denoted applying a single type of denotation information, while in case classification is applied, a given type of denotation information is associated with each group).

This involves therefore that the regions corresponding to each of the types of the differences (e.g., accumulations) have different serial numbers; for example, the number 1 is written into each pixel of region 1. Preferably, for example an index table (or other additional data) corresponds to the above that specifies the classification information for pixels having the value 1 (and other values): the location of injection, bladder, different from normal accumulation imaged with certainty, different from normal accumulation imaged with uncertainty (in relation to that it should be noted that in case classification is applied only this latter two types of abnormal accumulation, i.e. lesion, are included in the second lesion location data packet, all the others are included in a third annotation group corresponding to entities different from a lesion), etc. Therefore, in addition to the image output the index table may also play a role in the annotator output during the operation.

This representation is particularly preferable in the case of applying classification, because it allows that the classification (grouping) information can be transferred to the ROC unit, that is, in such a manner it is possible to visualise not only the locations of the lesions (as in the image representation) but classification information (grouping information; classification result) can also be associated with each lesion.

However, if classification is not applied, then it is not necessary to apply a representation in which it is possible to visualize classification information, that is, in this case the second lesion location data packet can even be of image representation (preferably, similarly to the auxiliary lesion image that is applied as the representation of the first lesion location data packet).

The task of the ROC unit is to compare the first and second lesion location data packets, i.e., to determine in which of them respective lesions have been identified, i.e. how many matches are obtained for the lesions across the two different sets of information).

For performing the comparison, data processing is preferably carried out by the ROC unit (preferably in one and/or the other case applying image processing, if there is image representation; the ROC unit will be set up for receiving the appropriate input format) on the first and second lesion location data packets, based on which, by comparing the lesion locations it is able to determine the ROC function after the completion of the epoch, so receiving two data packets with different representation (as lesion location data packets) would also not be an obstacle for the ROC unit, while their representation preferable may be matched with each other. It can be understood that it is feasibly able to compare, in all cases, the data related to lesion location that are received from the generator subunit and from the annotator unit. The lesion location data packet is therefore some kind of distribution map, in other words, a distribution table or information; it could also be called lesion location information. The location of the lesion is specified in this, in the case of an image representation, these are also interconnected by the dimensions/extension of the images.

The ROC unit also examines overlaps between lesions in the two types of lesion location data packet, and is also able to calculate the ROC curve based on the TP-FP pairs (see Julian B. Tilbury et al., *Receiver Operating Characteristic Analysis for Intelligent Medical Systems—A New Approach for Finding Confidence Intervals*, IEEE TRANSACTIONS ON BIOMEDICAL ENGINEERING, VOL. 47, NO. 7, July 2000.). The result is therefore also affected by the quality of the overlap between the lesions (e.g., a number between 0 and 1); the better matches between the lesion locations in the lesion location data packets indicate that the system is “well-behaved” for the given epoch, the higher the value of the AUC parameter.

Naturally, when performing the comparison, the ROC unit investigates not only the lesions that appear in both—first and second—lesion location data packets. If, for example, further lesions appear in the second lesion location data packet (in addition to the correct lesions), then this fact is also considered in the evaluation by the ROC unit. To put it in another way, such a scenario would naturally also be penalised by the training in which the second lesion location data packet were to contain many such lesions that are not included in the first lesion location data packet (that is, preferably in the auxiliary lesion image) performing the role of “ground truth”.

Allowed by the data processing (optionally, image processing) preferably applied therein, the ROC unit therefore compares the lesion location data packets arriving from the two branches. The comparison is thus not dependent on the applied representation, the restrictions preferably provided according to the invention on the definition of the first and second lesion location data packets (for example, applying classification) have an effect on the data to be compared, and so they can render the joint training process more effective (if the annotator is also trained to have the classification function, then it is able to even more effectively reject—i.e., to place into a "not to be shown" group—certain lesion candidates, bringing itself closer to the correct solution; on a certain level this happens even when classification is not applied).

The generator subunit generates, corresponding to the pseudo image, therefore a first lesion location data packet, preferably an auxiliary lesion image being a layer image type image that now only shows the lesions. The generator subunit typically possesses information on these lesions, the lesions being essentially placed on the image by the generator subunit (thereby turning it into a pseudo image, an image synthesised in this way). Accordingly, it is possible to generate the first lesion location data packet by the generator subunit, preferably in an image representation, as a lesion image that only shows the lesions.

Elsewhere in this application it is set forth that the generator subunit synthesises abnormal accumulations (a type (form) of lesion) into the image. This is related to the discussion of the previous paragraph in that the pseudo images are preferably obtained such that the lesions (i.e., the relevant changes, abnormalities to be found) are placed on it by the generator subunit, that is, the image serving as a starting point of image synthesis preferably does not comprise such lesions (this does amount to additively placing the lesions in the image; instead, the synthesised pseudo image and the corresponding first lesion location data packet are generated by a machine learning unit).

It is important to emphasise this also because the aim of joint training is that the lesions appearing in the first lesion location data packet, i.e. preferably in the auxiliary lesion image—the first lesion location data packet, i.e., preferably the auxiliary lesion image exclusively contains lesions—are identified by the system as effectively as possible (scoring as high an AUC parameter value as possible). For this process, the "ground truth" is provided preferably by the auxiliary lesion image; the annotator have to transfer to the ROC unit a second lesion location data packet that approximates this "ground truth" as closely as possible.

Taking into consideration that lesions can be found (are) in the "ground truth", this can be reformulated by maintaining that the aim of the joint training is to enable the annotator unit to discriminate the lesions as effectively as possible from other accumulations (non-abnormal accumulations, i.e., normal accumulations) that can be found in the input image in a given case. This is how it is possible to help the identification of lesions (abnormal accumulations).

In connection with the invention, it can thus be said (in order to cover each of the cases) that the first lesion location data packet, preferably auxiliary lesion image "does not comprise lesion or determines (defines) the location of at least one lesion". Accordingly, there is zero, one, or more lesion on it. If, therefore, no such lesion is found in relation to the first or second lesion location data packet that could be included therein, then the given lesion location data packet specifies that there are no lesions/no lesions have been identified (during joint training it can be expedient to also include cases like that, because the system can also be trained by the absence of the lesions to be detected; in this case the annotator gives a correct result if it sends to the ROC unit a second lesion location data packet not defining any lesions; this can be established applying the solutions described below involving classification, but also without applying groups).

In the disclosure of the invention included above mention is made of the first and the second lesion location data packets that are generated in different ways and have different roles in the training method according to the invention. Different naming conventions could also be applied for differentiating these from each other; this will be addressed later on.

The first lesion location data packet provides the basis for the comparison of the lesion location data packets performed by the ROC unit. Accordingly, occasionally the first lesion location data packet is also referred to as playing the role of "ground truth." It contains the lesions corresponding to the pseudo image, i.e., it contains data related to the location of the lesions which were placed on the image by the generator subunit during the generation of the pseudo image. That way, this data packet has controlled contents and serves as a basis for comparison. Accordingly, it could also be called a "basic" or "basis for comparison" lesion location data packet (reflecting the fact that it fulfils the function of a "ground truth", the other data packet, the second lesion location data packet is compared against it).

It is the second lesion location data packet is that which is obtained by evaluating the pseudo image by means of the processing unit, and then by means of the annotator unit, then it is compared with the first lesion location data packet in the ROC unit. Therefore, the pseudo images that are consistent (are in conformity) with the first lesion location data packet due to the contained lesions serve as a starting point for the second lesion location data packet. Thus, as the first lesion location data packet is the "ground truth," by comparing the first and second lesion location data packets in the ROC unit the performance of the processing unit and the annotator unit can be measured.

Only the lesions put in the pseudo image by the generator subunit are in the first lesion location data packet. Conversely, there are data packet portions in the second lesion location data packet that have been identified as lesions by the annotator unit. These are thus the lesion candidates, among which as the training progresses, preferably increasingly only those remain that are also included in the "ground truth," i.e., the first lesion location data packet. If classification is performed, it can make more efficient filtering out those candidates that are finally not proven to be lesions, because in that case only those data packet portions (i.e., entities found by the annotator) are included in the second lesion location data packet that have been identified by the classification (at least uncertainly) as lesions.

To reflect this, the second lesion location data packet could also be called a lesion candidate location data packet. It can even also be called temporary/transitional lesion location data packet or processor-annotator lesion location data packet (since the contents of the first and second lesion location data packets are known, as far as their nomenclature is concerned it is only important that they can be clearly distinguishable from each other). However, applying the current terminology is supported also by the fact that the second lesion location data packet incorporates such entities that have been identified as lesions by the annotator unit, i.e., from the aspect of the annotator they are all lesions, the annotator seeks to find all lesions and to avoid, as much as possible, marking as lesions such entities that are not lesions. The joint training process assists it in this task. Also, reflecting the alternative term "basis lesion location data packet" applicable to the first lesion location data packet, the second lesion location data packet can also be called a lesion location data packet that is "derived (by means of the system/the processing unit and the annotator unit)" or, reflecting the alternative term "comparison basis" it can be called "to be compared (with the comparison basis)".

In an embodiment of the training method the identification of lesions can be facilitated as follows. In the present embodiment, for determining the second lesion location data packet, a search step is performed by means of the annotator unit on a joint-training processed image obtained by means of the processing unit from the joint-training auxiliary pseudo image (i.e., the output of the processing unit during joint training) for determining location of a lesion candidate.

In case a lesion candidate is found on the joint-training processed image in the course of the search step, the one or more lesion candidate identified as lesion is classified either into a first annotation group of safely identifiable lesion or into a second annotation group of uncertainly identifiable lesion, or is classified into a third annotation group of lesion candidate different from a lesion, and if there is a lesion (i.e., an identified lesion candidate) classified into the first annotation group and/or into the second annotation group, then only location of one or more lesion classified into the first annotation group and into the second annotation group are determined in the second lesion location data packet (according to above, in the given representation different numbers can be associated with the different groups, and these can be illustrated by the numbers in the second lesion location data packet such that the classification information is preserved).

The phrasing "only the lesions classified into the first annotation group and into the second annotation group are determined in the second lesion location data packet" is taken to mean that no other lesion-related information will be included in it. This is said also by that the location of these lesions are determined therein.

The entities found during the search step are called "lesion candidates" because it is not sure that they are lesions; they may also be classified in the third annotation group where the entities other than lesion get into, i.e., those lesion candidates that in the course of the classification have not proven (even uncertainly) to be a lesion. Therefore, it is sure that (according to the classification) such entities are not lesions. The classification may of course "make a mistake" and tolerances are typically required for classification; the accuracy of classification can be controlled by adjusting the parameters affecting it in the annotator unit (on the advantages of classification see also the discussion of a further embodiment in the description of FIGS. 17A-17F, where in the first lesion location data packet intensity information is also associated with the lesions).

Accordingly, the lesions can be preferably classified into two groups based on the degree of certainty of their identification as lesions (i.e. abnormal). Accordingly, these can be taken to the group of safely identifiable lesions and to the group of uncertainly identifiable lesions. This classification is especially preferable because it can get significance in the comparison performed in the ROC unit, which can be taken into consideration by the training. In the terminology, the word "safely" means that the entity is safely identifiable, i.e., it is highly probable that is it really a lesion. Conversely, the word "uncertainly" means that the safety, high probability is not present, i.e., it is much more uncertain that it is really a lesion or not. These could also be called "safely identifiable" and "not safely identifiable".

It is preferable, for example, if the result of the comparison is that all the safely identifiable lesions are also present in the first lesion location data packet, i.e. preferably in the auxiliary lesion image (thereby the annotator essentially subjects the found lesions to filtering such that the second lesion location data packet comprises as much as possible only those lesions that originate from the generator subunit). In relation to that, it has also value if a false lesion hit is classified among those being uncertainly identifiable. Based on that the progress of the training can be evaluated, and by providing adequate feedback a favourable level of result quality can be achieved, with the ratio of safely identifiable ones is better and better and less and less lesions being classified into the group of uncertainly identifiable.

Another piece of information for the ROC unit that can be associated with each lesion is the annotation group into which the particular lesion has been classified into during the classification, i.e., since these are got into the second lesion location data packet, into the first annotation group of safely identifiable lesion or the second annotation group of uncertainly identifiable lesion.

Based on the transferred classification information (i.e., the extra information corresponding to the lesions) the ROC unit is preferably able to perform weighing while determining the ROC curve and thus the AUC parameter: for determining the ROC curve the lesions in the "uncertainly identifiable" group will have smaller weight than the safely identifiable ones. As a result of this, if for example there has been a mistake in identifying a safely identifiable lesion (i.e., for example it cannot be found in the first lesion location data packet functioning as "ground truth"), then the value of AUC will deteriorate to a greater extent (cf. on calculating the ROC curve the discussion in Julian B. Tilbury et al., *Receiver Operating Characteristic Analysis for Intelligent Medical Systems—A New Approach for Finding Confidence Intervals*, IEEE TRANSACTIONS ON BIOMEDICAL ENGINEERING, VOL. 47, NO. 7, July 2000.)

Preferably, therefore in this way, in case the ROC unit receives the classification information related to the classification and utilises it in the evaluation (i.e., the ROC unit is configured in such a way; on the classification information see also further below), the ROC unit gives feedback indirectly, trough the value of the AUC parameter on the effectiveness of finding the lesions by the annotator unit. Without applying these groups, the system would be more rigid, while with them it is much more flexible and adaptive.

According to the general concept of the invention it is specified that the ROC unit compares the first lesion location data packet arriving directly from the generator subunit—and thus functioning as "ground truth"—with the second lesion location data packet that arrives from the other branch and is generated by the annotator unit after a processing performed by the processing unit, in order to establish how good the performance of the branch constituted by the processing unit and the annotator unit is. Based on the comparison, feedback is given by the ROC unit to the processing unit and the annotator unit; with the help of which these are subjected to further training in the course of joint training.

In the approach according to the above, the contents of the first lesion location data packet are specified by the generator subunit in an arbitrary manner. As set forth above, in an embodiment the contents of the auxiliary pseudo image are obtained such that the generator subunit synthesises lesions onto a base image, i.e., it places the lesions on it (as a machine learning unit, it generates pseudo images having these lesions on themselves). The same lesions are then placed by the generator subunit in the lesion image (generally speaking, in the first lesion location data packet; it is aware of these lesions because it was the same unit that placed them in the pseudo image). In this approach, the above can also be considered in a way that the ROC unit examines the efficacy of detecting—by the branch constituted by the processing unit and the annotator unit—those lesions of which it received information in the auxiliary lesion image.

According to the above, the process of the joint training can also be facilitated by the application of classification in the annotator and transferring therefrom to the ROC unit only those lesions that can be identified either safely or uncertainly, i.e., these lesions will be included in the second lesion location data packet. This is done because in this manner the lesions that are only identified as such by the annotator but in reality, are irrelevant lesion candidates (for example because they are not abnormal).

These irrelevant lesion candidates—because the generator subunit synthesised lesions onto pseudo image, which lesions were then placed in the auxiliary lesion image—are preferably not present in the "ground truth", so, by applying classification and by including in the second lesion location data packet only the lesion candidates that have been identified as lesions, the first lesion location data packet has preferably been approximated at once.

However, if classification is not applied in the annotator, and thus those are not removed which are non-abnormal, i.e., the lesions not present in the auxiliary lesion image are not removed by classification, so—because the annotator has found them—they are included in the second lesion location data packet, in the course of the joint training process the annotator will even converge towards not including them in the second lesion location data packet, because it will receive feedback from the ROC unit indicating that these are not right hits, since they cannot be found in the "ground truth". More effective operation is provided by generating the second lesion location data packet after performing the above-described classification into groups in the annotator; however, as it was set forth above, it is not necessary to apply this classification.

In relation to the (auxiliary) pseudo images it is noted that preferably a new epoch of pseudo images can be generated for each cycle (the pseudo images can also be generated in advance), but in theory a single set of images can also be applied repeatedly (in this case the contents of the epoch is unchanged and is generated at the beginning of the process). Besides that, generating can also be performed on an alternative method schedule provided that the required pseudo images are made available on time.

The processing unit, the annotator unit, and the auxiliary unit are machine learning units (machine learning-based units, units suitable (adapted) for machine learning), i.e., their operation is based on artificial intelligence. Accordingly, these units can be subjected to (pre-)training, which can be followed by the joint training of the processing unit and the annotator unit. As it will be shown below in the detailed description of training, the pre-training for these units is carried out independently of each other (units having different functionality are trained separately, applying inputs and outputs corresponding to their functions; see FIGS. 1-3B), then, during joint training the units will be linked together by the pseudo images propagating through the processing unit and the annotator unit in the course of the learning; after that by the loss functions of both the processing unit and the annotator unit depending on the AUC parameter that returns from the ROC unit and also contributes to the training (see FIG. 4).

It is also noted that pre-training and joint training belong to different—successive—phases (stages) of the training method according to the invention (pre-training is carried out first, followed by the joint training cycles utilising the AUC parameter). Pre-training could also be called "auxiliary training"; a special term is used to refer to it in order to allow the various phases of training to be distinguished from each other (i.e., the name should indicate that the training starts with this).

The invention also relates to a system for aiding evaluation of an input medical image (an embodiment of the system is shown in FIG. 5), the system is trained by means of an embodiment of the training method according to the invention, and the system comprises

- the processing unit adapted for generating a processed image from the input medical image, and,
- the auxiliary unit that has the machine learning-based discriminator subunit adapted for determining a discriminability result by subjecting the input medical image to a discriminability test (discriminability examination, discriminability investigation; can be also called a distinguishability test, i.e., a test performed applying a discriminator subunit or—as it is also called—discriminator).

The discriminator subunit is preferably adapted for issuing a discriminability warning (expediently intended for the user) in the case of a discriminability result—see the "no" branch of the decision unit 560 in FIG. 5 below corresponding to establishing discriminability—corresponding to discriminability (that is, such a warning can be issued by the discriminator subunit—as the component corresponding to this subprocess—in case it executes the branch corresponding to discriminability, but it may also be said that the warning is issued by the system). It is noted that this option can also be applied to the system in general, i.e., not only to the embodiments comprising the annotator unit and the ROC unit but also to embodiments that do not comprise an annotator unit and an ROC unit.

Therefore, if the discriminability result (that is also mentioned in the description of the discriminator subunit) indicates discriminability, it indicates that the image currently being examined can be discriminated from the images that the system was trained on. In such a case the image cannot be applied for aiding the evaluation of these, so a discriminability warning can be issued by the discriminator subunit (indicating that the system cannot be further used for aiding evaluation with preserving the diagnostic value, i.e., that there is discriminability). It is important to note that issuing the discriminability warning does not necessarily mean issuing a warning to the user (to the outside world); the issued warning may be applied only for marking the image corresponding to the warning, i.e., for recording for the image that it has been decided that it can be discriminated. The configuration method built on this is also based on this function of the discriminability warning (see below).

The system according to the invention optionally (i.e., in an embodiment thereof) comprises the annotator unit adapted for generating an annotated image on the basis of the processed image. As it was set forth in the introduction to the invention, of the processing unit and the annotator the system mandatorily comprises only the former, i.e., the processing unit (for a discussion of related aspects see also below). As it is also shown by the introduction, an essentially main feature of the system according to the invention is that it is trained by means of the training method according to the invention. In relation to that it is important to emphasize that, according to the above, the annotator unit does take part in the training of the system according to the invention (thereby training method becomes an internal, concealed portion of the system trained by it).

The training method—which is realized on the components of the system utilising also the annotator unit—is differentiated in this aspect. Conversely, in the apparatus deployed (stationed, placed) to the user that incorporates the system according to the invention (i.e., it is among the system components of the installed system), this component is optionally not built in depending on the demand, only the suitably prepared (i.e., subjected to pre- and joint training) processing unit (for example, a filter). Of course, if it is desired so, preferably the annotator unit may also be arranged in the system according to the invention.

If the annotator unit is not included in the system (not built into it), only the processing unit, then the output of the latter will constitute the output of the system in accordance with the given use of the system. The performance and operation of such a "standalone"—independently operated, self-existing—processing unit/filter is completely different from the case in which no joint training would have been applied. Besides that, in this embodiment of the system according to the invention as an important component—in addition to the standalone processing unit—an auxiliary unit is arranged having a discriminator subunit that is responsible for testing discriminability and is adapted for issuing a discriminability warning.

The invention also relates to a configuration method that is adapted for configuring the system according to the invention in case of issuing a discriminability warning (for related details, see the description of FIGS. 8-10 below).

The term "image" as used in the present description can mean a planar (ordinary 2D) image, and also a volumetric image (i.e., a 3D volumetric image, for example in the case of SPECT). In the digital case, the former and the latter are represented applying pixels and voxels, respectively. Accordingly, what is disclosed for images below, it is also meant to volumetric images (the description can be interpreted analogously for 2D and 3D images).

In case a given image modality is chosen, in the course of the method the image retains its character (i.e., for example for the input medical image the further character is fitted in the method and the system, wherever a processed or generated image is utilised). Transition between these is possible in the case, if a secondary image is also applied in addition to the primary image. In such a case the secondary image can be of a different modality than the primary one (for SPECT, for example CT, MRI, ultrasound), and is treated accordingly in the training method and in the system.

After giving above a disclosure of the system and the method adapted for training it, hereinafter the important components required for training will be described in respective embodiments (these disclosures were referred to above in relation to the given components), followed by a disclosure of how these components co-operate during the training and during the operation in respective embodiments (illustrated by FIGS. 4 and 5). First, therefore, each component of the system will be described in detail.

Figure 1:
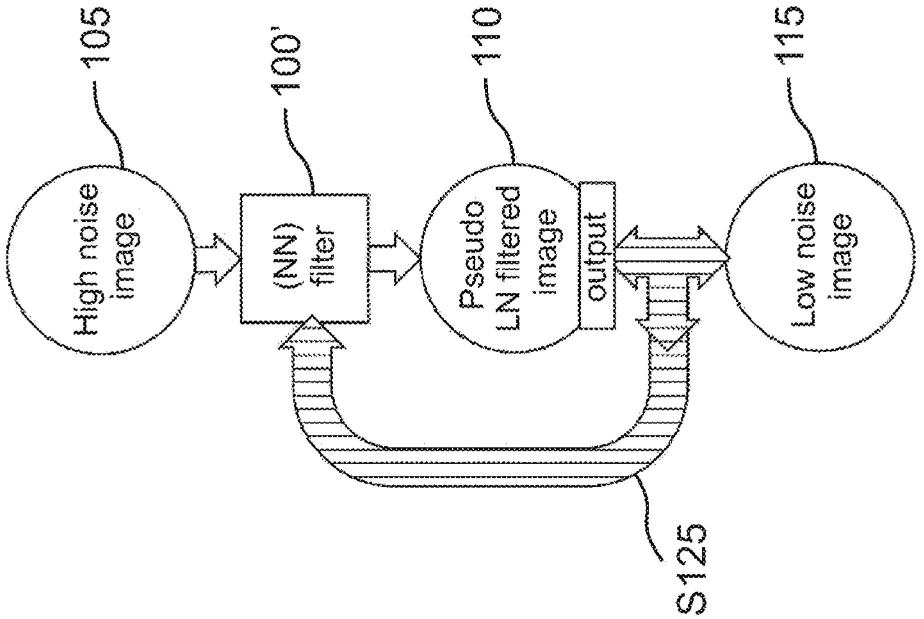
FIG. 1 is a flow diagram illustrating the training of the filter unit in an embodiment of the method according to the invention.

According to the above, therefore, the first important component is the processing unit that in the embodiment of FIG. 1 is a filter 100' implemented by a neural network (for short, NN filter or NN-filter; the abbreviation "NN" being used to refer to the term "implemented by neural network"). In relation to this embodiment, the followings are specified.

The filter 100' typically operates on planar images or on a reconstructed "volume". Depending on the particular field of application, the filter 100' is utilised on raw or reconstructed images generated by an imaging apparatus, i.e., typically a gamma camera/SPECT/PET/CT/MRI apparatus.

In a preferred implementation, during the training of the neural network of the filter 100' images produced utilising scanning protocols applied in clinical practice are recorded (these can be considered LN, "low-noise" images), and from these images so-called statistically degraded (HN, "high-noise") images are generated artificially, by resampling them. In the course of this training step implementing the pre-training (see operational step S125 below) the parameters of the neural network are tuned applying a suitable method until the generated pseudo-LN images generated by the network from the noisy HN images are as similar as possible to the (starting) LN images (see the description of FIG. 1 below); the image thus synthesised is considered the NN-filtered image of the input image.

In FIG. 1, therefore, the training process applied in the present embodiment is illustrated, i.e., in line with the above terminology, the training of the implementation of the processing unit in this embodiment, the filter 100' applying filter unit pre-training (for short: pre-training). In a manner described above, mutually corresponding higher noise (HN) images 105 and lower noise (LN) images 115 are applied for training. During training, respective higher-noise images 105 are fed to the filter 100' that generates a respective lowered-noise (LN) filtered pre-training image 110 from each input image. It is noted that in the name of the images generated by the filter 100' the attribute "pseudo" could also be applied, because the machine learning unit based for example on a neural network does not perform filtering in the conventional sense of the word, but rather synthesises a filtered image. This also holds true for the other machine learning-based units, i.e., the attribute "pseudo" can be included in the names of the outputs thereof.

In operation, the lowered-noise filtered pre-training image 110 constitutes the output of the filter 100' that plays the role of processing unit in the given embodiment. In turn, during the training the lowered-noise filtered pre-training images 110 are compared with the lower noise (LN) image 115 corresponding to the initial higher noise (HN) image 105.

In FIG. 1, this step is illustrated by the three-pronged arrow corresponding to the calculation of the loss function (a separate operational step can also be assigned to this); appropriate training can be applied by the corresponding training pairs having high and low-noise. The difference detected during the comparison is utilised for training the filter 100'. This is illustrated in FIG. 1 by an operational step S125 corresponding to training implemented applying e.g. the back-propagation method (see Aggarwal, C. C. (2018). *Neural Networks and Deep Learning*. Cham: Springer., page 357, and https://towardsdatascience.com/understanding-backpropagation-algorithm-7bb3aa2f95fd) indicated by the entire hatched arrow in the figure, i.e., the triple-pronged arrow and the returning arrow. In the pre-training step, feeding back information can be indicated in the figure; while the training itself always involves more than that, including for example the tuning of the machine learning unit (e.g. adjusting the weights of the neural network), which is carried out based on the fed-back information in the machine learning unit itself (see also below the discussion related to the loss function).

In FIG. 1, therefore, a pre-training step corresponding to filter unit pre-training performed as processing unit pre-training is illustrated in an embodiment. In this embodiment, in accordance with the above, a filter unit transforming the input medical image into a lowered-noise filtered processed image is applied as a processing unit. Furthermore, preferably in the course of filter unit pre-training carried out in operational step S125, training of the filter unit 100' is performed by means of the filter unit pre-training loss function (this is applied for training the filter unit during the pre-training; similar terminology is applied in the case of other pre-training processes) corresponding to the training, after performing the following steps multiple times (after multiple performing the following steps):

by means of the filter unit 100' generating a lowered-noise filtered pre-training image 110 based on a higher-noise training image 105, generating (composing) a first difference result by comparing the filtered pre-training image 110 and the lower-noise training image 115 corresponding to the higher-noise training image 105 (the attributes "higher" and "lower" included in the names of the images 105 and 115 are adapted for comparison with each other, they could also be called high-noise and low-noise images, or other denominations e.g. serial numbers could also be applied), and applying in the filter unit pre-training loss function a term being dependent on the first difference result (i.e., the difference results obtained from the multiple execution are all taken into account in the loss function, applying therein, in each execution, a term dependent on the current value of the first difference result, i.e., a summated term of such terms is added to the loss function).

The above steps show that during each instance of executing the steps a first difference result is calculated, and then a term dependent on this result is included (applied) in the loss function. The above could alternatively have been set forth (for other loss functions as well) as during each execution the current result is calculated and a term dependent on the current value of the result is applied.

The attribute "training" is included in the terms referring to images adapted for performing training in the course of the pre-training (i.e., they form a part of a suitable training database), while the terms referring to images generated during pre-training include the attribute "pre-training". This convention has been followed in relation to each of the pre-training processes, but alternative terms could also be used to refer to these images (for example, serial numbers or the attribute "input/output" or other denotations could also be included therein).

FIG. 1 is therefore a schematic flowchart of training a filter 100' implemented by a neural network, in the course of which a comparison of a pseudo-LN filtered image synthesised by the NN filter 100' and a low-noise image/volume having good statistics, which can also be expressed with the formula (1) below. Also in accordance with the above, this can be achieved for example by backtracking the changes of an L1-metric generated loss function $$L1LossFunction = \sum_{i=1}^{n} |y_{true} - y_{predicted}| \quad (1)$$

for example, applying a back-propagation algorithm. In the formula (1) the summation runs through all pixels and through all the images of the training database, while the LN image with good statistics is noted as $y_{true}$ and the pseudo LN filtered image is noted as $y_{predicted}$ (in this description different databases are mentioned, in many cases the database mentioned is meant to be the training (image) database; however, there are also databases adapted for storing images, see a database 250 of annotated images and an image database 575). For more information related to the L1 metric and the L2 metric referenced below see https://machinelearningmastery.com/vector-norms-machine-learning/.

In an embodiment, an autoencoder-type NN filter having a U-topology is applied (Ding Liu et al: When Image Denoising Meets High-Level Vision Tasks: A Deep Learning Approach, arXiv: 1706.04284v3, 16 Apr. 2018; Ronneberger O., Fischer P., Brox T. (2015) U-Net: Convolutional Networks for Biomedical Image Segmentation. In: Navab N., Hornegger J., Wells W., Frangi A. (eds) Medical Image Computing and Computer-Assisted Intervention—MICCAI 2015. MICCAI 2015. Lecture Notes in Computer Science, vol 9351. Springer, Cham, https://towardsdatascience.com/u-net-b229b32b4a71), which is trained in the above-described manner, but any other type of machine learning image filter that is intended to improve the signal-to-noise ratio of the image can also be applied.

It is a characteristic of NN filters therefore both the input and the output is burdened with significant noise, but in spite of that these are able to identify the structures in the images and generate an image having enhanced contrast, see in FIGS. 11A-11D.

In case of a noisy image, the risk of not detecting a real additional accumulation (i.e., in abnormal case, lesion) could increase. In a particularly preferable manner, joint training is aimed precisely at reducing the risk of such mistakes (failures). The processing unit also contributes to obtaining adequate diagnostic value even in case of high noise, i.e., joint training has the added advantage that it generates well-detectable results preferably also in the case of higher noise. It is noted here that in FIGS. 11B and 11D the image has only been filtered (i.e., the noisy image has been subjected to the processing unit); the particular accumulations (in general: structural differences) detectable in the image are only turns out after the annotator has been applied.

The NN filter 100' shown in FIG. 1 can be generalised, i.e., for the purposes of the invention it can be substituted by any other processing unit (or image processing unit) that is able to diagnostically enhance (visualise) certain elements of the image. Further examples are given below for the possible functions that can be performed by the processing unit if it does not function as a filter. For example, such a possibility is constituted by colour scales that are adapted for enhancing or suppressing portions of the image with a given intensity.

Figure 2:
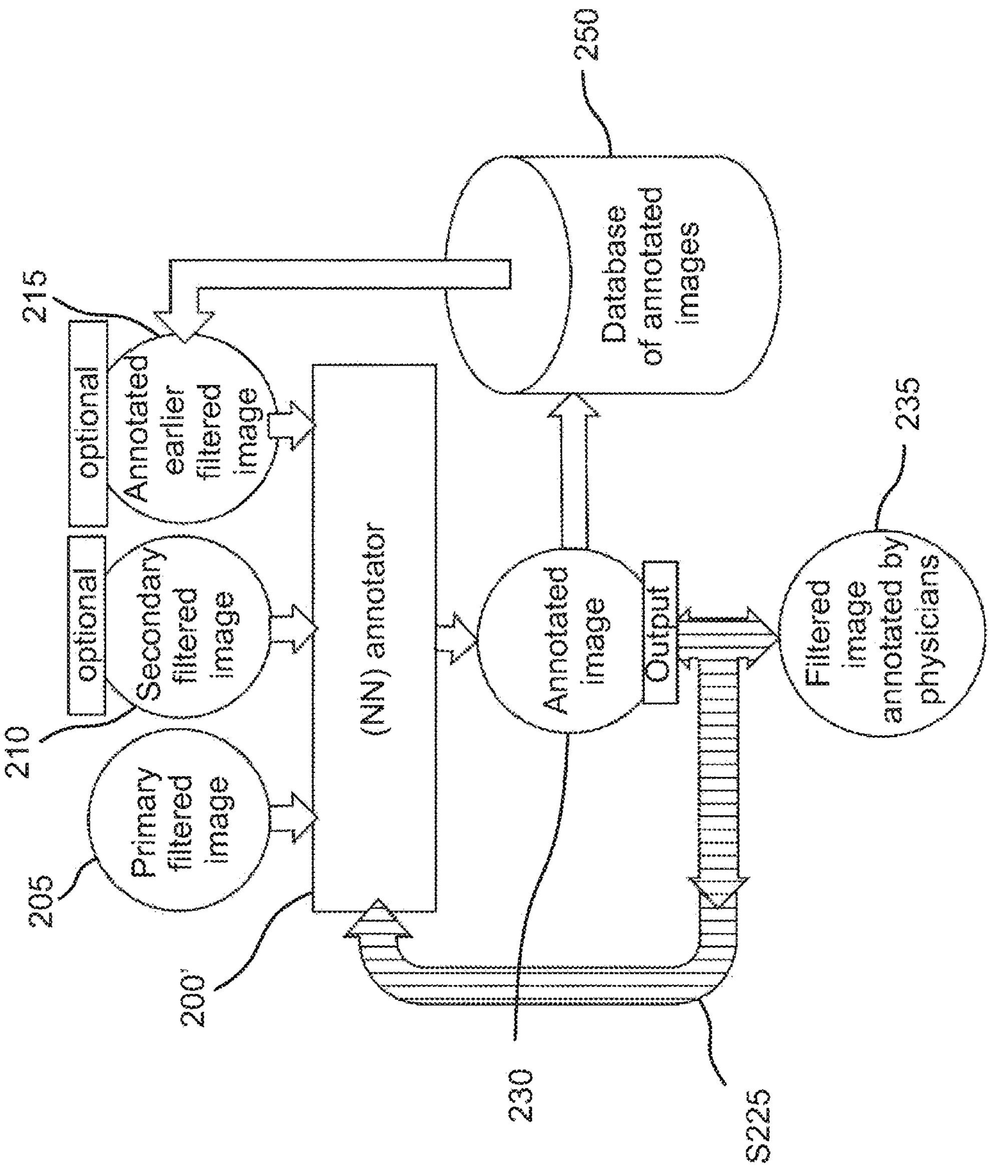
FIG. 2 is a flow diagram illustrating the training of an annotator unit in an embodiment of the method according to the invention.

However, an image filter implemented applying a NN filter could not ensure by itself that information that could be relevant for aiding the issuance of a clinical diagnosis is not placed to the image or is not removed therefrom. Because of that, preferably additional components are also utilised in the invention (at least in the training method), the annotator is such a second important component, of which an embodiment implemented as a NN annotator unit 200' is shown in FIG. 2.

The NN annotator unit 200' is adapted to find in the filtered images the accumulations and characteristic features/structures (i.e., in general, structural differences), and preferably, to classify them. It marks the locations of these features in the image (performs segmentation; in the terminology of the field "segmentation" refers to highlighting, cutting out a portion of an image, in this case for example the algorithm selects those regions of a whole bone scanned image where it detects accumulations being different from normal), and classifies these structural differences for example as "injection location", "accumulation in joint" or "potentially abnormal accumulation". Furthermore, it is also able to categorise accumulations/structures using a two or more state scale (certain, uncertain, etc.; for the related details see the example with detailed description in connection with FIGS. 12, 13, 14 and 15).

The NN annotator unit 200' can receive one or more images simultaneously. In all cases it receives a primary image that can be e.g., a planar anterior or posterior whole-body image, or a reconstructed volume (e.g., SPECT, PET, CT, MRI volume).

A detailed description of FIG. 2, i.e., the annotator unit pre-training of this embodiment of the annotator unit (an annotator unit 200') is given below.

According to the above, the input of the annotator unit 200' is constituted by an annotation input training image 205 (this is preferably a primary filtered image, which can also in this case be both a planar and a volumetric image). Optional inputs can be a second (secondary) filtered image 210, and an annotated, earlier (auxiliary) filtered image 215 (for more details on optional inputs see below; these are not necessarily filtered images, because in certain cases they can adequately assist annotation even without filtering or other processing). The latter is expediently taken from a database of available (accessible) annotated images 250, i.e., an image playing such a role—reflecting an earlier state of the same patient—is available for application in the training process (during use, such previously annotated images can be taken into consideration—for example for a structured medical record making—in case the annotator unit 200' is trained for that in this phase). The images 205, 210 and 215 are of course related to each other.

It is noted with reference to the discussion included below with respect to joint training that such a subcase is also possible wherein the annotator receives the optional images during pre-training, while during joint training it only receives the primary images (i.e., at this phase it has only a single input).

Referring to FIG. 4 it is noted that such a subcase—for example, a subcase having a character of multiple channels—is also possible wherein the auxiliary unit 300 also synthesises an optional image, for example CT image, in addition to the primary image. In this case, this optional image establishes a combined pseudo image along with the pseudo image 515. In such a case, preferably one half of the combined pseudo image, for example the SPECT portion is input to the filter (processing unit), while the annotator receives the filtered SPECT image and the other half of the combined pseudo image, i.e., the synthesised CT image (therefore the processing unit does not necessarily process the image fed into the annotator unit, because it is not always necessary to the process the secondary image, as it may show such details—possibly even only due to its modality—that may help in the annotation of the primary image in the annotator).

According to FIG. 2, the training of the annotator unit 200' is performed as follows. The appropriate inputs are fed to the annotator unit 200' which then outputs an annotated pre-training image 230. This annotated image is compared with an annotated training image 235 (or in other words, filtered image annotated by physicians) that constitutes the "ground truth".

In the figure, this step is illustrated by the three-pronged arrow corresponding to the calculation of the loss function (a separate operational step can also be assigned to this); the physician-annotated filtered images are compared with the ground truth (the system is trained applying labelled images; it must find and correctly categorise the accumulations). The difference resulting from the comparison is utilised for training the annotator unit 200'. In FIG. 2 this is illustrated by an operational step S225 corresponding to training implemented utilising back propagation (the entire hatched arrow corresponding to it). Also in this case, information feedback can be marked with the reference sign (see also below in connection with the loss function).

If a physician is uncertain regarding the nature of the accumulations, according to the typical diagnostic protocol a secondary (additional) examination can be requested (this is manifested in FIG. 2 as the secondary filtered image 210), for example, after taking a planar bone image, one may take a SPECT image of a given bodily region, or in another case, taking a CT/MRI image with the same or a different apparatus. The secondary image thus produced, or a processed, reconstructed and filtered (e.g., by a NN filter) image constitutes an optional input of the NN annotator together with the primary image.

A third—also optional—input of the NN annotator is an earlier annotated patient recording that is retrieved by the physician performing the examination according to the patient's condition in order to aid in the evaluation in the therapeutic process, i.e., to compare with the accumulations detected earlier (see above the annotated earlier filtered image 215). These earlier examinations are stored in an appropriate database (such a storage database is the database 250 of annotated images), wherein, in addition to the images taken of the patient, the accumulations/structures that were identified and annotated (marked) earlier are also registered and stored, optionally such that they are assigned to anatomic regions (structured medical/clinical recording).

The object of the system according to the invention is to identify the lesions in an input medical image. Lesions can also be termed "abnormal differences;" a lesion is a localised pathological/structural change, i.e., such a difference in the organs or tissues of the body (an organic or tissue difference/change) The lesion generator generates lesions into a lesion image.

The lesions may appear in various forms in the different medical imaging modalities; however, according to the invention these forms can be treated according to uniform principles. In some imaging modalities, the types of lesions detectable in them are also illustrated. Imaging modalities can be categorised according to various aspects, a categorisation possibility is based on whether an agent adapted to facilitate imaging (for example, a contrast agent or isotope) injected to the patient is applied or not:

- in case of CT and MRI such material is either not applied for facilitating the imaging, or a contrast agent is injected to the patient with this aim,
- in the case of SPECT and PET, imaging is aided by injecting an isotope to the patient, injecting of it is necessary,
- in case of X-ray and ultrasonic no such material is applied.

In case a contrast agent or isotope is applied, accumulations naturally form at the injection location and in the bladder. These are normal accumulations; their presence indicates that the imaging process has been completed successfully. These normal accumulations are not lesions; the invention is not aimed at detecting them, they are present on the pseudo images corresponding to these tests already before the lesions are synthesised, or must be present in the pseudo images, however they are not part of the "ground truth" corresponding to the lesions (considering also that an examination is considered failed if they are not present). Therefore, they can be detected against a background also comprising the normal accumulations, with the aim that the system can discriminate the lesions—which in this case are abnormal accumulations—from the normal accumulations (if classification is applied, the normal accumulations are classified into an annotation group including those lesion candidates that are different from lesions identified with certainty, i.e., a group different from the groups of safely identifiable lesions and uncertainly identifiable lesions).

In the case of X-ray or ultrasound, or in CT and MRI imaging without a contrast agent, the lesions manifest themselves as differences with respect to the healthy state (see the next two paragraphs). Therefore, in this case we have such a background and the differences with respect to such a background are to be detected. The appropriate abnormal differences (the lesions are such in these cases) can be identified by the system based on the training, on the basis of a training process applying such a “ground truth”—that is, first and second lesion location data packets—as with the above-described case. Non-abnormal differences are also possible (for example, normal tissue modifications/changes at bone fracture healing), the lesions can also be discriminated from these (they can be classified into the group comprising lesion candidates different from a lesion).

Normal and different from normal (abnormal) accumulations and the non-abnormal or abnormal differences appearing in images taken without injecting any material (for example a contrast agent, isotope) can collectively be called structural differences (deviations). Therefore, the latter are distinctly called “differences (deviations)” (exemplary types of these are specified in the next paragraph and elsewhere; they are structural differences that are different from accumulations and occur without injecting any material for facilitating imaging to the patient, the structural differences specific in this a way are for short also called “differences” in this description), while the accumulations and such differences are collectively referred to as “structural differences (deviations)” (this indicates that the differences detected in case of modalities without injecting a diagnostic material are also considered some kind of differences, which can be of many types). In any imaging modalities, the abnormal ones of structural differences are lesions.

Lesions may also originate from enrichment (uptake), from changes of density or other anatomical changes; in many cases the lesion manifest itself as accumulation. However, in relation to CT or MRI images there are no accumulations but rather increased absorption, quality or structure change, intensity change, or a change in the density of hydrogen atoms can be detected. These were incorporated in the notion of “difference” set forth above. Accordingly, the concept of lesion is meant to also cover the differences of this type, in addition to the accumulation-type differences. Lesions can be intrinsic—i.e. essentially originating from inside—or extrinsic—i.e. originating from outside (depending on whether there is no or there is a material facilitating imaging).

According to the above, the NN annotator can be considered a so-called “multi-view” classifier, i.e., it can be implemented applying such (see for example: R. Elizabeth Yancey, *Multi-stream Faster RCNN for Mitosis Counting in Breast Cancer Images* (2020), arXiv: 2002.03781v1, 1 Feb. 2020; A. A. Arnaud et al., *Pulmonary nodule detection in CT images: false positive reduction using multi-view convolutional networks*, IEEE Trans. Med. Imaging 35, 1160-1169 (2016); W. Shen et al., *Multi-scale Convolutional Neural Networks for Lung Nodule Classification*, Inf. Proc. in Med. Imaging 588-599 (2015); A. Teramoto et al., *Automated detection of pulmonary nodules in PET/CT images: Ensemble false-positive reduction using a convolutional neural network technique*, Medical Physics, 43, 2821-2827 (2016)), which is adapted to simultaneously receive multiple inputs. The NN annotator therefore has an output of multiple category, i.e. multi-class (see for example: K. Nakajima et al., Bone scan index: A new biomarker of bone metastasis in patients with prostate cancer, Int. J. Urology 24 668-673 (2017); N. Tajbakhsh et al., *A Comparative Study of Modern Machine Learning Approaches for Focal Lesion Detection and Classification in Medical Images: BoVW, CNN and MTANN*, AI in Decision Support Systems for Diagnosis in Med Imaging, 31-58, (2018)).

The NN annotator is trained separately applying low noise images having good statistics, for example filtered pseudo-LN images that have been annotated by one or more physicians, i.e., the typical accumulations, differences, structures have been annotated and qualified (classified).

In FIG. 2, therefore, the connection diagram and the training process of the NN annotator unit 200' are illustrated. According to the above, the annotator unit 200' can have multiple inputs (multi-view); the output of the network being the annotated, i.e., segmented and classified (multi-class) regions corresponding to the filtered image, which is compared during the training with the images segmented and classified by physicians (calculation of the loss function).

During the training process, the parameters of the neural network are adjusted utilising a suitable algorithm (for example, a back-propagation algorithm that is adapted to feed back the changes of the loss function) such that the synthetically generated annotated (segmented and classified) regions are as similar to the physician-annotated images stored in the training image database (i.e. training images, cf. the comparisons applied in the embodiment of FIGS. 3A-3B) as possible.

In the embodiment according to FIG. 2, therefore, in the course of the annotator unit pre-training corresponding to operational step S225, training of the annotator unit is performed by means of an annotator unit pre-training loss function corresponding to the training, after performing the following steps multiple times:

- by means of the annotator unit 200 (more precisely, in FIG. 2 the NN annotator unit 200') generating an annotated pre-training image 230 based on an annotation input training image 205,
- generating (composing) a second difference result by comparing the annotated pre-training image 230 and an annotated training image 235 corresponding to the annotation input training image 205, and
- in the annotator unit pre-training loss function a term being dependent on the second difference result is applied (during each execution such terms are added to the loss function that are similar to the terms applied during pre-training of the filter unit; in other words: such a term is added to the loss function).

Another important component of the system according to the invention is the unit referred to above as the “auxiliary unit”, which is preferably also implemented by means of a neural network (in an embodiment this is a synthetic lesion generator, this term could be used to refer to this unit basically during the training, for self-verification performed by the unit during training, and, in case e.g. the examination protocol is modified, it may serve for performing testing and verification during trans-training).

To implement this component, a modified Generative Adversarial Network can be applied (“GAN,” see: https://machinelearningmastery.com/what-are-generative-adversarial-networks-gans/; https://towardsdatascience.com/understanding-generative-adversarial-networks-gans-cd6e4651a29; I. J. Goodfellow et al.: Generative Adversarial Networks, arXiv: 1406.2661v1, 10 Jun. 2014). Other known technical approaches, for example a Variational Autoencoder system can also be applied for the same purpose (see below).

The training and the structure of the auxiliary unit are illustrated in respective embodiments in FIGS. 3A and 3B. Basically, the embodiments described below are illustrated applying accumulations, but they can of course be generalised for the general case, also in line with that abnormal accumulations are lesions.

In FIG. 3A an embodiment of the auxiliary unit, illustrating the training process is shown. Based on a noise vector (for example, it starts from a random noise image), the generator subunit 350*a* of the auxiliary unit generates new (abnormal) images having disease (which contain abnormal accumulations) for the healthy images available to it as an input (on which only normal accumulations, i.e. accumulations contained in scans of healthy subjects can be seen).

The training process illustrated in FIG. 3A is carried on until the generated images cannot be distinguished by the NN-discriminator (trained together with the generator subunit) from the set of lesion-comprising images selected by physicians (an alternative term for the neural network-implemented discriminator subunit 375*a*).

In FIG. 3A, therefore, a generator subunit 350*a* of the auxiliary unit in this embodiment receives the images labelled (qualified) as "healthy", and for each input image it generates a respective abnormal accumulation layer (in general: a respective lesion image).

In the embodiment of FIG. 3A the following training-related steps can be observed: In the present embodiment the auxiliary unit comprises a first generator subunit 350*a* that, as shown in FIG. 3A, is preferably also implemented by a neural network. The noise vector is provided to the generator subunit 350*a* by a noise input 305 (RND unit). The generator subunit 350*a* also receives healthy medical training images 310 as an input (in an alternative term, healthy images selected by a physician), for which it generates as an output a first image 315 constituting the only abnormal accumulations layer (in the joint training, this output is transferred by the auxiliary unit towards the ROC unit, i.e., it is an auxiliary lesion image, see below), and also the abnormal pseudo image 320. During training, the NN discriminator subunit 375*a* receives both abnormal pseudo images 320 and abnormal medical training images 335 (in an alternative term, abnormal images selected by physicians)—for example, expediently one of them in a random manner, and is trained on the basis of these.

In the course of the training process, reward and penalty can be characterised as follows. The discriminator subunit 375*a* (i.e., according to FIG. 3A the neural network implementing it) have to decide if the generated image (abnormal pseudo image 320) can originate from the database of abnormal medical training images 335 or not. According to the (GAN-type) training described above, if a given image really originates from this database and the discriminator subunit 375*a* decided that it is original, then it is rewarded (for example +1 to the output of the loss function), if it says that it is a generated image (i.e., it is one of the abnormal pseudo images 320 originating from the generator subunit 350*a*) but in reality it is not a generated image, then it is penalised (similarly, e.g. −1 added to the loss output; see also below the related possibilities), and vice versa: what is important is that it should correctly guess the origin of the image fed to it at a given stage of the training process. In other words: it is known if the discriminator subunit was given a real abnormality image or a generated one. Training is carried on until it does not miss any more, i.e., the generator and discriminator subunits are trained together.

The information included in the loss function is utilised for further training of the generator subunit 350*a* and the discriminator subunit 375*a* (this means that there is a returning arrow leading from the decision unit 330 also to the discriminator subunit 375*a*). This is illustrated in FIG. 3A by an auxiliary unit pre-training operational step S325 which corresponds to training implemented by the back propagation, and includes further training of the discriminator subunit 375*a* (although in FIG. 3A it is only possible to denote the information feedback with a reference sign; for more details on the operational step S325 and the loss function see also below).

Thereby, the discriminator subunit 375*a* will get better and better in discrimination making the job of the generator subunit 350*a* ever more difficult, while the generator subunit 350*a* will also improve its generation performance as it "intends" to generate output that is as difficult to discriminate as possible. In such a way, the generator subunit 350*a* and the discriminator subunit 375*a* essentially compete with each other, allowing both to achieve good performance.

According to FIG. 3A, therefore, training of the components of an embodiment of the auxiliary unit, i.e., the generator subunit 350*a* and the discriminator subunit 375*a* is performed, ensuring that these components can be thereafter applied during joint training (see FIG. 4) and during the use (see FIG. 5). The discriminator subunit 375*a* performs binary classification (or makes the classification binary during the use applying a threshold value, see below), i.e., it outputs if the given abnormal pseudo image 320 can be discriminated from the abnormal medical training images 335 (see a first decision unit 330: true or false).

After completing the pre-training illustrated in FIG. 3A, the components of the auxiliary unit are not trained further; rather, the pseudo images generated by—an embodiment of—the generator subunit are applied during joint training (see the joint training illustrated in FIG. 4 that shows how the pseudo image 515 generated by the auxiliary unit 300 and the lesion image 517 are applied therein). And, during the operation of the system, an embodiment of the discriminator subunit is applied (for more details see below in relation to FIG. 5).

Accordingly, it can be seen that the final output of the generator subunit 350*a* after its training has been completed will be a pseudo image 320 applicable on its own (so also for joint training), as well as an image 315 corresponding to the layer of abnormal accumulations (the purpose of the latter is to illustrate that it is also generated as an output, but it does not play a role in the training illustrated in FIG. 3A). The output of the trained discriminator subunit 375*a* will be a binary classification result (i.e., true in view of discriminability—can be discriminated/false—cannot be discriminated), to the application of which in use we shall return later on.

In accordance with the typical course of the training process, the output of the auxiliary unit is medically validated, i.e., humans with appropriate expertise (for example, physicians) verify if the generated images are acceptable (appropriate). Thereby, the validating physician is also able to verify whether the generated pseudo images are appropriate for the purpose (whether they have been synthetized with appropriate—believable—contents, and whether the accumulation layer (i.e., the lesions) has been correctly separated (therefore, it will not go unverified also in this embodiment, either, whether the accumulation layer has been correctly separated).

The physician performing validation validates the entire output, i.e. the processing unit and the annotator. Validation is a part of the pre-training process and a customary verification step; thereby medical expertise is "injected" into the trained system. Injecting medical expertise in all components ensures that the system is robust and can be transtrained. However, after joint training, checks are performed only on a "sampling" basis, for example in case of critical images.

It is also of utmost importance from the aspect of its applications in the invention that in the present embodiment the components of the auxiliary unit are trained together (they have an effect on each other during the training process in an essentially cyclical manner illustrated in FIG. 3A), this common training lends uniformity to the application of the generator and the discriminator subunits.

In another embodiment illustrated in FIG. 3B, a special GAN approach neural network generates new diseased images, which at the end of the process are inseparable (see NN discriminator-A, or in other words a first assistant discriminator subunit 375*b*' implemented applying a first—"abnormal"—neural network that is adapted for checking this) from the abnormal images that had been selected by physicians, i.e., images comprising accumulations/structures different from normal. Together with that it also generates a layer image that, when subtracted from the generated abnormal image, will result in an image that by the end of the training process cannot be discriminated by the discriminator H-neural network (in other words, a second assistant discriminator subunit 375*b*" implemented by the second—"healthy"—neural network) from the physician-selected images containing only healthy accumulations/structures. The assistant discriminator subunits 375*b*', 375*b*" together form a discriminator subunit 375*b*.

In FIG. 3B, therefore, in another embodiment of the auxiliary unit essentially a special GAN-based approach is applied that comprises two separate discriminator networks corresponding to the "abnormal"-"healthy" distinction present in the present medical application.

Accordingly, therefore, in the embodiment of FIG. 3B the training of the auxiliary unit is performed as follows. Like with the embodiment of FIG. 3A, the noise vector is provided for the second generator subunit 350*b* by the noise input 305 (RND unit; accordingly, in this embodiment the starting point for the generator subunit 350*b* is a noise image, but it can even start from a random real image that it modifies based on a random signal; the noise image or random real image preferably has different content for the generation of each pseudo image, i.e., the starting image is different for each generation), which, like the first generator subunit 350*a*, is implemented in this embodiment preferably utilising a neural network.

Like with the previous embodiment, the generator subunit 350*b* generates two different outputs: a second image 340 corresponding only to the layer of abnormal accumulations (generally: an auxiliary lesion image), and an abnormal pseudo image 345. However, these outputs proceed in a different way compared to the previous embodiment. The abnormal pseudo image 345 is received by a first assistant discriminator subunit 375*b*', while a second assistant discriminator subunit 375*b*" receives the difference between the abnormal pseudo image 345 and the second image 340 corresponding only to the layer of abnormal accumulations, the latter being generated by a difference-calculation unit 355.

Accordingly, a further difference is that in the first assistant discriminator subunit 375*b*' the input is compared to physician-selected abnormal medical images 335 (the image database applied in the embodiment according to FIG. 3A can be applied as indicated by the reference sign—images 335—but in principle another image database can also be utilised, this latter is the training image database), however, in the second assistant discriminator subunit 375*b*" the input is compared with physician-selected healthy images 310 (because by calculating the difference a content essentially corresponding to a healthy image is obtained; the description above related to the images 335 are also applicable to that). According to the above, it preferably receives a generated image, or an image from a database of images 310, 335, and it has to find out the origin of the images (the discriminator subunits 375*b*', 375*b*" can be trained applying the above-described reward-penalty principle).

Regarding the outputs of the assistant discriminator subunits 375*b*' and 375*b*", a binary—or probability-based but converted to binary—classification is performed by means of first and second decision units 330', 330", providing feedback to the assistant discriminator subunits 375*b*', 375*b*" and the generator subunit 350*b*, respectively (the latter is illustrated in FIG. 3B by fifth and sixth operational steps S425', S425" corresponding to training implemented by backpropagation, which are also meant to include the feedback from the decision units 330', 330" to the generator subunit 350*b* and to the assistant discriminator subunits 375*b*', 375*b*", noting that—like in the cases described above—in relation to the training process only the information feedback can be denoted in the figure).

The generator subunit (in the present embodiment, a generator subunit 350*b*) and the discriminator subunit (in the present embodiment, a discriminator subunit 375*b* constituted by the assistant discriminator subunits 375*b*', 375*b*") are therefore trained together also in this embodiment. As the outputs of the generator subunit 350*b* there can be seen a pseudo image 345 applicable for the joint training process, and an image 340 corresponding to the layer of abnormal accumulations (i.e., comprising—like other such images—only abnormal accumulations). During joint training and also during use, the corresponding embodiments of the generator subunit and the discriminator subunit can be utilised independently of each other, that is, the appropriate component can be used in order to achieve the desired output (in the joint training, pseudo images and lesion images, during use the output of the discriminator subunit, for details on the latter see below).

The neural network preferably applied in the auxiliary unit therefore comprises two or more joint trained neural networks. One of them is a NN generator that produces, based on a random number (RND) generator, a completely novel image corresponding to abnormal accumulation, and a layer image comprising the accumulations. The operation of this unit is verified (i.e., as mentioned above, validated) by physicians such that it can be made sure that accumulations are not introduced in an anatomically and physiologically unreal manner. An important property of the images generated in such a manner is that the distribution of the abnormal accumulations according to location, intensity, size and shape conforms to the distribution of the abnormal accumulations selected by physicians. Furthermore, such solutions also exist, for example "parametrised GAN,"

wherein the intensity and location of the different from normal accumulations can be adjusted as a function of the parameter.

According to the GAN approach, the training image database is selected by physicians and its performance is preferably verified by a team of physicians (i.e., it is validated; see above, for example the images are individually evaluated by a minimum of three physicians, who compare their expert opinion and form a consensus).

As it was touched upon above, GAN-based synthesisation of medical images is a known possibility (see Samuel G. Finlayson, *Towards generative adversarial networks as a new paradigm for radiology education*, arXiv: 1812.01547v1, 4 Dec. 2018). The images generated in this manner can be utilised for extending the training database of other neural networks, and for making the training process more stable (avoiding overfitting, improving accuracy; M. Frid-Adar et al., *GAN-based Synthetic Medical Image Augmentation for increased CNN Performance in Liver Lesion Classification*, Neurocomputing Volume 321, 10 Dec. 2018, pp. 321-331). It is noted again, however, that adapting GAN as a tool for pre- and joint training as included in the present invention is not known.

With reference to the above, the steps of the methods in the embodiment related to FIGS. 3A-3B are set forth below.

In the embodiment according to FIG. 3A, in the course of the auxiliary unit pre-training corresponding to step S325, training of the generator subunit and the discriminator subunit of the auxiliary unit is performed by means of a generator subunit pre-training loss function (corresponding to the training) and a discriminator subunit pre-training loss function (i.e., these will be used for training the generator subunit and the discriminator subunit) corresponding to the training, after performing the following steps multiple times:

first auxiliary pre-training pseudo images 320 are generated by means of the generator subunit 350*a* based on a noise input 305 by the help of healthy medical training images 310, by means of the discriminator subunit 375*a* inputting out of first auxiliary pre-training pseudo images 320 or abnormal medical training images 335, a discriminability test determining a discriminability result is performed, then, by investigating correctness of the discriminability result, an evaluation result about it is determined (i.e., checking whether the decision of the discriminator subunit has been correct), and in the generator subunit pre-training loss function and in the discriminator subunit pre-training loss function a term being dependent on the evaluation result is applied (the evaluation result is illustrated below; of course the evaluation result can be not only +1/−1, these values are included here only for illustrating the reward/penalty scheme; other constants and continuous results can also be applied, see also in the following paragraphs; the considerations included here and in the previous paragraph also apply—mutatis mutandis—to the embodiment of FIG. 3B).

It can be advantageous in the loss function during the training, if the output which is receive during the training in the term that is dependent on the evaluation result is continuous. It can be said that the discriminability result is continuous between e.g. −1 and 1 (or is a continuous response that can be mapped—for example by a linear transformation—unambiguously to this domain; the parameters of the domain, such as its extension and end points, can be chosen freely). When the range limits specified above are selected, the values +1 and −1 correspond to the options "it is certain that it cannot be discriminated" and "it is certain that it can be discriminated", respectively. In this case, the threshold value corresponding to discriminability can for example be 0.

This continuous value can also be carried over to the evaluation result, i.e. in the course of the training process it can be established whether the discriminator subunit provided a correct result (with a given probability) or it missed (with a given probability), that is, whether it guessed correctly the source database of the given training image; and, corresponding to a correct/incorrect guess, the reward or penalty is carried over—optionally weighted by the continuous result assigned thereto—into the loss function. Therefore, preferably, probabilities can also be taken into consideration in the training and, thus, also during use, and the approach based on continuous probabilities can be turned into a binary one with the help of the threshold value. This kind of training will effectively enable the discriminator subunit to decide on discriminability from the images of the training database (which have been virtually "built in" the discriminator subunit) during the use of the system.

In the system according to the invention, the discriminator subunit is preferably adapted for issuing a discriminability warning in the case of a discriminability result corresponding to discriminability.

Based on the above it can be assessed when the discriminability result accompanies the discriminability, i.e., when a discriminability warning should be issued during use:

if the discriminability result is +1 or another constant, then one of them, for example −1 corresponds to the discriminability;

if, on the other hand, the discriminability result can have a continuous value over a domain, then it is determined by a threshold value (see above; this can be called a discrimination threshold value) whether there is a discriminability, the subdomain corresponding to discriminability is separated from the subdomain corresponding to non-discriminability by the threshold value (for example, discriminability persists below the threshold value).

Also, in line with the GAN analogy, the above can be summarised by maintaining that the generator and discriminator subunits are trained according to the GAN approach. In this framework, the result given by the discriminator subunit can be discrete or continuous, and in the continuous case a suitably chosen threshold value can be assigned to it in order to specify (to establish region boundaries) that the discriminability result corresponds to discriminability or not. After the training of the system has been completed, the discriminator subunit can be applied during use (operation) utilising this threshold value.

In general, therefore, it is the GAN framework that determines what kind of discriminability result (for example, discrete or continuous) is given by the discriminator subunit, and also the manner in which the correctness of the result is investigated, i.e., how the evaluation result is determined during pre-training for the pre-training loss function.

The discriminability result specifies whether the discriminator subunit has found the received input to be discriminable from the abnormal medical training image. According to the above, it is possible to investigate the correctness of this, because due to the applied training (training process, training plan) we have information on (i.e., we know) the type of the image, i.e. from which database it originates (comes) that was fed to the discriminator subunit (i.e., whether it was able to correctly guess that the pseudo image was a pseudo image, and that the abnormal medical training image was not a generated image), that is, based on the images applied for the training, the correctness investigation can be performed on the result given by the discriminator subunit during training. Based on that, it is possible to determine the evaluation result, i.e., if the decision of the discriminator subunit was correct, and the subunit can be rewarded or penalised accordingly (in the example above the reward and penalty was interpreted as +1 and −1 for the sake of illustration).

In addition to the above, in the embodiment according to FIG. 3B this is applied for a system which comprises an auxiliary unit which has a discriminator subunit 375*b* configured by a first assistant (auxiliary) discriminator subunit 375*b*' and a second assistant (auxiliary) discriminator subunit 375*b*", and in the course of the auxiliary unit pre-training corresponding to operational step S425 realized by operational steps S425' and S425", training of the generator subunit, the first assistant discriminator subunit and the second assistant discriminator subunit of the auxiliary unit is performed by means of a generator subunit pre-training loss function, a first assistant discriminator subunit pre-training loss function and a second assistant discriminator subunit pre-training loss function corresponding to the training, after performing the following steps multiple times:

second auxiliary pre-training pseudo images 345 and auxiliary pre-training lesion images 340 determined by a first lesion location data packet corresponding thereto is generated by means of the generator subunit 350*b* based on a noise input 305 (this noise input may differ from the noise input applied in FIG. 3A according to which the generator subunit 350*a* also receives the healthy medical training images 310; based on this, the generator subunits 350 and 350*b* can be distinguished from each other; the noise inputs shown in FIGS. 3A and 3B may also be identical but these may be processed differently by the generator subunits 350*a* and 350*b*), by means of the first assistant discriminator subunit 375*b*' inputting out of the second auxiliary pre-training pseudo images 345 or abnormal medical training images 335, a discriminability test is performed determining a first discriminability result, and by means of the second assistant discriminator subunit inputting differences generated (obtained, composed) by subtracting from the second auxiliary pre-training pseudo images 345 the corresponding respective auxiliary pre-training lesion images 340 (this difference can be obtained if a first lesion location data packet corresponding to the pseudo image is available in image representation, i.e., a lesion image is available; see the discussion on the auxiliary lesion images that are of the same type as the present pre-training lesion images—which are applied for pre-training—because the generator subunit of the auxiliary unit is trained for generating such images) or inputting healthy medical training images 310, a discriminability test is performed determining a second discriminability result, then, by investigating the correctness of the first discriminability result and of the second discriminability result, a first evaluation result and a second evaluation result is determined about them, respectively, and, in the generator subunit pre-training loss function respective terms being dependent on the first evaluation result and on the second evaluation result are applied, and in the first assistant discriminator subunit pre-training loss function a term being dependent on the first evaluation result is applied, and in the second assistant discriminator subunit pre-training loss function a term being dependent on the second evaluation result is applied.

In the discussion above, the word "pre-training" included in the name of the first and second auxiliary pre-training pseudo images indicates that these pseudo images are also applied for training the generator subunit during pre-training, i.e., the content of these images is still flexible because the unit generates them is in the process of continuous learning (for example in a manner illustrated in FIGS. 3A and 3B). The attribute "pre-training" is applied for distinguishing these images from the above-mentioned joint-training auxiliary pseudo images which—after the completion of the auxiliary unit pre-training process—are generated for joint training applying the generator subunit that has accordingly already been subjected to auxiliary unit pre-training (and is not to be trained further). The attribute "auxiliary" in the name of the pre-training pseudo image serves for preventing these names from being mixed up with the names utilised with other pre-trainings (the first and second auxiliary pre-training pseudo images are applied in auxiliary unit pre-training).

In the present description, these attributes are not necessarily included (used) when pseudo images are mentioned, because the stage at which the pseudo images in question are utilised can be established from the context.

Figure 7:
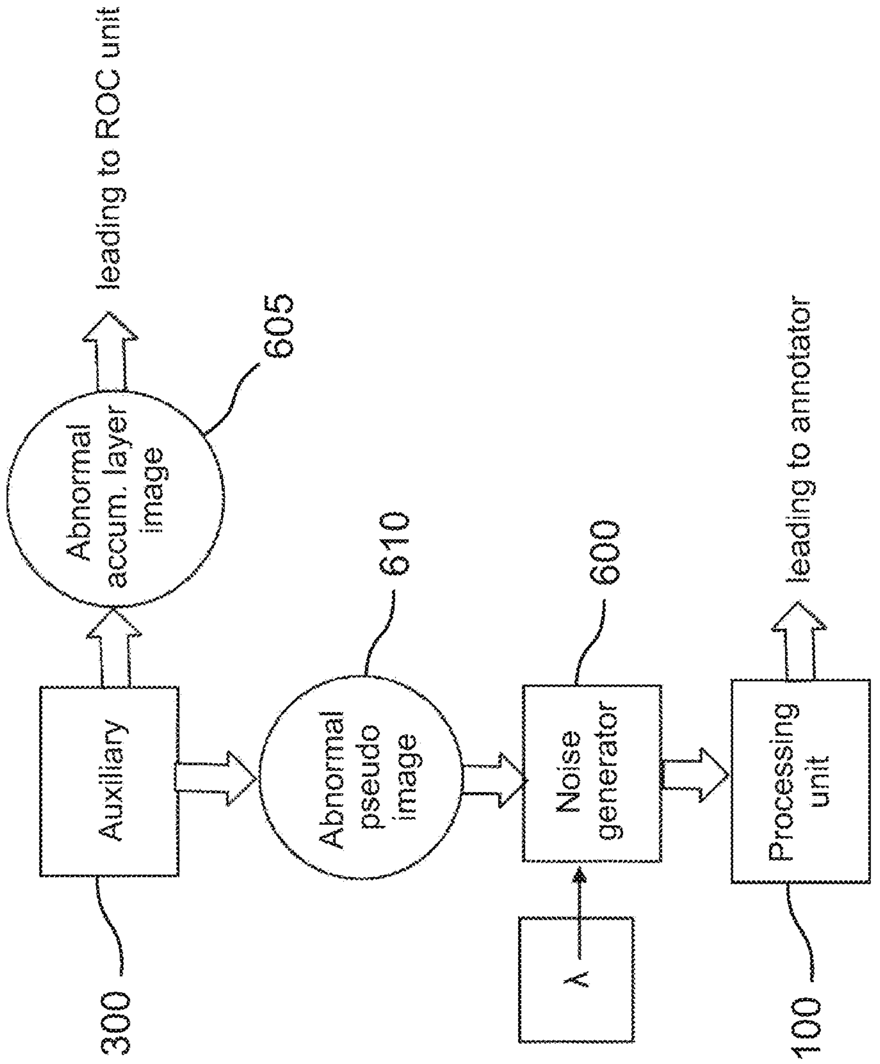
FIG. 7 is a flow diagram illustrating reduction proportion checking in an embodiment.

In the following, fitting (matching) to each other the preferably applied components of the system according to the invention introduced above (filter, annotator, auxiliary unit) will be described. Thus, in the first stage of the training process these components are trained as stand-alone (separate) components. Thereafter, the components are interconnected to form a system that preferably allows:

performing a ROC analysis—which can be considered automatic—of the system (this is carried out by means of the ROC unit, according to which we can conclude about the diagnostic value based on the AUC parameter);

optimising the parameters of each network based on a diagnostically relevant measure (i.e., the AUC parameter);

establishing the degree by which the activity/the measurement period can be reduced while preserving the diagnostic performance of the system (see the descriptions related to FIG. 7);

assuring the continuous quality of the diagnostic imaging system (complying with FDA [US Food and Drug Administration] while keeping the costs as low as possible.

FIG. 4 illustrates an embodiment of the system according to the invention focusing on the process of training (manner or training). The encircled portion (i.e., the major components are encircled) in the top left part of FIG. 4 illustrates, in an embodiment, the system components related to training (training system components), reflecting that the focus of FIG. 4 is on training. As it was referred to above, about some of these system components (such as basically the annotator unit 200 and the ROC unit 500) it can be decided whether these should be a part of the system that is deployed after training to an end-user location.

In an embodiment, the system prepared, i.e., trained in such a manner—both the system comprising training system components and the system deployed to the end-user—can be called a "DRONES: Deep ROC-Optimized Neural Network System"; in the relevant embodiment, furthermore, the joint training process—that is, the training after the pre-training, where the ROC control is included—can be called "DRONES training".

An embodiment of the system after the training is illustrated in FIG. 5 in operation (i.e. after the training method has been completed, when the system can be considered trained).

FIG. 4 illustrates a further key component, a ROC unit 500, which plays a role in the training method, and in other embodiments also in operations related to the reduction parameter and in treating the novel input images.

We will now describe the training process illustrated in FIG. 4. FIG. 4 illustrates the joint training, the steps and operations related thereto, that is, the training steps carried out subsequent to the pre-training of individual components. This process is indicated by arrows in FIG. 4 (the feedback of the AUC parameter is indicated by hatched arrows).

The joint training is performed applying pseudo images 515 originating from the auxiliary unit 300, for which a respective lesion image 517—for example, an accumulation (layer) image—corresponds (see the outputs of the generator subunits 350*a*, 350*b* in FIGS. 3A, 3B from which these two types of images can be received separately). The lesion image 517 is transferred to the ROC unit 500 (for related aspects see also below).

During the joint training, the entire pseudo image 515—which also comprises information related to the accumulations (generally, lesions) which are also available separately, see FIGS. 3A-3B—is transferred to a processing unit 100 that generates a processed image 520 corresponding to the pseudo image 515 and transfers it to an annotator unit 200. Based on the processed image 520, the annotator unit 200 generates an annotated image 540 that constitutes, on the one hand an output (cf. annotation result dataset), and on the other hand it is also transferred—typically in a more abstract form—to the ROC unit 500 in the course of joint training for a comparison with the lesion image 517 (which is the image representation of the first lesion location data packet), such that a comparison between the first lesion location data packet corresponding to the latter and the second lesion location data packet corresponding to the annotated image can be performed as set forth above.

Based on its inputs (in the embodiment, a lesion image 517 and data corresponding to the second lesion location data packet) the ROC unit 500 determines, for each of the lesions contained in the lesion image 517 and for every image contained in the training image database (these are pseudo images 515 of the joint-training generated by the auxiliary unit 300), if the given lesion has been recognized by the annotator unit 200 or not.

Based on this it counts how many of the lesions it has failed, i.e., determines the true positive rate and the false positive rate, which specify one or more points of the ROC curve. For example, more than one points can be specified if the classification unit is able to discriminate the characteristically imaged lesions and uncertainly identifiable ones using a scale with two or more elements (i.e., giving a discrimination probability).

In case the investigated image is a 3D image, then the accumulations (generally: the structural differences) may not only be represented in 2D, but may also have a three-dimensional location; however, utilising appropriate coordinates they can similarly be identified, i.e., the analogy of the 2D images can be easily extensible to 3D images.

A study (Julian B. Tilbury et al. entitled "*Receiver Operating Characteristic Analysis for Intelligent Medical Systems—A New Approach for Finding Confidence Intervals*", IEEE TRANSACTIONS ON BIOMEDICAL ENGINEERING, VOL. 47, NO. 7, July 2000) describes a method, based on which the ROC curve can be estimated with a confidence interval based on a single point. This enables the calculation of the AUC.

Therefore, the ROC unit 500 receives the second lesion location data packet from the annotator unit 200 and, with the lesion image 517, also the first lesion location data packet, based on which it updates the AUC parameter and feeds it back to the processing unit 100 and to the annotator unit 200. This feedback scheme is illustrated in FIG. 4 by a first operational step S523 (indicated by the arrow pointing from the ROC unit 500 to the processing unit 100), and a second operational step S527 (indicated by the arrow pointing from the ROC unit 500 to the annotator unit 200); this feedback is preferably built into the loss function, as it will be demonstrated below in an example in the description of the Lagrange-multiplicator approach. This training stage is called "joint training" because of the simultaneous feedback and training; however, in accordance with the term "pre-training" it could also be called "post-training."

The value of the AUC parameter that is to be inserted in the formula of the loss function (see formula (2) below) is calculated preferably after passing through the system an epoch of the pseudo images (an "epoch" refers to all the training images were included in the training, this is typically a few thousand images, for example between 500 and 10000, particularly between 500 and 3000 images can be contained in an epoch).

With the help of the loss function—i.e., whether it displays an improving or deteriorating tendency based on the epoch (the given cycle)—we change the parameters of the neural network, and then feed the pseudo images to the system, expecting that the network "converges", i.e., the value of the loss function becomes smaller, which means that the AUC also converges toward a maximum (it is penalised, if it goes to the wrong direction).

In the conventional training methods, there exist means for stopping the training process (see the reference below to stopping the training process on the basis of test sets). Accordingly, the followings can be utilised for stopping the training method (i.e., to determine that an optimum of the AUC parameter has been reached, or we are so close to an optimum that it is not worth to continue training):

In the course of examining the AUC values, if signs indicating convergence are detected, the system is applied—at an appropriate point of the method—to a so-called testing set (see the study mentioned above; J. K. Terry et al.: Statistically Significant Stopping of Neural Network Training, arxiv: 2103.01205v3, 28 Jul. 2021).

The testing set is constituted by such images that allow us to measure the accuracy of the system (see also the reference above). If the application of the testing set does not result in sufficient accuracy, then the joint training is carried on; however, if a sufficient accuracy is reached by applying the testing set, the joint training process is stopped.

Of course, the goal of joint training is that the AUC parameter corresponding to the trained system is as high as possible, i.e., as close to 1 as possible. In our experience, by applying the training method according to the invention, sufficiently high values can be reached.

Figure 6:
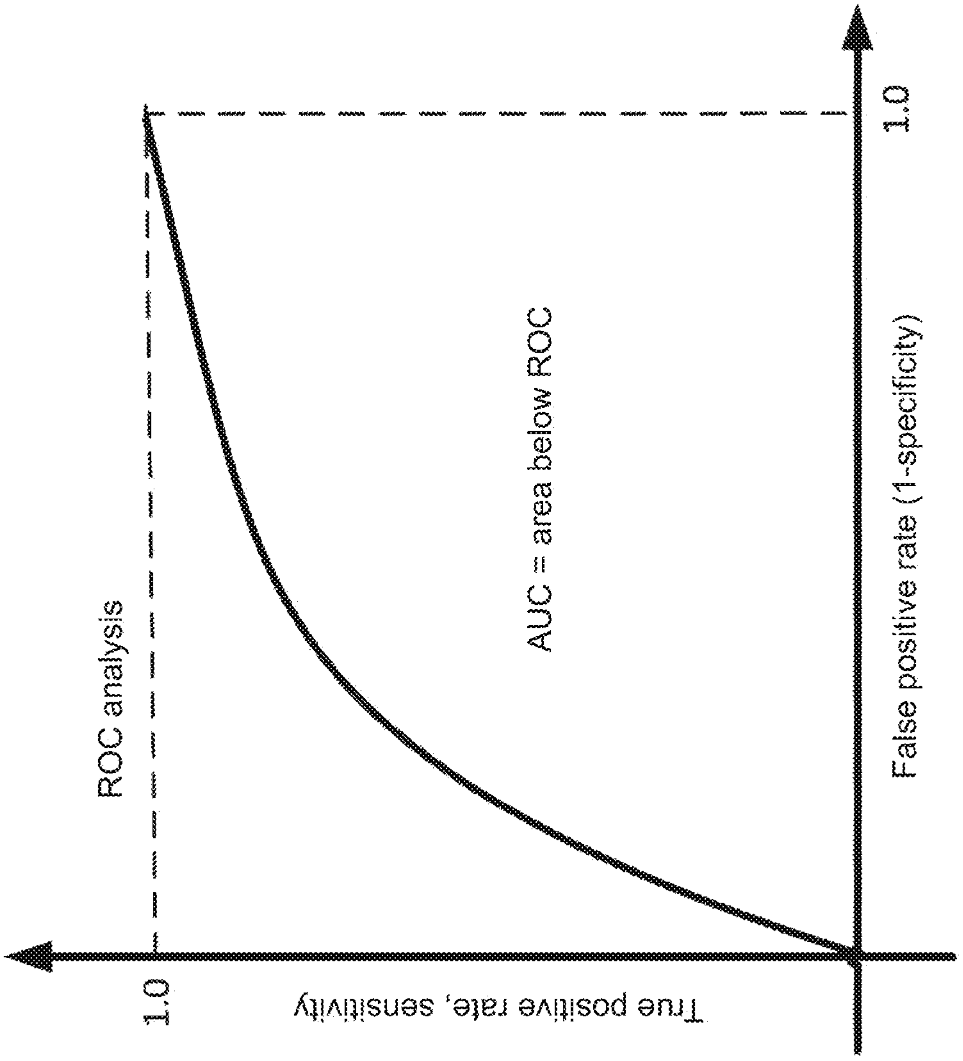
FIG. 6 shows a graph related to the operation of the invention.

Referring to FIG. 6, the followings are given about the operation of the ROC unit.

The ROC unit receives the auxiliary lesion image (see a lesion image 517 in FIG. 4) with the lesion locations, and also receives lesion location information also from the annotator (second lesion location data packet), and then compares these. The ROC unit has a task to examine how the processing and annotator units have worked, utilising the auxiliary lesion image initially generated as "ground truth".

Based on the comparison, one or more points of the ROC curve are obtained after an epoch of pseudo images is completed. In relation to that, reference is made to the introduction where the definition of the quantities indicated in FIG. 6 beside the axes of the ROC curve was given. The quantities included therein (TP, FP, TN, FN, which are probabilistic quantities) can be derived from the applied comparisons (since the "ground truth" is available, the rate of "true/false" cases and "positives/negatives" can be determined). Based on this single point, the ROC curve can be fitted (the ROC curve passes through the origin), and the confidence of the fitting can also be determined (see also: Julian B. Tilbury et al., *Receiver Operating Characteristic Analysis for Intelligent Medical Systems—A New Approach for Finding Confidence Intervals*, IEEE TRANSACTIONS ON BIOMEDICAL ENGINEERING, VOL. 47, NO. 7, July 2000.).

After the epoch has been completed, the integral of the ROC curve obtained this way is calculated, which gives the AUC value. This value will be between 0 and 1, closer to 1 (the value we aim to reach) if the curve increases steeper. If the system behaved perfectly (ideally), then at 0 (false positive=0) the ROC curve would jump to 1 (true positive=1), so its integral would be AUC=1. In this ideal case, therefore, it would hold true that, depending on the sensitivity parameter, the system will avoid fails, i.e., that its decisions—be they positive or negative—will be accurate in each case.

After the processing of the epoch by the ROC unit 500 is completed, the processing unit 100 and the annotator unit 200 therefore receive the AUC parameter value and it is taken into consideration in the respective joint-training loss functions (local loss functions).

In accordance with the training, the value of the loss function is characteristic of the performance of both the processing unit 100 and the annotator unit 200, i.e., of the quality of the results output by these units (relative to the ideal result, i.e., relative to the so-called "ground truth"; cf. t the first term in formula (2) of the loss function below, and the disclosure about the effect joint training has on this term).

By applying feedback of the AUC—i.e., by including a term dependent on the AUC parameter—this evaluation is complemented by how much the units were able to approximate the AUC value to 1 in the given cycle with their performance (how much the value (1−AUC) has decreased), i.e., with increasing performance the value of the AUC parameter dependent term of the loss function decreases. In other words, in each cycle the system goes over all training images (i.e., the epoch of pseudo images) after being trained further utilising a Lagrange-multiplicator penalty term that already incorporates the updated AUC value.

The output of the ROC unit 500 shown in FIG. 4, i.e., a ROC report 550 is adapted for making sure about the system's performance from a clinical aspect. The ROC report 550 is prepared after the completion of joint training. The ROC report 550 preferably includes the value of the AUC parameter obtained in the course of joint training (optionally it also contains the ROC curve itself, in line with the objective that the ROC curve should approximate the step function as much as possible in joint training) together with the corresponding confidence interval (i.e., deviation; in the discussion below on preserving the diagnostic value—see in FIGS. 7, 9A, 9B the branches leading to the ROC unit—this, i.e., the contents of the ROC report obtained at the end of joint training, is used as a reference point).

The training of the system carried out in its interconnected state, i.e., the joint training can also be referred to as DRONES training (see above). Further details are set forth below—in light of the description of FIG. 4 above—in an approach based on the filter 100' illustrated in FIG. 1, and the annotator unit 200' shown in FIG. 2; the above-specified terms identifying these are also used in some cases below.

During the joint training, the image provided with pseudo abnormal accumulations generated by the NN-auxiliary unit (implemented in this embodiment with a neural network) is passed through the NN-filter and the NN-annotator, and then the lesions detected and classified by the NN-annotator are compared with the lesion image generated by the NN-auxiliary unit (a comparison of the first and second lesion location data packet is performed, see also in the above definition of the invention). From this, the ROC unit generates the ROC curve together with its confidence interval (this is an important mathematical tool applicable for ROC analysis, enabling the drawing of ROC curves based on a true positive-false positive pair together with the corresponding confidence interval; see: Julian B. Tilbury et al., *Receiver Operating Characteristic Analysis for Intelligent Medical Systems—A New Approach for Finding Confidence Intervals*, IEEE TRANSACTIONS ON BIOMEDICAL ENGINEERING, VOL. 47, NO. 7, July 2000.), and it also generates the AUC parameter to be optimised, which is the integral of the ROC curve (see FIG. 6).

The AUC parameter is a real number between [0, 1] that is applicable for measuring the clinical value of the images (John A. Swets, *ROC Analysis Applied to the Evaluation of Medical Imaging Techniques, Investigative Radiology*, vol 14, p 109, (1979)). In course of the joint training, we aim at maximising this AUC parameter by modifying the NN-filter and the NN-annotator. In addition to that, it is also important to ensure that each of the component networks also do not deviate significantly from their operating point.

In the following, an implementation of the joint-training loss function for the processing unit (more particularly, filter unit) is described.

A possible but not exclusive implementation (solution) of joint training that ensures the above can be constructed of as follows: the AUC value generated by the ROC unit is multiplied by an appropriate factor $\beta_{filt}$ (Lagrange multiplier) and is added to the loss function of the internal networks (that preferably implement the processing unit and the annotator unit). For example, applying the L2-metric in the case of the NN-filter, in this embodiment the two terms of the modified loss function ($L_{filt}$), i.e., the processing unit joint-training loss function are the following:

$$L_{filt} = \sum_{k=1}^{all\ images} \sum_{i=1}^{all\ pixels} (PseudoLN_{k,i} - LN_{k,i})^2 + \beta_{filt}(1 - AUC) \quad (2)$$

where PseudoLN is the filtered image output by the NN-filter (the reason for this denotation is that, as it was mentioned elsewhere, the image synthesised by the filter unit can be called a pseudo image; the contents of this image will change according to the changes of the filter machine learning unit trained further during joint training, see below) while LN is its low-noise counterpart with which it was compared during pre-training (i.e. the comparison image applied for training, which in this case is naturally noisy, i.e. is burdened with low noise, therefore this is a so-called noise-to-noise type training).

Of course, the different networks (the formula (2) above generalised for a processing unit, as well as the network corresponding to the annotator unit) have different multiplicators β and can be derived in a similar way. It is also noted that instead of the L2-metric applied above, the L1-metric or other metrics can also be applied also in this case.

The metric determines how a scalar value is obtained as a loss function value on the basis of the difference between two images—in this specific case, the input applicable as "ground truth" and a different image synthesised by the machine learning unit, for example a neural network. It is therefore applied for characterising how close the two images are to each other. Accordingly, several functionals $I(\text{image}_1, \text{image}_2)$ with such a mapping are appropriate for this task; typically, the L1- or L2-metrics are applied.

On the calculation—during the joint training—of the first term of $L_{filt}$ above the followings are noted. The value of $L_{filt}$ is utilised in the training step applied during joint training. Accordingly, the machine modules (generally, the machine learning units implementing the processing unit and the annotator unit) still undergo learning, undergo modifications, implying that they typically output a different result for the same input after training than previously. In the pre-training process we applied training image pairs (of which the low-noise image is for example be the $LN_{k,i}$ image in formula (2) above) that by their nature remain unchanged.

At the same time, there is a corresponding image generated by the given machine learning unit (e.g., the image $PseudoLN_{k,i}$ above) for the input image—e.g., in the above example for the high-noise training image—which corresponds to how the given machine learning unit "responses" in its current state to the input image. Because the machine learning unit undergoes continuous learning during the joint training, the content of this image varies from cycle to cycle in the course of joint training.

When, therefore, the value of the joint-training loss function is calculated after each cycle, then—in addition to the AUC parameter value—of course the value of the 1st term containing these images will also change (i.e., essentially the operating point is adjusted, see also below). The change of the 1st term accordingly also indicates that if the performance of the given machine learning unit has already improved as a result of joint training, then the differences included in the function decrease (because the image generated by the machine learning unit is closer to the training image), so, in case we are searching for the minimum of the loss function, as in the formula (2) above, then in case the AUC value improves both terms of the loss function will decrease.

Also, in accordance with the above, therefore, by passing the artificial (pseudo)-images—for which the desired output of the annotator unit is known, i.e. it is possible to perform comparison with the lesion image preferably available as an image representation of the first lesion location data packet—through the joint training we check the behaviour of the AUC parameter, but by applying this term the performance of the individual units (processing unit and annotator) is also controlled.

Therefore, it is meant to be included in the step corresponding to the substitution of the AUC parameter value (see above) that in each of the joint-training loss functions the term to be calculated by a given unit will change according to the current state of the given unit, i.e., according to the state of the unit that was used for determining the actual AUC parameter value.

Therefore, after the epoch has been completed, the current value of the AUC parameter is calculated and the loss function are composed. The generated images included in the loss function are generated applying the state of the (processing/annotation) unit with which the epoch has been completed (this is how the difference first term of the loss function is related to the directly AUC dependent term).

In the case of the first AUC feedback—i.e., after the completion of the epoch corresponding to the first cycle—therefore the images do not change in the first term of the loss function, because in the first joint training cycle the AUC parameter value is calculated using the original state of the processing and annotator units. Having obtained the loss function in this way, training of the processing and annotator units is performed, then after completing the next cycle the subsequent value of the AUC parameter is calculated. Thereafter, in the 1st term of the joint-training loss function the images obtained with the processing/annotator unit state that carries (incorporates) the further training of the first cycle will play a role, the AUC dependent term containing the newer value of the AUC parameter. The subsequent cycles are performed accordingly, until the joint training is stopped (for example investigating whether the training can be stopped by applying the system to a testing set).

By introducing the 2nd term of $L_{filt}$ (the term with AUC) such a "constraint" is switched on that shifts the operating point to a direction where diagnostic value can be expected to be better assured; this latter term is calculated based on the images synthesised by the auxiliary unit (see the calculation of the AUC with the help of the ROC unit). In respect of the operating point, this also holds true for the annotator and the term of it with AUC. Because the AUC parameter value preferably converges to 1, in the state desired to be reached the term with AUC does not significantly move the component networks away from the operating point (constitutes a small perturbation), however, the joint training significantly improves the efficacy of the system by facilitating the preservation of diagnostic value.

Referring to the statements in connection with the invention included above, it is noted that these statements are related to the manner in which the value of the AUC parameter is incorporated into each of the joint-training loss functions.

The joint-training loss function corresponding to the annotator unit can not necessarily be expressed with a closed formula, but at the same time it can be formulated as a suitable algorithm (i.e., can be programmed, see below); those functions that cannot be expressed with a closed formula are also meant to be within the concept of loss function.

There is a physician-annotated training database, on the images of which the locations—for example $X_i$—of the lesions are marked (this is essentially the "ground truth" corresponding to the annotator). This database is applied for pre-training the system. The loss function corresponding to the annotator investigates whether the annotator has found on the raw (not-annotated) image a lesion close to that is marked in the "ground truth". If any of the lesions found at the location $Y_j$ is close to $X_i$ (i.e., closer than a predefined annotator threshold value), then a pair is found, so the loss is decreased. If there are such lesions that have not been found or have been inaccurately classified, or there is any other difference, the loss value is increased. To the loss value derived during joint training (in a manner analogous to the description above related to the processing unit/filter, i.e., the 1st term of formula (2), the further training applied during joint training also affects this base term) another term—depending on the AUC parameter corresponding to the annotator—is added, for example a term with β*(1−AUC) (as with the above, as an additional term added to the loss).

Therefore, in the course of joint training, the processing unit and the annotator unit are trained in an interrelated manner—i.e. interrelated by the help of the AUC parameter value—but applying separate joint-training loss functions. The applied trainings can be called "processing unit joint machine training" and "annotator joint machine training", respectively.

The factor β introduces to the optimisation a constraint boundary condition that is important to us. At the beginning, in course of the pre-training β=0 (in accordance with that the AUC parameter has no role at this time). During the pre-training, the parameter β is preferably chosen according to the value of the remainder term (i.e., in formula (2) above, the portion $(\text{PseudoLN}_{K,i}-\text{LN}_{k,i})^2$, that is, the term(s) other than the term multiplied by the Lagrange multiplier) and to the value of 1−AUC such that the term (1−AUC) can have an effect (for example the remainder term and the term (1−AUC) multiplied by the Lagrange multiplier are the same order of magnitude, considering preferably the values derivable at the start of joint training).

During the iteration it may be expedient to change β continuously (in differentiable manner) in each cycle (i.e., every time the AUC parameter is recalculated) in order that the desired convergence can be ensured. It is expedient to change β using such a scheme wherein an increase in B also gradually increases the constraint. The system originally performs learning on a hypersurface (i.e., a local extremum was found during pre-training); then the term including the constraint with β is switched on with which a large perturbation may be introduced, which may completely alter the hypersurface. Conversely, by gradually increasing β it can be achieved that the surface varies only gradually, whereby the method can remain numerically more stable.

The yield of the AUC can be adjusted by modifying the value of the Lagrange multiplier applied for multiplying (1−AUC). A potential solution can also be maximising multiple variables simultaneously; there exist methods to achieve that, for example the application of such a loss target function that increases either when the term originating from the images or (1−AUC) increases.

The approach using the Lagrange multiplier ensures that the deviation from the operating point is not significant, i.e., the Lagrange-multiplier method has the advantage that by decreasing or increasing the parameter β—either during iteration or between subsequent cycles—the transient process can be regularised, which results in improved numerical stability.

This can also be ensured in alternative ways; to achieve that, the loss function can be replaced by an arbitrary function with the general formula: $L_{filt}=f\,(\text{PseudoLN}_{k,i}, \text{LN}_{k,i}, \text{AUC})$. This formula can be generalised in a natural way for the case wherein a processing unit is included instead of the filter. The function is not necessarily homogeneous for all terms, i.e., the function may include an amplification (for example, fails can be penalised more than correct results are rewarded).

The corresponding loss function is typically such a function (the same construction is to be built for the loss function of the annotator, applying variables that are analogous to this case but correspond to the annotator, and the AUC parameter as a variable also in it) that has a local extremum—for example, minimum or maximum—at the point where AUC=1. Therefore, such a multi-variable function is needed (a three variable function is specified here for the filter, but this can be generalised) of which the partial derivative according to the AUC variable is zero at the point AUC=1, i.e., this is a criterion for selecting the function that can be used for defining a group of functions that can be applied as a loss function in the present case.

With regard to the loss function, the following are noted. In cases similar to the present one, we typically search for an extremum (the optimum i.e., the minimum or maximum: in such approaches this may vary, applying a multiplier of −1 they can be transformed into each other; in the case of a loss function, typically the minimum) of an object function (in an alternative term, a "criterion function"; these general terms could also be used instead of the term "loss function"), thus reaching the solution candidate determined to be the most appropriate (in the present case, the appropriately trained variant of the neural network or machine learning algorithm).

To achieve this, in the case of machine learning algorithms and neural networks typically the error is minimised. Accordingly, in such a case the object function is typically called a loss function, cost function, or error function, but it can also be called a difference function or learning function. Also, the value given by the loss function could be simply called "loss" (see https://machinelearningmastery.com/loss-and-loss-functions-for-training-deep-learning-neural-networks/). The loss function is therefore meant to include all functions applied for training the machine learning unit.

In relation to the comparison of pre-training and joint training, the followings are also noted. According to the pre-training the medical expertise is introduced into all pre-trained units. However, in joint training pseudo images are applied which propagate through the system, and the results can be compared with the "ground truth" (auxiliary lesion images) originating from the auxiliary unit in the ROC unit, i.e., a "backcheck" can be performed there.

Pre-training has essentially been based on visual assessment (for example, in the case of the annotator the physicians' assessment is included in the applied training images), but during joint training the utilisation of a "ground truth" helps make the system's behaviour more objective (thus, the "ground truth" also protects the system against for example the easily misdiagnosed random accumulations that originate e.g. from noise; in this manner these can be detected easily, while they are difficult to recognise by a physician).

In FIG. 4, therefore, the training of the system is illustrated in an embodiment, i.e., the structure and training model of a Deep ROC-Optimized Neural Network System (DRONES) having assured diagnostic value. The filter and annotation neural networks are pre-trained separately (on their own) according to the above (pre-training step), which is followed by training them further as they are interconnected (joint training). The automated testing, i.e., ROC analysis, of the interconnected networks is performed by the ROC unit 500 with the help of artificially generated images, i.e., images generated by the auxiliary unit 300.

An extremely advantageous feature of the solution according to the invention, i.e., a system for aiding evaluation and the training method thereof, is that such images—i.e., images processed and annotated applying artificial intelligence—are obtained as output of which the diagnostic value can be calculated and can preferably also be included in an automatically generated ROC report.

An important advantage of the present invention is therefore that by applying joint further training, in a manner specified above, of the networks corresponding to (i.e., implementing) the processing unit 100 (e.g., NN-filter) and the annotator unit 200 (e.g., NN-annotator) illustrated in FIG. 4, their accuracy and the efficacy of the system can be further improved compared to the case where the individual components are utilised in a standalone but sequentially interconnected manner (without joint training). An operating point is preferably provided by pre-training; applying the above-detailed method it can preferably also be ensured that the system also remains near the operating point after joint training.

In the joint training phase, the parameters of the networks—i.e., the parameters of the NN-filter—are modified, and the filtered images are expected to increasingly assist the operation of the NN-annotator also taking part in the joint training, i.e. the correct classification and also the detection of small-scale accumulations (e.g., the early-stage diagnosis of certain diseases).

In FIG. 4 basically the training process of the system is illustrated, the system being able to operate, thanks to its training, as a system with assured diagnostic value including (comprising) multiple neural networks. Accordingly, the method and system according to the invention address the problem of known systems related to the diagnostic value that was described in the introduction.

FIG. 5 is meant to illustrate the operation of the trained system in such a case where a primary (input) medical image 505 and a (n optional) secondary (input) medical image 510 containing additional information are applied as an input (in FIG. 5, the generator subunit 350 is shown as a part of the auxiliary unit 300, it was not included in FIG. 4 due to a lack of space; as can be appreciated from the description, the training is based on the functionality of the auxiliary unit basically performed by the generator subunit, while during use a functionality of the auxiliary unit basically performed by the discriminator subunit is made use of).

Let us suppose that the secondary image is a SPECT image, more precisely a reconstructed volume. In such a case, separate (standalone) filter (generally: processing unit) and annotation networks must be trained for processing this volumetric information (like with other image information interpreted for example in a plane).

Such a scenario can also be conceived wherein the filter also receives for example a CT or MRI image in addition to the primary planar medical image (that is, the filter has two inputs), so the filter itself is able to also consider the CT structure during filtering the planar image. In an example, this may have the preferable yield that for example in the case of the noisy image of a ribcage (see FIGS. 11A-11D) it will not generate a branching Y-shaped rib (although it may infer the existence of such a structure during training) in the filtered image, because the information contained in the CT image makes it clear that it is not a real anatomic structure. In this case, therefore, the trained processing unit will know where the bones are, and it will search for the bone-specific accumulations typically at such locations. Therefore, it can be maintained that in general the extra information provided by the secondary input improves specificity, i.e., it reduces the fail rate.

In accordance with FIG. 5, in such a case the discriminator subunit 375 receives the primary medical image 505 and also the secondary medical image 510. This subunit must also be prepared for processing both, and of course it has to issue a warning if it detected discriminability in the case of any of them.

In summary, it can be maintained that in case secondary information is available, the system must be prepared for treating such information; however, the system can be easily prepared, thus the secondary information can be utilized.

When the previously trained system is deployed to its place of destination (for example, a hospital), it is applied for measured (i.e., raw) images (recorded from patients), i.e., these images constitute the input of the system, such as the medical images 505 and 510. The process of performing the method applied during use will be described for the primary medical image 505.

The raw medical image 505 is filtered/transformed by the processing unit 100 (here we refer in general to the unit that was implemented as a filter 100' in the above-described embodiment) producing a processed image 620 (a pseudo-LN filtered image), while the annotator unit 200 receiving the latter at its input marks the diagnostically relevant regions, for example the regions exhibiting different from normal accumulations. The output is an annotated image 640 that more effectively aids diagnosis (in the joint training as shown in FIG. 4, a processed image 520 and an annotated image 540 corresponds to (i.e. originates from) the pseudo image 515; during use there are the processed image 620 and the annotated image 640 that already originate from the raw medical image 505 and not from the preferably synthetic pseudo image 515).

Besides that, during the operation of the system the raw medical image 505 is also fed into the discriminator subunit 375 of the auxiliary unit 300 (see also above: into the NN-discriminator network thereof), which due to the pre-training is able to give a signal whether the image of the present measured patient scan (i.e., the medical image 505) significantly differs from the images of the training image database of the auxiliary unit 300 (also including the healthy and diseased images 310, 335), see a decision unit 560, which—in the case of a neural network implementation—utilises a loss test (an example for this can be the reward/penalty scheme described above in relation to FIG. 3A). Like the discriminator subunit, the decision unit 560 performs a binary classification or a classification has been transformed into a binary one: discriminable or not (see above for related considerations).

Accordingly, the auxiliary unit performs constant quality control, i.e., it constantly indicates whether the system is valid for the given image (determines whether the image is significantly different from the images stored in the training database), i.e., the discriminability warning is a certain kind of "validity feedback". The discriminator subunit 375 therefore gives a signal in case the system is to be run on images that are not similar to the images on which it was trained, which would result in that the diagnostic value could not be assured.

If the currently received medical image differs (it is dissimilar), then a warning is issued to the user by the system (see the block corresponding to a discriminability warning 570). Such a situation may occur for example when the user starts to work with a new isotope or marking molecule different from the training database, or a different apparatus (e.g., a different collimator) or measurement protocol (e.g., shorter measurement time). Preferably—optionally with the consent of the user—the annotated and raw images can be locally stored in the image database 575. It is important to note that the results of the patient examinations never leave the hospital/institution, i.e., either at this time or during the following steps.

As can be seen in FIG. 5, the primary medical image 505 and the secondary medical image 510 are transmitted on the one hand towards the processing unit 100 (this processes either one or both of them, and transfers a processed image to the annotator unit 200 such that they form the primary and secondary inputs thereof; both images therefore also form an input for the processing unit 100 that processes them; however, processing does not involve that it also filters the secondary image, but only that it uses the information contained in the secondary image for filtering the primary image, i.e., in this case the secondary image is not necessarily converted into a processed image—optionally, a filtered image—before it forms the secondary input of the annotator unit) and towards the auxiliary unit 300, and, on the other hand they are directly introduced into the image database 575 (in the figure, the medical images 505, 510 have a common frame, indicating that they are transmitted together).

Accordingly, all of the images are collected in the image database 575. The normal images are also collected and are labelled with "no" if they are dissimilar (the arrow leading from the block corresponding to the discriminability warning 570 to the image database 575 corresponds to that). If similarity is detected, then such labels will not be applied (no warning is issued in such a case).

Therefore, the primary medical images 505 (and—if such are also fed to the input—also the secondary medical images 510) are directly stored in the image database 575. One of the motivations behind this is to enable patient traceability.

Figure 8:
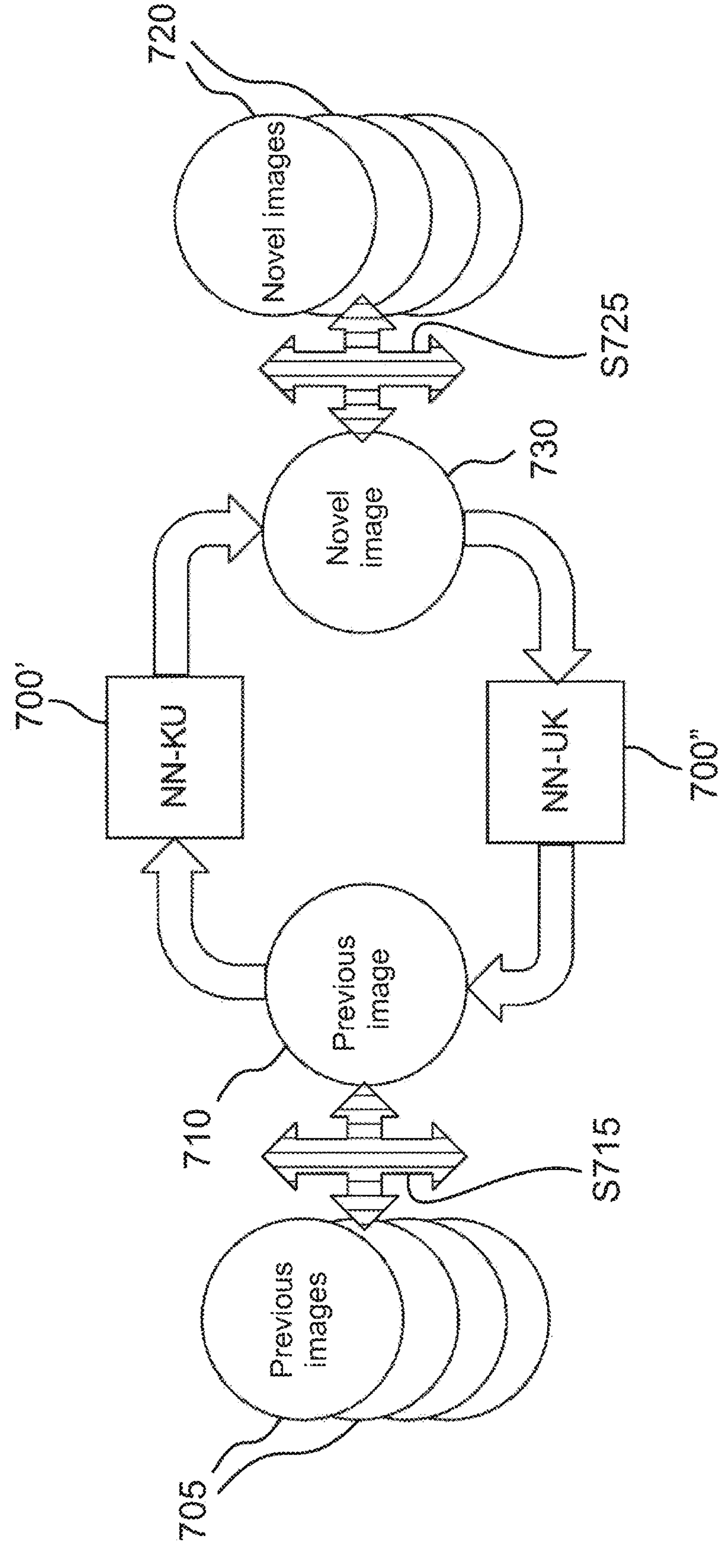
FIG. 8 is a flow diagram corresponding to an embodiment of the configuration method according to the invention.

In the case of issuing the warning, the aim of storing the images is to create a "dissimilar" database (which can be utilised for trans-training, see FIG. 8).

These images will be annotated (there is an annotator in the embodiment of FIG. 5, which provides the user with the output for an input medical image) later, after the trans-training of the system has been completed. Therefore, in case a discriminability warning has been issued, the physician can still use the system, considering that it is possible that the processed image is not correct (in such a case, it is worth to also pay greater attention to the raw image). In other words, if there is a warning, then the user uses the system further voluntarily (freely, i.e., for creating the transformation database needed for the transformation applied in the configuration method, the creation of this database is thus optional), which saves the images and preferably indicates if there are enough images available. Until trans-training has been completed, these images will not be processed—in accordance with the discriminability warning, the system is presumably not suitable for processing them—, but in such a way it can be ensured that by trans-training an appropriate transformation is available later for the different protocol.

Thanks to the direct storing, all types of images will be stored and the annotated versions thereof (if annotation can be performed for the given image).

Accordingly, the image database 575 is applied for storing not only the annotated images (this is why the image database 575 is distinguished from the database 250 of annotated images), but in accordance with FIG. 5 the annotated images 540 are also included in the image database 575, and they can be optionally also utilised—as annotated earlier images 535—i.e., they may form an optional input for the annotator unit 200 (for patient tracing and structured medical recording). A database adapted to be utilised during the use (i.e., a database comprising annotated images), such as the database of annotated images 250 can also be interpreted as forming a part of the image database 575, with the annotated images 540 being stored therein during use, unlike in FIG. 2, i.e., they are not available readily (a priori) as in the case illustrated in FIG. 2.

In FIG. 5 illustrating the use, the discriminator subunit 375*a* of the embodiment of FIGS. 3A-3B, as well as the discriminator subunit 375*b* constituted by the assistant discriminator subunits 375*b*', 375*b*" can be applied as the discriminator subunit 375, but the application of other discriminator subunits can also be conceived. The operation of these subunits will be interpreted in the following.

During its operation, the discriminator subunit does not perform a comparison as such (a concrete comparison), i.e., it does not compare the input image with a set of images. The images applicable for comparison have already been incorporated into the discriminator subunit, preferably implemented with a neural network, during its training. Considering the embodiments illustrated in FIGS. 3A-3B, during use the actual medical image 505 forms the input of the discriminator subunit at the place of the pseudo images, the output thereof being generated identically as in the training method. The images that form the basis for comparison during training (in FIG. 3A the images 335, and in FIG. 3B the images 310) will not be fed to the discriminator subunit during use, this is implied by the formulation that the expertise contained in them has already been incorporated in the discriminator subunit during training.

Thus, in case difference is calculated for a given medical image, then it is measured only for a particular image how much it differs from the images of the normal and the diseased image database. This is assessed by the discriminator subunit. Of course, for the assessment a threshold value may be applied (a predefined discrimination threshold value); if the difference designating value exceeds this, it must be indicated that discriminability presumably persists.

As regards the embodiment of FIG. 3A, the discriminator subunit 375*a* included therein can be easily substituted into the use case illustrated in FIG. 5, and, based on the above it can be appreciated how it can operate in the context according to FIG. 5.

However, in the case illustrated in FIG. 3B we proceed as follows in case of use. In this embodiment, the current medical image 505 is fed to both discriminators, i.e., to the assistant discriminator subunits 375*b*' and 375*b*", since the discriminator subunit 375*b* is constituted by these. This involves, also in this case, replacing the pseudo image, i.e., the pseudo image 345, with the actual medical image 505. During the subsequent use of the system, there is nothing to be subtracted from it by the difference-calculation unit 355, instead, in this case the current medical image 505 is fed to the assistant discriminator subunits 375*b*' and 375*b*", which perform on it the binary classification (or a classification transformed into a binary) required for the discrimination.

The assistant discriminator subunits 375*b*' and 375*b*" were also referred to above as abnormal and healthy discriminators; the actual medical image 505 is therefore in all cases fed to both of these that are able to determine if the current medical image 505 can be discriminable from the abnormal and the healthy images. Therefore, if either one of the assistant discriminator subunits 375*b*', 375*b*" (i.e., the discriminator subunit 375*b* constituted by them) indicates similarity for the actual medical image 505, then no warning is to be issued, because the actual medical image 505 is not discriminable from either the abnormal or the healthy images.

As set forth above, at the beginning the discriminator subunits 375*a*, 375*b*' and 375*b*" according to FIGS. 3A-3B were untrained, but by the end of the pre-training process they have become pre-trained (and these components are not subjected to further training in the course of joint training).

In relation to the following, reference is also made to the detailed description of the figures referred to below. Therefore, now such a case will be described in more detail in which images determined to be "dissimilar" by the loss test are fed to the system, i.e., the system collects such images.

In case a sufficient number of novel images have been collected (i.e., a transformation database comprising images 720, 730 has been created), image transformation operators (which correspond to the transformation unit, see below) implemented by NN-KU and NN-UK neural networks can be trained for example applying a CycleGAN-based network illustrated in FIG. 8, and the images synthesised by the auxiliary unit can be transformed, filtered, and, applying the ROC unit 500 according to FIG. 4—or using other name, the ROC analyser—can also be evaluated (on this latter see FIGS. 9A-9B). This evaluation is able to establish by the help of NN-KU transformation the system's diagnostic value for novel images. If the diagnostic value is still favourable, the discriminability warning 570 (warning component) of FIG. 5 can be subsequently deactivated for novel images, because the diagnostic value of the system has been assured (in relation to these aspects, see the description of FIGS. 8, 9A, 9B, and 10 below). By the help of this method, it can be avoided that a very large number of novel training images for the complete newly training (re-training) of the system should be acquired (obtained). Obtaining such images would be problematic in any case because it would require entering into new contracts and securing ethical permissions, and they would have to be newly validated by physicians, which would be very time and resource-consuming.

In the following, a brief summary on the preferably applicable major components of the invention will be provided (while giving—in a manner that makes certain aspects included below optional—a less definition-like description of the components compared to the above discussion); therefore, in the method and system according to the invention, we preferably apply:

I. One or more image processing modules (or steps), for example in the illustrated embodiment of the invention an image noise filter implemented by means of artificial intelligence-based technology. Optionally, more than one processing units can be applied successively, whereby various image enhancement technologies can be applied to an image (for example an edge-retaining noise filter and a motion blur correction module): These components can be trained separately (on their own) during pre-training and can then be utilised sequentially.

II. An annotator that is able to identify (find and mark) and classify the structures, accumulations different from normal (generally, lesions; also in the points below). According to the above, this unit is also implemented applying AI (artificial intelligence) technology.

III. An auxiliary unit that is able to synthesise medically relevant images and different from normal structures, which can be an image comprising for example accumulations (i.e., images comprising everything), or a layer image (comprising only the accumulations, with only the locations of the accumulations being marked, or alternatively also containing the intensity and other qualitative parameters thereof). In our case, this unit is preferably implemented applying technology based on GAN-based artificial intelligence that is trained applying normal and different from normal images, but other solutions, such as applying Variational Autoencoders, can also be conceived.

IV. An ROC unit (ROC generator), which is able to generate a diagnostically relevant measuring number based on the lesion/structure layer received from the auxiliary unit and the image (generally, data packet) formed after being passed through the image processing chain and the annotator. In our case, this involves drawing the ROC curve and calculating the area under the curve (AUC), which is then fed back to the training process of the image processing and annotator components described above (for a list of the components included in an embodiment, see below; also see the feedback process in FIGS. 4 and 6). After joint training, the neural networks of the system can operate together (FIG. 5) or in a standalone manner (e.g., as in FIG. 1).

In the description above we provided a brief summary of the most important components of the invention; in the following, the directions of generalisation of the invention are given, listing possible fields of use and modes of application.

1. The invention can essentially be applied for all kinds of medical imaging systems, i.e. for all medical imaging modalities, including the technologies
   - SPECT (Single Photon Emission Computed Tomography)
   - Scintigraphy, i.e., planar gamma camera examinations
   - PET (positron emission tomography)
   - CT (computed tomography)
   - MRI (magnetic resonance imaging examinations)
   - Optical imaging
   - Ultrasound
   - but at the same time other medical imaging technologies can also be conceived (such as for example microscopy applications, microwave tomography, optical coherent tomography, other tomographic approaches, etc.).
2. The invention can be applied in any medical, medicobiological, research and clinical applications of the given medical imaging technologies (imaging, nuclear medicine), such as in
   - Oncology examinations (for example scintigraphy, oncological SPECT, PET, PET/CT, PET/MRI examinations);
   - Cardiology examinations (for example cardiological SPECT, coronary CT, angiography, static and dynamic, as well as gated heart examinations);
   - Neurology examinations (for example cervical SPECT, MPH [multi-pinhole] for brain SPECT, MRI, PET/MRI, etc. targeted at multiple disease groups, such as Alzheimer's, epilepsy, Parkinson's disease (DaTSCAN scans, https://www.ema.europa.eu/en/documents/overview/datscan-epar-summary-public_hu.pdf);
   - Biologically relevant, typically flow-through or dynamic examinations of the kidneys, the pancreas and other organs or organ groups; and
   - Preclinical examinations (MRI for pets, MPH-SPECT, PET for pets).
3. In general, the invention can be extended to several (image) processing steps—i.e., to processing units having such functions—for example
   - noise filtering (see in FIG. 1 and in the example included below);
   - image sharpening;
   - image distortion and the correction thereof (for example, in the case of MRI, sampling distortions, magnetic inhomogeneity correction);

visual representation applying colour scales that may enhance or conceal important, diagnostically relevant regions;

motion correction (a type of sharpening, i.e., image correction; the processing unit basically corrects motion blurs that distort the input image).

4. Generally, it is meant to cover the implementation of all types of auxiliary units, which can be GAN technology image synthetisation based on artificial intelligence (see FIGS. 3A and 3B);

CycleGAN-based synthetisation applying super-resolution (resolution increase; see the example below);

image synthetisation applying artificial intelligence-based Variational Autoencoder technology (Xianxu Hou et al: Deep Feature Consistent Variational Autoencoder, 2017 IEEE Winter Conference on Applications of Computer Vision (WACV)); in this case no native discriminator is applied which would form a part of the GAN (i.e., it is applied for generating/synthesising pseudo images), however, a discriminator network can be trained independently, i.e., the auxiliary functions thereof (generator and discriminator subunit) can be implemented also by Variational Autoencoder-based technology;

other artificial intelligence-based image and lesion structure/layer image synthetisation technologies not listed here.

These are all artificial intelligence-based (machine learning) solutions.

Referring to the description of the processing unit (module) above, it can be generally written (composed) that the function thereof is to generate a better-annotatable image from the input image. Regarding the processing directions listed in point 3 above, the following observations are made.

In this respect, noise filtering and de-noising of the images provide obvious results, i.e., a better (less noisy) image is obtained on the output, which then proceeds toward the annotator. Also in this respect, image sharpening can also be interpreted, which essentially results—through sharpening rather than noise filtering—in that a basically better-quality image is fed to the annotator. The focus is on improving the signal-to-noise ratio.

To address the issue of image distortion, such an artificial intelligence-assisted module can be possible that is able to transform away an image defect (e.g., in the case of MRI, the inhomogeneity of the magnetic field), thereby reducing the artifacts in the image. According to the literature, the noise itself is an artifact, i.e., an image defect that may affect diagnosing. Accordingly, this type of application can also allow better-quality annotation.

The application of a colour scale can for example display or conceal small-scale accumulations. Such a case may occur where a user would not like to have an annotator in the deployed system (e.g., because she/he would like to make medical record of the images in the traditional way). In this situation, applying a colour scale means a processing operation in a sense that the selection of the colour scale—even aided by the monitor—may help achieve annotation with adequate performance (i.e., a performance equalling that of an NN annotator—or the physicians who annotated the training images). Applying an arbitrary colour scale would not necessarily aid this, but colour scales that can be applied with the processing unit and are adapted for aiding annotation may be preferable (this is also a feature highlighting operation, cf. that the filter trained according to the invention for example also has the objective of generating an output that will aid annotation).

When such a system is undergoing medical verification, it is expedient to apply fixing of the colour scale. On the other hand, contrast adjustment (via a slider) by the physician may be allowed. For example, there exist such special (display) monitors that are able to detect the light conditions in a lab and adjust the contrast and brightness of the displayed image accordingly, in a calibrated manner. The system disclosed in the present description—which preferably integrates neural networks—is, however, independent of all that, because its performance (which is measured by the ROC unit) is not dependent upon that. At the same time, though, this system is validated by human physicians, i.e., it does not contain only the filter and annotator, as the physician receives or selects a colour scale, as well as uses a monitor. The advantage of the system is, thus, that on the one hand it provides a verification of diagnostic value that is independent of these factors—i.e., the colour scales or displaying—, and on the other hand, when comparing the system with human physicians it is important to bear in mind that the physicians interpret information on the basis of additional factors (such as the colour scale). This latter is implicitly introduced in the training process anyway because the annotator is trained applying physician-annotated images.

In the following, certain optional aspects of the invention are described in detail.

The specificity and sensitivity of the system according to the invention can be maximised by parameter tuning for the ROC curve, i.e., it is ensured that—in accordance with the earlier training sessions—the machine learning units trained by joint training (preferably such units that are implemented by neural networks, i.e., the processing unit and the annotator unit) do not introduce false accumulations into the image, and to not remove accumulations that are present in the image, in other words, such probability of occurrence of such cases is as low as possible.

In relation to that, in an embodiment of the invention it can be preferably examined to what extent the recording (measurement) time and the activity injected to the patient (gamma camera examinations, SPECT, PET) or the X-ray dose (i.e., X-ray tube current in the case of CT) can be reduced, and that the highest possible signal-to-noise ratio can be achieved applying the shortest possible measurement time (by optimising the excitation sequence in the case of MRI), such that the diagnostic value of the protocol routinely applied by physicians can be preserved.

A possible implementation of this, as a preferred embodiment, is an examination performed after joint training, wherein the generation of images with higher noise content (i.e., increased-noise, reduced signal-to-noise ratio) from images conforming to the normal protocol (i.e., images generated by the auxiliary unit also during joint training, and/or other generated images that are similar to them) is achieved by a noise generation unit 600 (for short, a HN-Gen module, “higher noise generation unit” or device) inserted-between the auxiliary unit 300 and the processing unit 100 (for example, NN-filter)-into the branch (shown in FIG. 7) adapted for evaluating the performance (i.e., diagnostic value) of the system during joint training, for example, by applying a binomial-distribution resampling of the images (i.e., by subsampling them).

By the help of this device—i.e., the noise generation unit 600—the relevant ROC analysis characteristic for the higher-noise images can be performed, and the extent by which for example the activity (Amax: this is the highest value being diagnostically safe, for related aspects, see below) can be reduced without causing a significant change in diagnostic performance (the efficacy of diagnostic assistance) can be established.

Accordingly, FIG. 7 illustrates the optimisation of the gathering protocol (i.e., subsampling), that is, for example the extent to which the activity/measurement time/tube current can be reduced, i.e., examining the effects and the ROC analysis of these reductions (see the generic formulation below of this embodiment of the method). For example, the tube current will be relevant for X-ray and CT, while activity is a relevant measure in the case of modalities requiring the injection of isotopes; measurement time can be interpreted generally for the modalities (i.e., this parameter can be modality- or application-dependent; below basically the activity and measurement/sample time are given as examples).

In accordance with the earlier figures, the ROC analysis can be performed applying the images generated by the auxiliary unit 300. As illustrated in FIG. 7, the noise generating unit 600 is also integrated in this framework system. The analysis of the reduction proportion, i.e., the highest possible value of the reduction parameter (A) achievable by the noise generation unit 600 can be established during a reduction proportion checking performed after the joint training, based on the following aspects: The steps of the reduction proportion checking can thus be performed after training the system (after the pre-training and joint training, i.e., after the end of the training method), see also the steps thereof below. In this framework we investigate the limits between which the system can be applied without significantly changing its diagnostic value.

Accordingly, after completing the training according to the invention, these values can be assigned to the system, indicating that the system can be safely applied in such a range of activity/sample time. This is more preferable than the known approaches wherein for example a safe activity range is determined empirically and it is recommended for radiologists the examination. Thus, in the case of the known technical approaches the protocol may vary from hospital to hospital. It is therefore advantageous that the system according to the invention can be considered robust for the changes of this parameter.

In the present embodiment, the invention improves upon that by allowing the determination, during the reduction proportion checking, also of the manner how the system reacts to the reduction of activity/sample time (basically, the reduction of the product of these parameters is what is important so for reducing one or the other, or both), i.e., by establishing if the diagnostic value of the system is deteriorated.

The possibilities for reducing the activity and sample time can be modelled and examined by generating various reduced-statistics samples from a given image and utilising our system for determining the statistical deviation exhibited by the image processing chain (filter+annotator). Based on that, it can be determined if a change is significant or not, i.e., whether sampling performed with reduced statistical parameters (increased noise) reduces the diagnostic value.

Determining the reduction proportion of the activity/sample time without the significant deterioration of the diagnostic value helps in this embodiment firstly in reducing these parameters in a well-founded way, and secondly in that it is not necessarily a problem if the system is applied for evaluating images taken applying lower activity/sample time values, i.e., the system will be applicable for such evaluation (in the activity/sample time range determined this way, losing the diagnostic value of the results is not a real risk).

Therefore, the present embodiment allows the significant reduction (typically to ¼ of the previous value, but even by a greater degree) of the activity or dose required for the examination, which significantly reduces the risk of the examination both for the patient and the operator staff of the system.

Another related preferred use of the invention is that by applying the embodiment illustrated in FIG. 7, the applicable reduction proportion of the activity or sample time parameter can be determined for the given examination (for the current image under investigation).

As it is illustrated in FIG. 7, according to the above in this embodiment the ROC analysis is carried out by transferring an abnormal accumulation layer image 605 towards the ROC unit by the auxiliary unit 300. At the same time, abnormal pseudo images 610 generated by the auxiliary unit 300 pass through the noise generation unit 600, which transforms them utilising the λ parameter (resamples them, i.e. subsamples them applying the λ parameter) as if a smaller activity/sample time corresponded to them (this resampling is typically stochastic rather than deterministic). The processing unit 100 will already process the transformed images, and will transfers them towards the annotator, from where they reach to the ROC unit.

Like in the above-described case, based on these two inputs, i.e., the input originating from the annotator and the abnormal accumulation layer image 605 (here these play the role of the second and the first lesion location data packet, respectively; the abnormal accumulation is generally a lesion) the ROC unit is able to carry out the ROC analysis for the images generated by the auxiliary unit 300 as if the images had lower activity/sample time, and it can also be determined if the diagnostic value is still acceptable in the case of the given value of the λ parameter. In case the diagnostic value decreases below a critical (predetermined) value for a given value of the λ parameter, the previous one which is smaller applied λ value is the highest for preserving an appropriate diagnostic value.

In the embodiment illustrated in FIG. 7, therefore, after the joint training, in course of a reduction proportion checking (verification), for one or more parameter values of a reduction parameter λ (the values) being greater (larger) than one, reduced signal-to-noise ratio images are generated by subsampling—typically according to a stochastic distribution—checking auxiliary pseudo images by means of the auxiliary unit by the parameter values of the reduction parameter (a new type of pseudo image has been introduced here which are applied when the joint training has already been completed, see the pseudo images 610 in FIG. 7; these typically come from a newer generating that is also carried out after the joint training), by transferring to the ROC unit second lesion location data packets determined by the successive application of the processing unit and the annotator unit on (onto) the reduced signal-to-noise ratio images, and also respective first lesion location data packets corresponding to each of the checking (reduction proportion checking) auxiliary pseudo images, a value of the AUC parameter corresponding to the parameter value of the reduction parameter λ is determined, based on the values of the AUC parameter corresponding to the respective reduction parameter values λ, a highest value being diagnostically safe is determined from among the one or more parameter values of the reduction parameter λ.

In this embodiment, in accordance with the above, after completing the joint training we can "map" the activity/sample time range in which the trained system can be used safely. This method is thus aimed at improving the signal-to-noise ratio; in order to achieve that we look at how the imaging parameters change if the signal-to-noise ratio is reduced and determine the greatest reduction parameter value that can be still safely applied.

This method is determined by the deviation band corresponding to the ROC curve. If the expected value of the new ROC curve reaches the edge of the deviation band, then it can be claimed that reducing, for example, the measurement time below this limit would result in a significantly deteriorated failure rate. This can also be projected to the AUC parameter.

We therefore seek to find the highest reduction parameter (λ value) that is still diagnostically safe. That is, we choose the highest λ value at which the expected value of the new AUC parameter—when projected a previous AUC parameter value—does not yet differ from the previous AUC parameter value by more than the standard deviation of the AUC parameter at λ=1 (the last one of such AUC parameter values is selected, i.e., if the next differs to a greater extent, it will not be selected), i.e., more generally, at which value there is still no significant difference in the AUC parameter value. This involves that the change in the diagnostic performance (i.e., that the system is able to provide valuable diagnostic aid) is not yet significant, i.e., the results can be considered diagnostically safe for this λ value, and therefore the system has preserved its diagnostic value.

In the above embodiment, furthermore, the reduction proportion checking is carried out applying parameter values of the reduction parameter A between 2-100 (choosing the parameter values from among powers of two with exponents equal to or greater than one). Further, the reduction proportion checking is particularly preferably carried out applying the first, second, and third powers of two as the parameter values of the reduction parameter.

As it was also mentioned in the introduction, in the current state of science the intrinsic variability of the given patient examination cannot be derived from nuclear medicine examinations, i.e., applying the available known methods it is difficult to establish the correctness of the actual diagnosis made with the help of the data provided, that is to establish the confidence level of said diagnosis (cf. computer aided diagnosis approach).

In principle, the variability of the given diagnosis could be measured by sequentially performing and evaluating multiple independent measurements, which would allow determining the (standard) deviation of the results (for example, the number of identified abnormal accumulations). However, this is practically not feasible (not realistic), because in such a case the patient would have to lie inside the scanning apparatus (apparatus for making a recording) even for multiple hours instead of the typical examination times of $T_{exam}$≈20-30 minutes.

The embodiment of the invention described in detail above provides a solution for investigating variability by also enabling the application of significantly reduced measurement times $T_{red}=T/\lambda_{max}$ instead of the examination time $T_{exam}$ corresponding to the "normal" protocol while preserving the diagnostic value, where the reduction factor $\lambda_{max}$ (which corresponds to the highest value of the reduction parameter mentioned above) is typically a number between 2-100, preferably between 2-8 (including in both cases the boundary limits).

Performing the examination by applying a $T>T_{red}$ and recording the data in list mode (which allows the subsequent evaluation of the data), by shifting the data by $dT<<T_{red}$ the measurement data can be arranged into N independent measurements (the so-called "binning" method involves, in the case of SPECT, the generation of projectional image sequences, and in the case of PET, the generation of LOR—"line of response"—data), where $N\geq\lambda_{max}$.

By passing the N independent measurements thereby produced through the diagnostic branch that comprises the NN-filter and the NN-annotator (this branch will provide the results for aiding in making the diagnosis), diagnostically relevant measuring numbers can be obtained for each measurement, and additionally, their average and standard deviation can also be determined. This helps determining the accuracy of repeatability, which is essential for accurately tracking the patient's status, and for aiding the selection of the most effective therapy for the patient.

In the following, the robustness of the system will be illustrated by describing an embodiment confirming it (reference to this has already been made above in the description of FIGS. 8-10).

Some modifications fundamentally affect the characteristics of the entire imaging system, for example replacing the camera (type, manufacturer), replacing the image reconstruction software resulting in significant changes in image quality, or for example in the case of gamma cameras or SPECT, replacing the collimator. The effects of such modifications cannot be modelled in a manner described above, which could result in that the system according to the invention trained on a different set of images would not be applicable with the images taken utilising these new devices (see also further modifications mentioned in relation to robustness; other such modifications are also conceivable). An example for this can be a situation wherein the system had earlier been trained applying images taken with a LEHR collimator, and now we would like to switch for example to a LEHR-HS (LEHR High Sensitivity) parallel or multi-pinhole collimator.

Figure 9A:
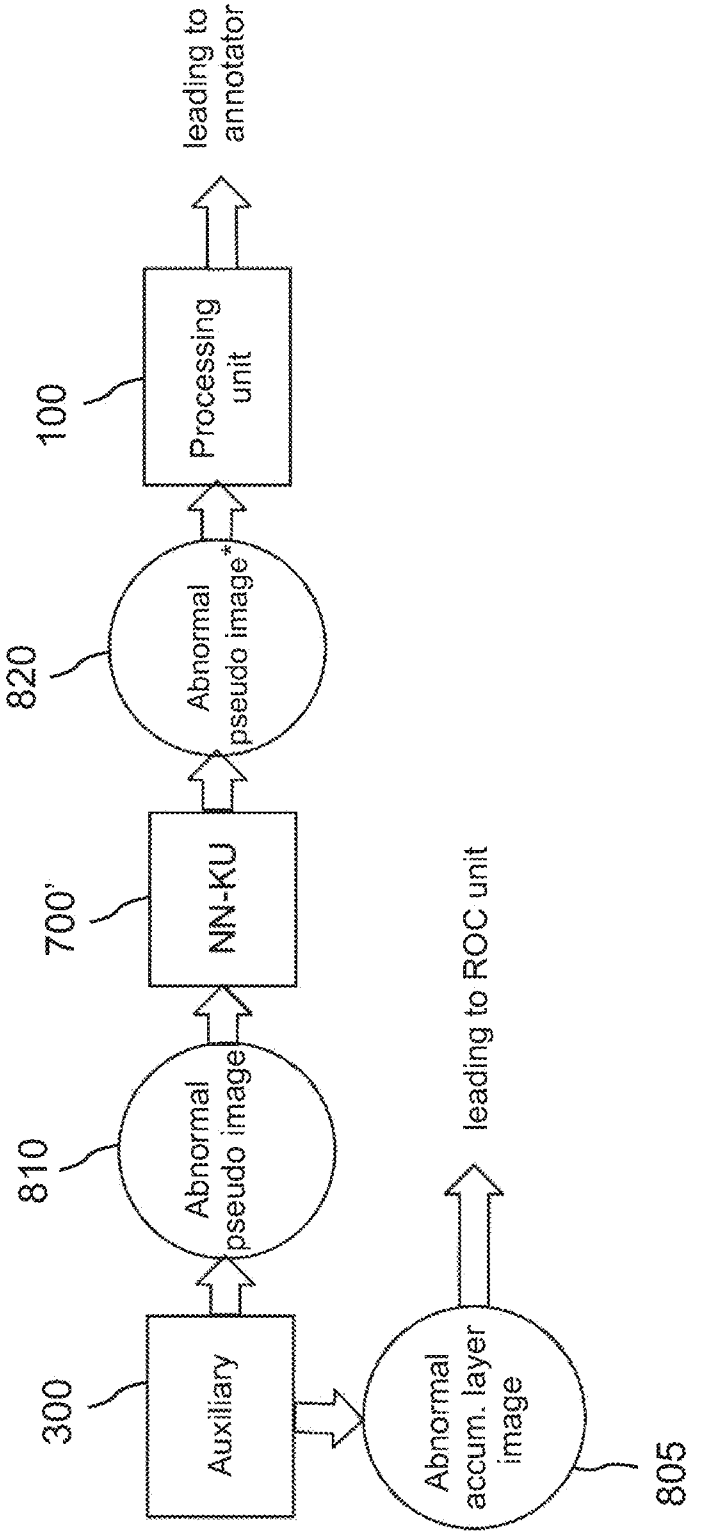
FIGS. 9A and 9B are flow diagrams illustrating respective steps of the configuration method.
Figure 9B:
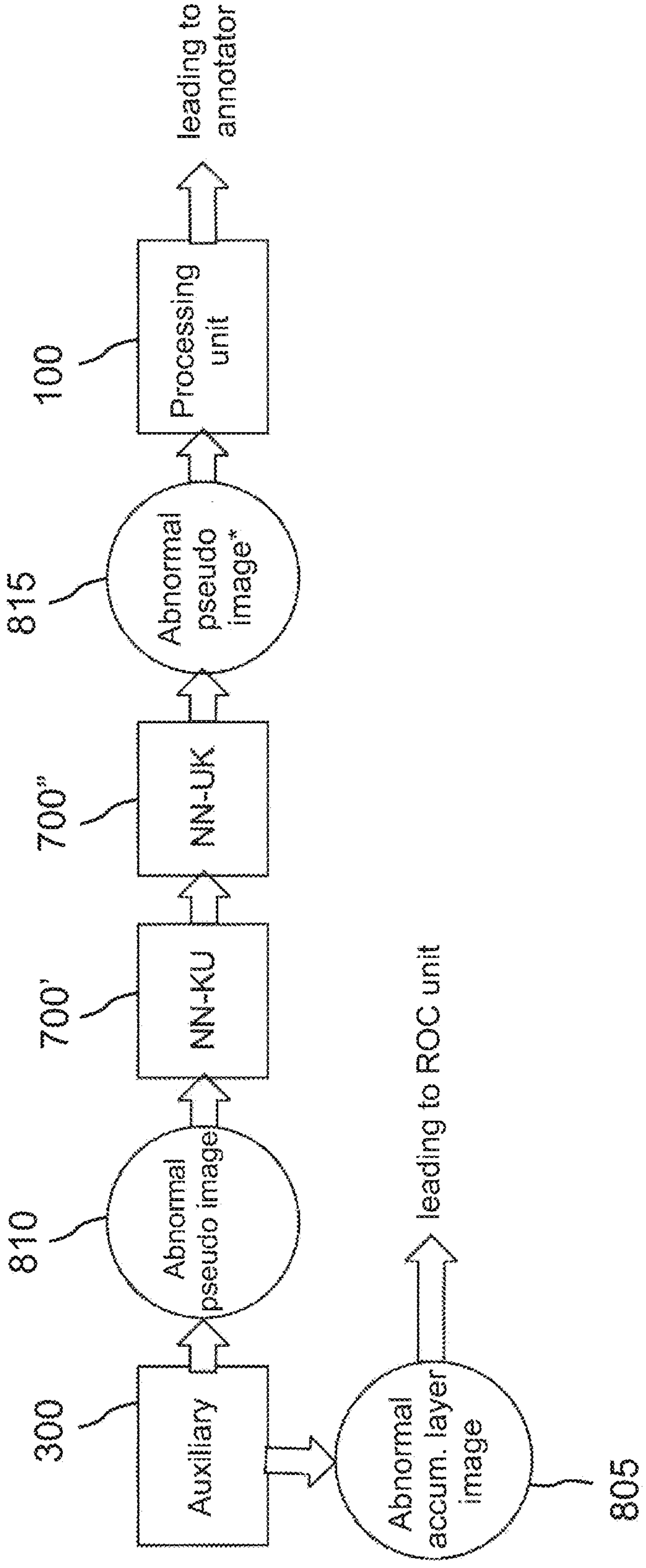

In this situation it is important to investigate if it is required to newly train the system (the examinations according to FIGS. 9A and 9B are directed at that, see below), which would require thousands of patient examination images that would have to be newly analysed and annotated by physicians. It can thus provide a great advantage to be able to investigate whether it is possible to avoid image processing requiring newly training and significant demand for physician resources.

In order to check the compatibility of novel images (images taken after making the above-mentioned modifications fundamentally affecting the characteristics of the imaging system) with the trained system, in an embodiment a clustering algorithm can be applied, which is able to indicate a measure of similarity between the images applied for training the auxiliary unit and the set of novel images (cf. FIG. 5, where the functionality of the clusterer is performed by the discriminator subunit 375 of the auxiliary unit 300).

In an embodiment, the clusterer (discriminator) can be a K-nearest-neighbourhood-type algorithm, or a suitable clustering neural network adapted for unsupervised learning, i.e., the discriminator subunit can be implemented applying these. The discriminator is therefore termed here a "clusterer", but it can be also implemented differently than it is described herein; in this description the term "discriminator" is more frequently used to refer to this module. This also indicates that, in general, the discriminator subunit—like other units implemented for example applying neural networks—can also be implemented based on machine learning algorithms, regardless of the particulars of the applied machine learning method.

If a significant portion of the novel images (i.e., the images fed to the system after making the modification) are determined to be "dissimilar" by the clusterer (preferably the discriminator subunit 375 which is watching the input and issues a warning if something has changed) from the database that was synthesised with the auxiliary unit 300 and was applied for training the system during the joint training, then it is expedient to check whether such a mapping can be found that is able to transform the novel images into such images with which the system was trained. Certain embodiments of the invention relate to a configuration method that can be applied for performing this transformation (see below).

Such a transformation can be implemented as a preferred embodiment for example applying cycle-consistent GAN networks (on CycleGAN neural networks see e.g., Jun-Yan Zhu et al. Unpaired Image-to-Image translation using Cycle-Consistent Adversarial Networks (2017), arXiv: 1703.10593v7, 24 Aug. 2020). This network comprises two transformation functions:

- one of them performs NN-KU "previous"→"novel" image transformation (this is the so-called "mapping function"),
- the other performs NN-UK "novel"→"previous" image transformation
- (see FIG. 8). According to the document referred to just above, the loss function applied for modifying the KU and UK networks depends on the particular generated previous and novel images, and also on the similarity (as measured applying the given metric) between these images and the training sets of previous and novel images.

FIG. 8 illustrates the CycleGAN image transformation process, showing a cyclical training way (method) wherein a previous image 710 and a novel image 730 are involved together with a NN-KU transformation unit 700' (in an alternative term, a first transformation unit implemented by a neural network; i.e., a transforming unit) and a NN-UK transformation unit 700" (in an alternative term, a second transformation unit implemented by a neural network). The training also involves utilising previous images 705 (a first operational step S715 illustrating the calculation of a loss function corresponds to this), as well as novel images 720 (a corresponding second operational step S725 also illustrates the calculation of a loss function).

According to FIG. 8, therefore, training is carried out in a cyclical manner, wherein novel images also appear, i.e., it is investigated if the previous (earlier) images can be appropriately transformed into the novel images and vice versa, that is, if the system trained on the previous images can in some way be "trans-trained" for the novel images. (i.e., if, by the help of—inserting—transformation, the system according to the invention can be applied for the novel images; see FIG. 10, this operation includes the training of the transformation units 700', 700", so this step can be considered a trans-training step). Accordingly, in the cycle (circulation) illustrated in FIG. 8 the forward and backward" transformations are simultaneously trained, thereby training the corresponding transformation units 700', 700".

In relation to FIG. 8, the following observations are made. The operation of CycleGAN can be learned from literature (e.g., Jun-Yan Zhu et al. Unpaired Image-to-Image translation using Cycle-Consistent Adversarial Networks (2017), arXiv: 1703.10593v7, 24 Aug. 2020, see also FIG. 16). CycleGAN can be preferably applied as a tool in the framework of the invention. This is motivated by the recognition that its application may have a very advantageous effect in the case of the invention. It is important to note that we do not know of any related CycleGAN applications, and here it is not merely a new application thereof but a recognition that in the present technical field, in the event of occurring novel images an attempt can be made to apply the CycleGAN scheme for configuring the system for reacting this change, that is, a change of the character of the images can be reacted to by transforming the images such that they have character corresponding to the previous images. We believe that, in line with this reasoning, the incorporation of the CycleGAN framework as a tool into the present invention is non-obvious.

Accordingly, we do not give the detailed description of the CycleGAN framework system, only making reference to its feature that the cyclically applied transformations (cf. the NN-KU and NN-UK transformations in FIG. 8) are applied therein for transforming previous images (images utilised for the initial (basic) training of the system) into novel images and vice versa.

In relation to the manner of CycleGAN operation illustrated in FIG. 8 it is also noted that the transformation units NN-KU 700' and NN-UK 700" are trained according to the followings.

The training can be initiated by feeding a novel image 720 to the transformation unit NN-UK 700" (that is, a partial process is started at this point). We examine the degree of similarity of the previous image 710 obtained by the transformation to the other previous images 705. Thus, an image is obtained by the transformation, which is to be examined whether it has similar character to the previous images 705, i.e. whether the "novel"→"previous" transformation works well. Each novel image 720 can serve as the starting point of this process, and it is thus possible to obtain a loss value from these comparisons in operational step S715 that can be applied for training the NN-UK transformation unit 700". The distance of each previous image 705 from the current image 710 is measured applying for example the L1 metric (or a different metric), and the sum of the distances is calculated.

In a different partial process, the previous image 710 can be transformed applying the NN-KU transformation unit 700' (also proceeding through each of the previous images 705, 710), and in an operational step S725 analogous to the above, a loss value adapted for training the NN-KU transformation unit 700' can also be calculated (composed). The sequence of these two-directional partial processes can also be considered as a CycleGAN pre-training process.

Such a training process can also be applied wherein a full cycle of transformations is carried out, i.e., for example a novel image is subjected to the NN-UK 700" transformation unit, and the previous image 710 thus obtained is then subjected to the NN-KU transformation unit 700', with the loss value being calculated on the basis of how well the original novel image has been restored (as shown in FIG. 8—see the operational steps S715, S725—there are two neural networks learning simultaneously with the transformation units 700', 700" which are now applied for generating an image from another; the discriminator implemented by the operational steps S715, S725—which can also be considered a discriminator unit/subunit—learns simultaneously with these, and its performance is evaluated in case it cannot determine whether the input image originates from the given image database or it is a generated/transformed image). Such a process may also be initiated from the previous image 710. In the case of these partial processes the calculated loss are utilised for training both the NN-KU transformation unit 700' and the NN-UK transformation unit 700".

The network trained in such a manner will of course require that a sufficient number of images (recordings) are collected applying the system new (i.e., created after the modification). It is however important to note that for such an trans-training process it is expectedly sufficient to collect a way lower number of novel images (the images do not have to be "moved" from the location where they are taken, which would pose ethical and legal difficulties), and on the other hand it does not require the analysis of each novel image by a physician, because—as illustrated in FIGS. 9A-10—it is provided together by the auxiliary unit and the ROC unit components that the clinically valuable characteristics of the system are preserved. An embodiment applying this solution is thereby rendered particularly preferable.

For the compatibility check (test) of the image transformations thus produced the KU and UK operators can be built in and the ROC analysis can be performed a manner illustrated in FIGS. 9A-9B.

FIG. 9A illustrates the compatibility check (ROC analysis) of the trained image transformation, utilising only the KU transformation. In the embodiment shown in FIG. 9A, the pseudo images generated by the auxiliary unit 300 are transformed into novel images, and it is examined how big a difference this causes according to the ROC analysis (cf. FIGS. 9A-9B to FIG. 4: the ROC analysis is performed in accordance with that including the transformation unit 700' or both transformation units 700', 700" at an appropriate position). If the difference in the AUC value obtained based on the ROC analysis of FIG. 9A is not significant (i.e., is acceptable), then the trained (previous) NN-filter and NN-annotator branch can be utilised for the novel images (however, if there is a significant difference, we continue with the ROC analysis according to FIG. 9B, see below).

The ROC analysis allows for verifying the diagnostic value. However, according to the above the ROC analysis can be performed on the pseudo images generated by the auxiliary unit 300, i.e., there is no direct way of verifying the diagnostic value on the novel images.

In FIG. 9A a first step of the verification is illustrated wherein pseudo abnormal images 810 generated by the auxiliary unit 300 are transformed with the NN-KU transformation unit 700', i.e., with that which was trained in accordance with FIG. 8 for performing the transformation of the previous images 710 into the novel images 730. Accordingly, from the pseudo abnormal image 810 we obtain transformed pseudo abnormal image 820, which after being transferred to the processing unit 100 proceed to the annotator, and, together with the abnormal accumulation layer image 805 originating from the auxiliary unit 300 can be applied for the ROC analysis.

The abnormal accumulation layer image 805—in general, this is an auxiliary lesion image—illustrates the locations of the abnormal accumulations, so it is not necessary to carry out a transformation thereof (this is not affected by modifications that otherwise require a transformation), with novel images arriving from the pseudo image branch, so the ROC analysis can be performed for the novel images (in the method steps of FIG. 9A we essentially examined the results of ROC analysis for the novel images—which are obtained by the included NN-KU transformation unit 700').

If the result of the ROC analysis performed in this manner is that the diagnostic value stays acceptable, then it is not necessary to apply the transformation unit, and the system is left unchanged. In accordance with FIG. 9A, therefore, we examine whether the ROC curve corresponding to the novel images significantly differs from the ROC curve generated applying the previous images (the comparison can of course be performed utilising the AUC values).

FIG. 9B illustrates the compatibility check (ROC analysis) of the trained image transformation, utilising the KU-UK transformation. If the above analysis according to FIG. 9A yields the result that the AUC parameter value is significantly smaller for the novel images (than the AUC parameter values obtained for the previous images), then the step of checking the compliance of the trained NN-KU NN-UK operator pair is performed; this is reflected by the arrangement implemented according to FIG. 9B. The compliance is indicated by an insignificant change of the ROC curve and the AUC parameter value (with respect to the ROC curve and AUC parameter values obtained for the previous images).

According to FIG. 9B, therefore, a further verification (i.e., another type of ROC analysis) is performed in respect of the transformations and the diagnostic value (in case the investigation performed according to 9A leads to this). Accordingly, the pseudo abnormal images 810 are subjected to the NN-KU transformation unit 700' adapted for generating a novel image therefrom, and, immediately thereafter, also to the NN-UK transformation unit 700" that transforms to an image that again corresponds to the previous images. By performing the ROC analysis for the pseudo abnormal images 815 obtained this way, it can be investigated whether the back-and-forth NN-KU-NN-UK transformations have deteriorated the diagnostic value (it would indicate that they are not usable). In such a manner it can be made sure that the NN-KU transformation unit 700' and the NN-UK transformation unit 700" can be applied without deteriorating the diagnostic value.

As can be observed in FIGS. 9A-9B, the abnormal accumulation layer image 805 generated by the auxiliary unit 300 is not subjected to transformation, i.e., it is transferred towards the ROC unit along a different branch without being transformed. It is possible (and correct) to do so because the sole purpose of the abnormal accumulation layer image (generally: the lesion image) is to enable the identification of the location and type of the different from normal accumulations.

There can also occur such situations (for example in case due to changing the applied isotope a completely different accumulation structure appears with respect to the case according to the original training) wherein the above-described transformation-based approach cannot be applied. In such cases an information transport between the old and the new images cannot be performed, because an image show fundamentally different biological processes than the other. Unfortunately, in these cases even a transformation also of the abnormal accumulation layer image applying the NN-KU transformation unit 700' cannot help. However, due to the above, in all other cases it is not necessary to transform the abnormal accumulation layer image 805, because the above-mentioned modification (i.e., modifications for which the invention can be preferably applied) does not affect either the location or the classification of the lesion.

In the case of a positive outcome of the verification test according to FIG. 9B detailed above, it is therefore possible to apply the transformation during use. Accordingly, the novel image transformed by the NN-UK operator can be applied in clinical analysis in accordance with FIG. 10; in other words, it can be applied in the Processing unit→Annotator image processing chain as shown in FIG. 10.

Figure 10:
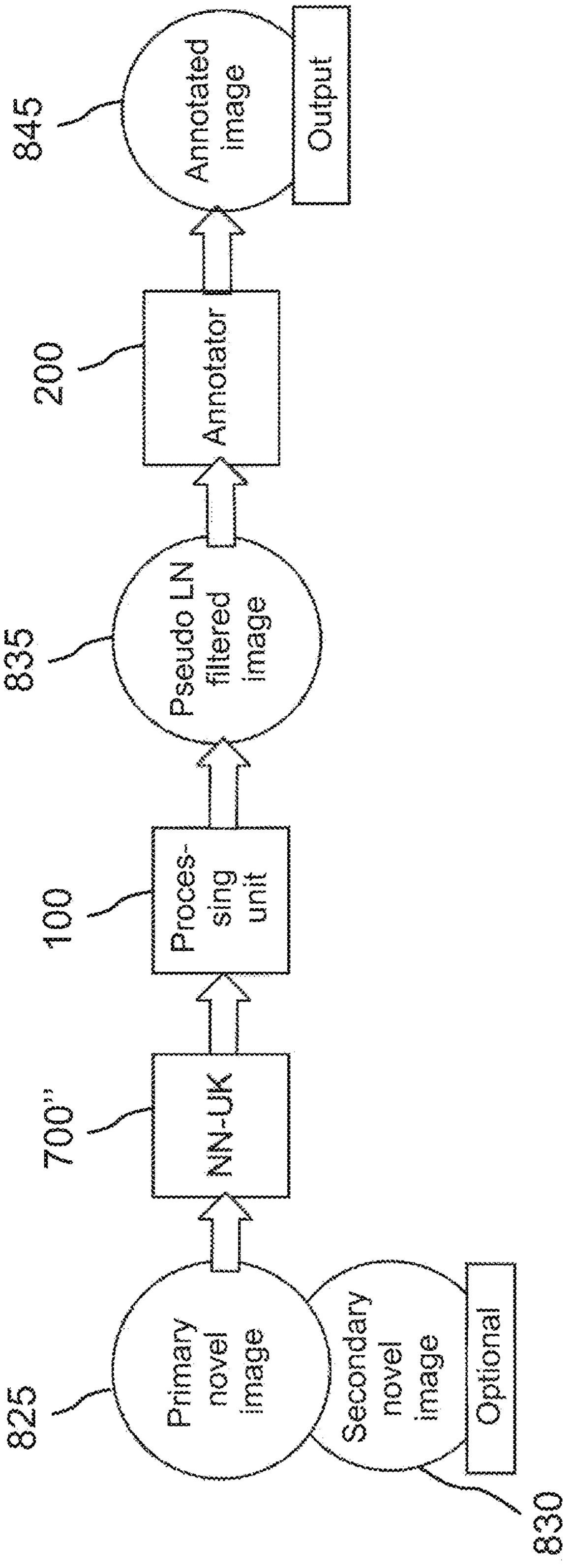
FIG. 10 illustrates the operation of an embodiment of the configuration method.

Following the above-described reflections, in accordance with FIG. 10 the NN-UK transformation unit 700'' can be applied in such a case because, as illustrated in FIG. 8, it generates a previous image (e.g. previous image 710) from the novel image (e.g. novel image 730), which then can be subjected to the components shown in FIG. 10, i.e., first the processing unit 100.

In the case illustrated in FIG. 10, a primary novel medical image 825 as well as an optional secondary novel medical image 830 are subjected to a transformation by the NN-UK transformation unit 700'' (fitting to other processes, the image can be planar or spatial image). Accordingly, FIG. 10 illustrates an assured diagnostic value filtering and annotation workflow for novel images, wherein the NN-UK transformation unit 700'' is inserted upstream of (before) the processing unit 100, thus generating a pseudo-LN (low noise) filtered novel image 835 (i.e., the processing unit 100 behaves as a filter unit also in this example) that are fed to the annotator unit 200, producing an annotated image 845.

As a short summary of the above, it can be established that in the case of a trained system the transformations may be needed during use; i.e., in accordance with FIG. 8, a trained state of the NN-KU and NN-UK transformation units 700', 700'' can be achieved utilising the collected novel real images (recordings) and also the previous real images (recordings). At the same time, testing the NN-KU and NN-UK transformation units 700', 700'' in order to establish whether they regain the diagnostic value for the novel images (because of the novel character, the diagnostic value can be lost, the transformation may be required to regain it) can be performed with the help of pseudo images generated by the auxiliary unit 300 (because, like the basic ROC analysis, the additional ROC analysis required for this can be performed utilising these).

As a further summary it can be concluded that the present embodiment preferably allows that a trained and deployed system can be utilised by the user by different circumstances, e.g. in case of a modified examination protocol, collimator or isotope (see above). Thereby, the problem mentioned in the introduction—posed by the modification of the examination protocol—is solved.

The configuration of the system according to the invention therefore preferably allows that—by applying the trans-training illustrated in FIG. 8 and the ROC analysis based on images generated by the auxiliary unit—medical supervision can be ensured without there being a need to bring away the novel images (for reprogramming the system with a servicing) from their location of use, which would involve legally complicated procedures, i.e., trans-training can be performed onsite (on the premise; utilising data recorded there and not going out from there, cf. FIG. 8), enabling the system to adapt to the novel images in such a manner that it can work at medically correct, known and accepted error rates, i.e., it is medically verified thanks to the verification of the diagnostic value.

In the following, a brief description of the so-called "federated learning" (or "collaborative learning") approach will be provided. This is a machine learning framework wherein a machine learning algorithm is trained with the help of decentralised terminal devices using local data, without making accessible the local data to other terminal devices. The approach based on "federated learning" therefore allows the construction of a common, robust machine learning model without sharing the data, i.e., allowing data protection measures.

For an example of the "federated learning" approach see the NVIDIA Clara framework (https://developer.nvidia.com/blog/federated-learning-clara/).

According to the invention, therefore, like in the case of "federated learning," there are preferably no legal/ethical difficulties because patient data are not relocated (brought away), but they are only utilised locally. According to the invention, furthermore, the diagnostic value of the system trans-trained at the user's site is preferably preserved (see above). The invention therefore realises a legal/ethical solution of the "federated learning" type (it may apply "federated learning" for pre-training certain units), with the added advantage that it also assures the preservation of diagnostic value.

According to the above, therefore, the embodiment of the invention illustrated in FIGS. 8-10 relates to a configuration method adapted for configuring the system according to the invention in case of issuing a discriminability warning (by the discriminator subunit), wherein, by collecting a plurality of discriminability warnings, a plurality of medical images are applied before issuing the first one of the discriminability warnings as first type medical images and a plurality of further medical images having discriminability warnings are applied as second type medical images. In the embodiment according to FIG. 8, the previous images (first type) and the novel images (second type) correspond to these.

Typically, after a configuration or other modification—which changes the character of the image—the system immediately detects by the discriminator subunit thereof that it receives images with changed character, so it issues the discriminability warning for them. The images before the first of such warnings are the first type medical images, which can be handled on the basis of the training so far of the system, while the images having a discriminability warning are the second type medical images. Because such medical images start to arrive at the input due to the above-mentioned modification, if a series of such images has started then it can be expected that images of this type will be arriving (i.e., these images typically arrive one after another as if in a series because the modification triggering them has already happened). However, if an image without a discriminability warning is received, that particular image will not be utilised for the method described below.

As it is also referred to below, the configuration method is performed applying an embodiment of the system which comprises the annotator unit adapted for generating an annotated image on the basis of the processed image, and the ROC unit adapted for determining an AUC parameter characteristic of the diagnostic value (for carrying out the configuration method the ROC unit is needed, the operation of which in turn requiring that the annotator unit is included in the system downstream of (after) the processing unit).

The configuration method according to the invention comprises the steps of in a transformation-training step, a first transformation unit (this is e.g. the transformation unit 700') adapted for transforming the respective first type input medical images is trained, applying configuration training with the help of the plurality of first type input medical images and the plurality of second type input medical images, and a second transformation unit (this is e.g. the transformation unit 700'') adapted for transforming the respective second type input medical images is trained, wherein the transformation carried out by means of the first transformation unit is adapted for eliminating discriminability of the first type input medical image from the second type images, and a transformation carried out with the second transformation unit is adapted for eliminating discriminability of the second type input medical image from the first type images (the role played by the transformation units 700', 700" are specified here; they are trained for performing a transformation adapted for removing discriminability—depending on the direction of the transformation—i.e., to obtain such images from the previous images that cannot be discriminated from the novel ones and vice versa), in a first diagnostic value verification (checking) step, steps of joint training steps are performed on joint-training auxiliary pseudo images originating from the auxiliary unit such that the joint-training auxiliary pseudo images are transferred to the processing unit being subjected the first transformation unit to them, and, for each of the joint-training auxiliary pseudo images a second lesion location data packet determined by the successive application of the processing unit and the annotator unit, and a respective first lesion location data packet corresponding to each of the joint-training auxiliary pseudo images are transferred to the ROC unit, and by determining the AUC parameter by means of the ROC unit, preservation of the diagnostic value is checked, wherein in case preservation of the diagnostic value can be established, a signal related (relating) to unchanged further usability of the system is issued, or, in case preservation of diagnostic value cannot be established, then in a second diagnostic value verification step, the steps of the joint training are performed on the joint-training auxiliary pseudo images originating from the auxiliary unit such that the joint-training auxiliary pseudo images are transferred to the processing unit subjecting the first transformation unit and to the second transformation unit successively to them, and, for each of the joint-training auxiliary pseudo images a second lesion location data packets determined by the successive application of the processing unit and the annotator unit, and a respective first lesion location data packet corresponding to each of the joint-training auxiliary pseudo images are transferred to the ROC unit, and by determining the AUC parameter by means of the ROC unit, preservation of the diagnostic value is checked (this is being checked here for the second time due to the two diagnostic value verification steps; they can be differentiated applying attributes "first" and "second" if necessary; as described below, the verification of preserving the diagnostic value is performed identically in both cases), wherein in case preservation of the diagnostic value can be established, then the system is configured by include the second transformation unit upstream of the processing unit for transforming the input medical image (see the medical images 825 and 830 in FIG. 10) for the processing unit (by including upstream of the processing unit 100 it is the second transformation unit 700" that will receive the medical images functioning as the input and it will then forward transformed version to the processing unit 100), or in case preservation of diagnostic value cannot be established, then a newly training warning indicating necessity of newly training the system is issued.

In the first diagnostic value verification step, if the preservation of the diagnostic value can be established, then no action is needed, the system can operate in an unchanged form because the novel images do not modify the diagnostic value.

However, if the preservation of the diagnostic value cannot be determined, then the second diagnostic value verification step is performed to investigate whether the transformation (cf. FIG. 10) can be applied during use, or it is necessary to newly train the system.

If preservation of the diagnostic value cannot be established in the second diagnostic value verification step, no configuration of the system is carried out as opposed to the above point that corresponds to the case of preserving the diagnostic value. In this case, according to the above, newly training the system is inevitable, i.e., the discriminability of the novel image cannot be remedied by transformations applying the above-described transformation units (i.e., the further use of the system in its current training state cannot be recommended, even with the application of a transformation).

The preservation of the diagnostic value can be checked by comparing with the AUC parameter value that previously characterised the system, and—analogously to the embodiment illustrated in FIG. 7—the preservation of the diagnostic value is determined if the expected value of the new AUC parameter does not yet differ from the previous AUC parameter value by an extent greater than the deviation of the AUC parameter corresponding to the previous AUC parameter value (i.e., it is typically not reduced by an extent greater than that, in other words, the change is not significant).

In order to perform that, the AUC parameter value achieved by joint training is determined (in relation to that, reference is made to the discussion above, in particular to the stopping of the joint training), i.e., the steps of the joint training are carried out analogously to the above-describe case, in order to obtain the AUC parameter characteristic of the transformed system for a comparison with the AUC parameter value of the original system.

If the modification resulting in receiving novel input medical images are only temporary, or such a modification is applied again, then the configuration method is able to switch back, or an even further transformation can also be applied as follows:

by applying a further transformation, or optionally, switching back can also be performed by removing the NN-UK transformation unit 700" included in FIG. 10 (this option can be chosen when we switch back to the original).

In the first case (applying further (additional) transformation) it can be set that during operation the novel images do not trigger the discriminator unit to give a warning—for example by including the inverse transformation also upstream of the discriminator unit, like it is included in FIG. 10 before the processing unit 100 —, however, if such images are received that are even "more novel" in comparison to the novel images, then another discriminability warning will be received since difference with respect to the novel images will be detected (experienced). Such a further transformation can in principle also be applied for backward transformation into the previous images.

A condition for the transformation can be the reception of at least a predetermined number of second type (i.e., novel)

images. This can be a predetermined minimal transformation database image number. Such a threshold value can be the reception of 100, 500, or 1000 novel images. A condition can also be provided for dealing with the presence of novel images. For example, it can be prescribed that until at least 10 or 50 novel images are received, the transformation will not be activated, i.e., the configuration method will not be started. This can be a minimum novelty image number.

Another preferable application of the invention can be a comparison-evaluation method, with the help of which the physician making medical record can more easily compare the earlier structured medical records (stored in a database) pertaining to a given patient with the results currently recorded and processed in the above-described manner. This presents the physician with those lesions/structures (i.e., other structural differences)—expediently by displaying them on the graphical display of a computer—that have appeared or disappeared with respect to the previous images. Thus, the physician making medical record is provided with a tool that aids patient tracking (disease tracking) effectively and accelerates and alleviates the medical record-keeping process (in relation to that, see the description above of the image database 575 related to the treatment of the annotated images 640).

An image recorded later of a given patient will typically not result in a novel image (see also below). Expediently, the old and the new images are processed according to the invention, and it is assumed that the recording protocol etc. are also identical. This is of course not trivial, because the camera might have been replaced (for example, the hospital received a new one), in which case the warning illustrated in FIG. 5 can also be applied.

The invention may preferably also provide such a tool that associates certain annotated lesions/structures with anatomical locations, for example in the case of bone scintigraphy images, with a bone model, and thus it is able to display the number of abnormal, or potentially abnormal accumulations, and/or—by examining them in the above-described manner—their changes.

The system according to the invention further comprises some type of image recorder, for example (at least one) gamma camera, a SPECT apparatus or PET apparatus, a CT or MRI apparatus, or a multi-modality apparatus. In lack of an image recorder device—i.e., in case the invention does not comprise that—the input image is simply play a role of the input. As a matter of course, the system preferably also comprises a computer wherein the methods presented above are implemented in CPU, GPU, FPGA, or any other suitable computing means.

In the following, the specific features of certain components are described in detail—up until the summary included below—for an application according to a concrete example (in the present description, it is called briefly an "example," or more lengthy, an "example described in detail"), for specific components and measures the specialities of these in the application according to the disclosure. In certain cases, these remarks can be valid for other applications, or can be generalised, mutatis mutandis, for other applications, i.e., they can be interpreted in a more general fashion than is given in this description.

In the example included below, the chosen modality and application: planar bone scintigraphy, i.e., a planar whole-body bone examination (anterior and posterior) recorded utilising a dual-head gamma camera (SPECT apparatus). Accordingly, certain features described below are related to this application.

The medically verified system realised by the invention preferably provides important information improving the reliability of the medical record for example for the descriptive part of a medical record written by a radiologist that is particularly useful for structured medical record-keeping and patient tracking, by indicating (certain advantages may also present themselves in a more general fashion):

1. Where the different from normal accumulations—generally: lesions—can be found in the image.
2. To what category these accumulations can be classified.
3. Preferably, the accumulations are counted, and their count is specified, optionally assigning them to anatomic structures (structured medical recording)
4. The physician making medical record is enabled to utilise this information for patient tracking and for evaluating the therapeutic process (based on the changes of numeric indicators, the treating (attending) physician will be able to assess them, see the description included above on the CAD—computer aided diagnosis—approach).

According to the above, therefore, the invention is adapted to provide additional information aiding the making of a diagnosis: it preferably specifies where the lesions can be found and the types of them. It offers the physician to investigate the results and to accept or revise them.

The configuration and operation of the image processing, annotator and auxiliary components mentioned above will now be described in detail in relation to a planar bone scintigraphy application example, also addressing the ROC unit as an additional component (these components are introduced in points I-IV below, information on each component is included after their name).

I. Image processing component: in this application, it is implemented by an artificial intelligence-based noise filter utilised for filtering planar images. A CNN (convolutional neural network) implementing a typical autoencoder, typical topology: U-NET (see for example: https://en.wikipedia.org/wiki/U-Net, and http://stanford.edu/class/ee367/Winter2019/dua_report.pdf).

An unlimited number of images with different statistical properties can be generated from a given planar scintigraphy image recorded applying a medical protocol specifying a normal examination time and injected activity. In the case of planar bone scintigraphy, a considerable number of factors affect the measured image quality. It may depend on the quantity of injected radiopharmaceutical, on the waiting time (uptake time), on factors determining the accumulating in the patient's body, or on the imaging duration. It is thus difficult to determine the statistical properties of the images generated applying the—often highly different—medical protocols, so it is more worthwhile to train a general neural network wherein the images are produced by means of various, real applied recording protocols resulting in images with even significantly different statistical properties.

In the present example the following implementation has been applied. Physician-annotated, anonymised anterior-posterior bone scintigraphy images were utilised as a starting point. The images were pre-sorted such that they include images of patients of different sexes with different body-mass indices, healthy images (not showing different from normal accumulations) and images showing different from normal accumulations. Each image was resampled based on a binomial distribution, artificially generating such noise-amplified images that have characteristics of images taken at half, quarter, eighth etc. of the original recording time or injected activity. By subtracting this degraded image from the original image, an improved-statistics sampling that is independent of the original one can be obtained. The purpose of the neural-network filter to be trained is to form a relationship between the two generated images.

In the example, we have found that the most preferable metric to be included in the loss function for training the CNN with a U-NET topology was the L1 metric. In the course of the training of the neural network, this metric yielded homogeneous, sufficiently structure- and edge-retaining results. The final output of the U-NET topology network utilised as a filter is an image (the filtered image). For the input of the network images with artificial noise are added, the expected output being a "smoothed", image having enhanced contrast that is similar to its low-noise counterpart (cf. FIG. 1).

As a result of joint training, the behaviour of the filter changes, i.e., it is less prone to remove from the filtered/synthesised image the real, different from normal accumulations, and it is expected that it locates false positive accumulations with a reduced probability, in spite of the fact that based on the local noise structure of the noise input image this is probable.

Figure 11A:
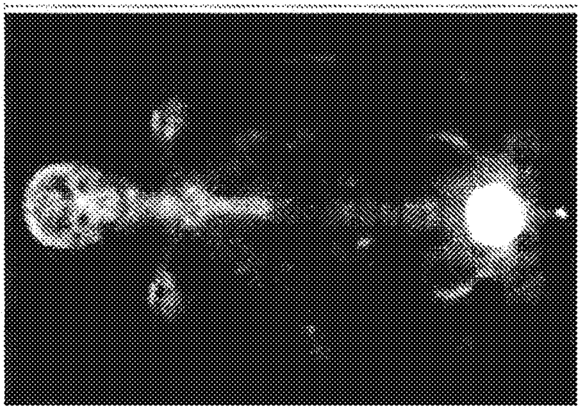
FIGS. 11A-11D illustrate visualisations and noise-reductions according to exemplary applications applying different samplings.
Figure 11B:
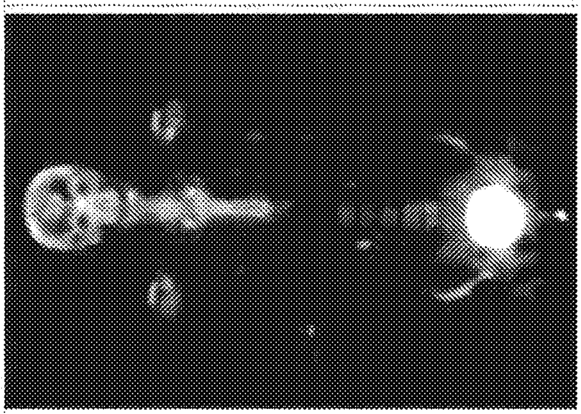
Figure 11C:
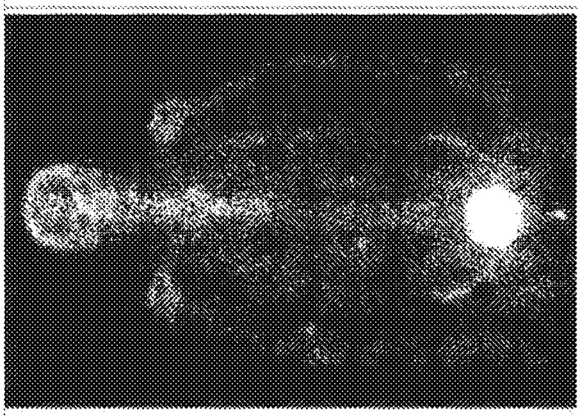
Figure 11D:
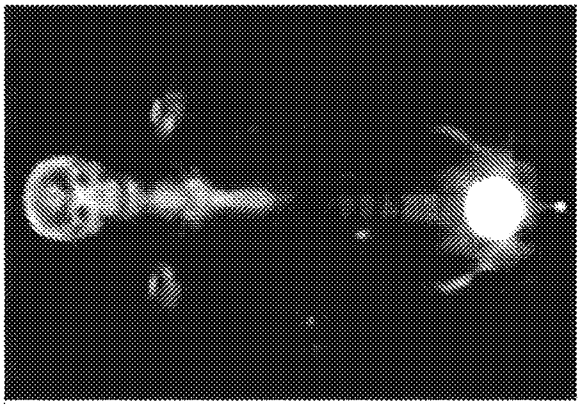

FIG. 1 and FIGS. 11A-11D relate to the schematic logical diagram of the noise filtering neural network and the generated result, respectively. FIG. 11B shows a filtered image that was obtained from the noisy image shown in FIG. 11A (in this case, a static image) applying the NN filter; FIG. 11D was obtained from FIG. 11C applying the NN filter. In FIG. 11C, the sample time (examination time) has been reduced with respect to FIG. 11A, so the noisy images (pre-filtering or starting images) thus obtained are more noisy compared with the "normal" noisy image (i.e., an image recorded with normal sample time) shown in FIG. 11A.

In the filtered figures (FIGS. 11B, 11D) there can be observed that the deterioration of quality is not as high as in the case of the noisy figures (we refer also to FIG. 7, in which it comes up that in the invention, preferably the diagnostic value of images with more noise can be examined). It is, furthermore, noted that here that it is a character of the training that the artificially deteriorated images are paired with images having good statistics. During operation, the system will of course have to deal with factually (really) noisy images instead of receiving an artificial image.

In the image with "⅛ statistics" (e.g. the image corresponding to ⅛ of the measurement time) the noise structure that can be seen on the right side of the ribcage does not produce a false lesion in the de-noised/synthesised image shown on the right (in FIG. 11C this corresponds to the left side of the figure showing signs of enhancement (intensifying), accumulations, however, in FIG. 11D no accumulations can be seen after applying de-noising; this is meant by stating that the noise has not introduced false accumulations).

II. Annotator: As with the previous component, the chosen application is planar bone scintigraphy. The network applied for implementing annotation is preferably CNN, for example with a U-NET topology.

In this example, during the generating of the training database necessary for annotation, the annotation-performing physician:

marks the location of the detected accumulations;

does classification: for example, location of injection, normal accumulation in a joint, clearly imaged different from normal accumulation, uncertain different from normal accumulations, other uncertain accumulation.

With the help of the above, the system can be trained such that its annotation module can adequately perform annotation and can display all these in the annotated image. Accordingly, in the present example the annotator is also trained for annotation, and at the same time in line with the annotation process described above, the annotator will become able to determine the second lesion location data packet (also applying classification therein), because it receives in the training information related to this.

FIG. 12 shows such a medically annotated and classified image, that is, an image for which annotation and classification has been completed applying the system according to the invention, where there are marked a location 900 of the injection, a location 905 of the normal accumulation in the bladder, locations 910*a*-910*g* of normal accumulations, locations 915*a*-915*b* of different from normal, presumably abnormal accumulations (they can be grouped to correspond among the safely identifiable lesions), and locations 920*a*-920*b* of uncertain different from normal accumulations (these latter can be grouped to correspond among the uncertainly identifiable lesions).

In the example illustrated in FIG. 12, annotation also perform classification. The training images are fully annotated and marked by the physician, assigning a category to each designated accumulation. Preferably, the annotator will then be trained based on this, and it will also perform classification. In addition to training the system what is different from normal (lesions), but also what is normal (negative regions).

FIG. 12 illustrates the output of the trained annotator. In addition to performing "mapping", the annotator may also help in visualising the differences between the previous and current examinations for the same patient, i.e., it is able to compare the current and previous examinations to assist (aid) in making the diagnosis and determining the therapy. Aided by the invention, the physician recognises what is different from normal (the different from normal accumulation can be for example an inflammation or metastasis). Thereafter, based on his/her experience and on earlier medical records, the physician gives an opinion, i.e., makes the diagnosis.

In the present example, annotation is performed applying a U-NET type network. The training required the prior annotation of the images such that the regions comprising normal accumulations and other negative regions can be selected. A negative region is therefore such a region where there are no different from normal accumulations. For example, the injected activity naturally accumulates also in the bones and joints, causing normal accumulations (such a region is for example the region of the femur that does not comprise any different from normal accumulations; the system is taught what is normal so that it is then able to recognise what is different from it).

In order to be able to work with the synthetisation of lesions by the generator subunit in the approach according to the invention, these need to be synthesised onto an image that does not comprise any other lesions, or, in a slightly different approach, all lesions present in the generated pseudo image have to be synthesised by the generator subunit. In such a way they will be suited for inclusion in the first lesion location data packet and can be applied for training the system effectively.

In relation to the present example, the following are noted with respect to the training process, more particularly to the joint training applying synthesised images. In the example, during the generation of synthesised images, lesion is synthesised to negative regions (i.e., to regions originally not comprising lesions, see also for example the Cycle GAN network, in particular FIGS. 17A-17F; in a certain case, a lesion can be obtained even by amplifying a normal accumulation), which synthesised images will serve during joint training as the input of the U-NET network to be trained. For training the annotator we must also be able to select such regions where a normal accumulation occurs.

Furthermore, in an example the U-NET network implementing the system is trained (i.e., the U-NET network is configured) such that the annotator is able to synthesise from these the original, "negative" images (see below a normal bone image 935, which is an image without lesions). Of course, this is only one of the many possible ways and approaches of annotation (like U-NET is exemplary for implementing the annotator and other components), i.e., the annotator can also be realised in a different way (the discussion above related to the bone image only illustrates the internal processes of annotator training, i.e., illustrate the applied "tricks").

When the system applying the network obtained in such a way was run (applied) for a complete image, we could find that the system is able to detect enrichments (uptakes; and structural accumulations of other type) in the image with very high efficacy (i.e., it can even detect all of them). This solution can thus be run for the "untouched", normal measurements; it will detect the typical accumulations in the shoulders, the location of injection, but also those accumulations that are presumably different from normal.

According to the above, in FIG. 13 the presently described portion of the example for the annotator's operation is illustrated. From left to right, FIG. 13 shows the following: an original image 930 (which is an input image for the annotator, i.e., it has already been processed by the processing unit), a normal bone image 935 generated in the annotator by the internal algorithm applied during training (which is therefore a "negative" image that does not contain any abnormal accumulations; in the case of a pseudo image the generator puts into the bone image the different from normal accumulations, the normal accumulations are also present in the bone image), and on the right a layer image 940 comprising the accumulations can be seen. The layer image 940 is adapted to provide a basis for identifying the places (locations) of accumulations, i.e., the relevant regions, in the annotator.

In the paragraphs above, therefore, an exemplary annotation technique has been disclosed. The normal bone image 935 is required because—by subtracting it from the original image 930—it allows the annotator to generate the layer image 940, which is therefore an image that comprises already isolated lesions. Accordingly, in this example the layer image 940 can be a representation of the second lesion location data packet (when the annotator is operated during joint training, i.e., this image is only an illustration of that; in such a case these are essentially lesion candidates that are all going to be transferred to the ROC unit in an embodiment not applying classification, of these the ones that finally do not prove to be lesions can be filtered out easier if classification is applied, see the discussion related to FIGS. 12-15 describing how we can get there), that can be compared during joint training with the accumulation layer image originating from the auxiliary unit (which in such a case also relates only to annotations), i.e., in general, with the auxiliary lesion image (in line with the above, as an alternative see also the description below related to FIG. 15).

Figure 14:
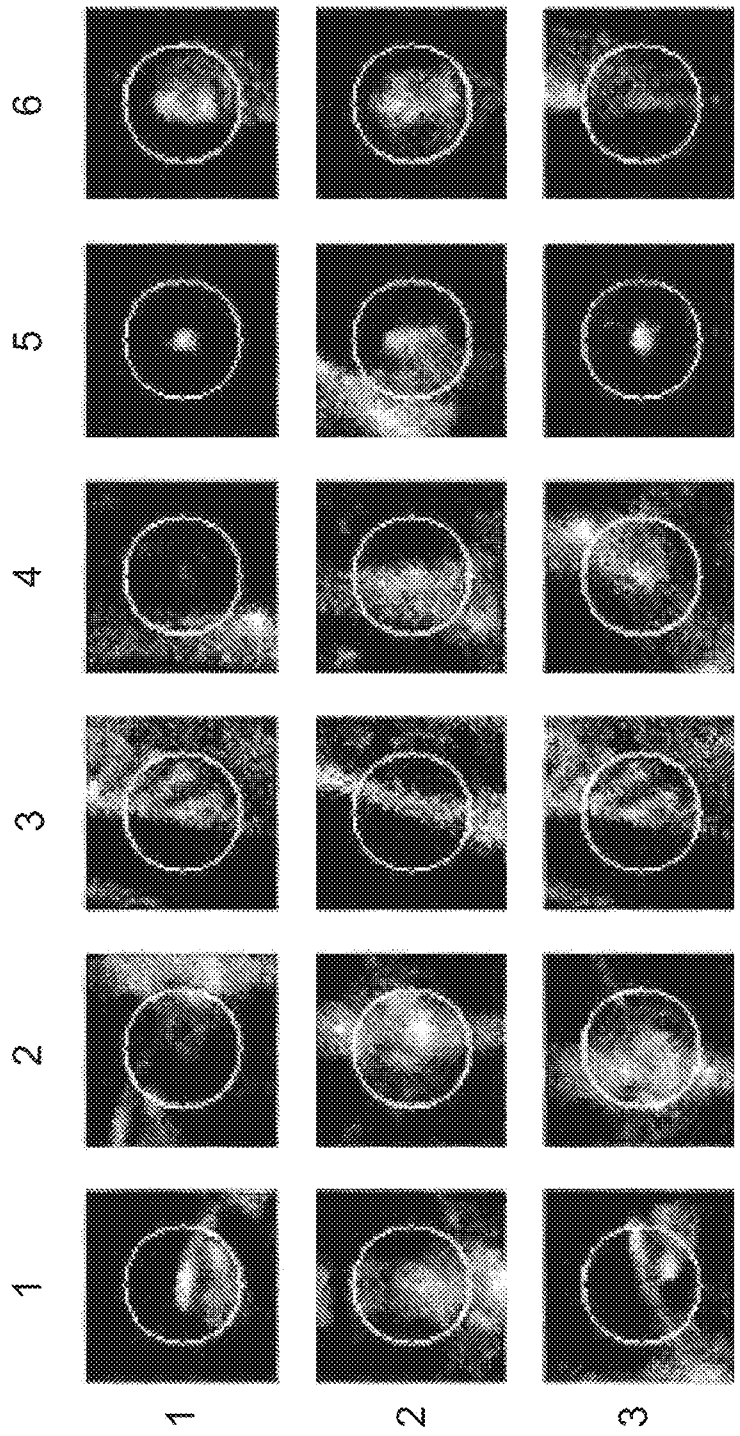
FIG. 14 shows details illustrating accumulations.

FIG. 14 shows partial regions identified on the basis of the accumulations. Each image (subfigure) shows an image segment being different from normal, and thus has been considered as suspicious. The classifier will decide based on these segments whether the accumulations identified in the previous step are normal or different from normal (and if different from normal, what type).

In order that the classification can be performed, it is also necessary to fully annotate/mark the training images—for example, by a physician—, and to assign a category to each identified accumulation. The annotator will then be trained based on these, and it will also perform classification.

Accordingly, the already separable (visually separate) regions found in such a manner can be considered as a (propositional) solution for marking target regions, see FIG. 14 that illustrates such selected regions. In the small-sized images of FIG. 14 the followings can be identified: parts corresponding to ribs (row 1, subfigure 3 and row 3, subfigure 3), to shoulders (row 1, subfigure 1 and row 3, subfigure 1) and parts corresponding to other accumulations (e.g. ankle). The aim of FIG. 14 is therefore to demonstrate the accumulations to be classified.

FIG. 14 shows such lesion candidates that can be found in the image identified as a lesion layer, however it shows them together with their environment, which can help in the classification. FIG. 14 is a result related to classification. By means of the classification, expediently a proposal about what can it be is given. The physician may check (verify) and modify this proposal.

In the images of FIG. 14 there are therefore suspicious image segments that have been found to be different from the normal. Based on these, the classifier determines whether what is picked up (enhanced) by the previous part is normal or different from normal (and, within that, what). The primary aim of FIG. 14 is to illustrate the accumulations to be classified. The annotation performed in the annotator according to the present example therefore is a two-step process: first, the critical regions (image segments) are to be found, and then they have to be evaluated.

The regions obtained this way (image segments showing for example a respective characteristic region of the body) can be preferably analysed applying classification neural networks, with the help of which it is possible to assign particular classes to the regions, like it was done in the case of FIG. 12. This allows us to show the segments, i.e., the lesion candidates, coloured according to classes; see FIG. 15 where the colours applied in the right subfigure of FIG. 15 can be understood based on the reference signs applied to the same accumulations in FIG. 12 even in the case of a visualisation without colours. FIGS. 13-15 therefore illustrate the process leading to the results illustrated in FIG. 12 that is identical to the right subfigure of FIG. 15 (with the difference that the two figures are mirror images of each other). Based on the notations applied in FIG. 12, the left subfigure of FIG. 15 can also be understood, in which it can be seen without showing colours, i.e. in greyscale, which accumulations are depicted in colour (with the same colours as applied in the right subfigure of FIG. 15), it can also be seen which accumulations are shown in white, these are already not marked in the right subfigure (see also below).

Accordingly, in the present embodiment an annotator unit generating the annotated image by performing identification and classification in the processed image is applied. In addition to that the annotator unit identifies the critical locations on the input image fed to it (the aim of training is that it can identify those locations that are also included in the accumulation layer image, i.e., that the ROC unit receives from the generator subunit). Moreover, in this embodiment a classification is also applied to the identified accumulations, for example they are grouped into categories described in relation to FIGS. 12 and 15. To facilitate operation of the ROC unit, it is required that the annotator identifies entities evaluated as lesions, however, different weights can be applied for marking the uncertain and the safely marking of accumulations (see the "safely and uncertainly identifiable" groups). This allows us for example to record multiple points of the ROC curve.

An important feature of the invention is therefore that the system classifies certain identified accumulations differently after the ROC information feedback is performed, subsequent to the completion of joint training—which follows pre-training—, i.e., it is able to find the relevant abnormal accumulations with improved efficacy. This is also illustrated in FIG. 15, where not every one of the coloured, i.e., classified accumulations shown on the left (an accumulation image 945 on the left) appears in the final classification image shown on the right (a classification image 950 on the right, i.e., the image produced as a result of the classification that, in accordance with the above, has the same content as FIG. 12). The result of the classification is marked with colours in the accumulation image 945 in correspondence with FIG. 12. Thus, in the accumulation image 945 and—which are present on it—also in the classification image 950 in a corresponding colour:

- a location 905 of the normal accumulation in the bladder is shown by blue,
- locations 915*a*-915*b* of the expectedly abnormal accumulations seen in the middle are shown by red,
- locations 920*a*-920*b* of uncertain different from normal accumulations are shown by yellow,
- locations 910*a*-910*g* of the normal accumulations in the joints are shown by green, and
- other accumulation locations that cannot be grouped into any one of the above groups (these are therefore the accumulations which are not different from the normal; accordingly, they are not shown in the classification image 950), and location 900 of the injection are shown by white (these are thus entities different from lesion, like the members of the classes with above colours different from the red and yellow groups).

On the left of FIG. 15 there are denoted such regions wherein the above-described method (neural network) identified suspected accumulations different from normal (this image—like the layer image 940—was obtained by subtracting the bone image generated in the annotator from the original image). Based on further analysis, however, as a result of joint training not all such regions prove to be different from normal in the final output of the annotation process (that is, on the left of FIG. 15 there can be found such lesion candidates which during the classification process do not prove to be lesions; see also the description below in relation to determining the second lesion location data packet).

In sum, therefore, the colouring applied in FIG. 15 (see the reference signs in FIG. 12) is already a result of the classification. It can be seen that not every one of the spots marked in the accumulation image 945 is included (i.e., encircled) in the classification image 950. These have been considered—for example based on their environment ("context")—as normal accumulations.

In the course of a classical ROC analysis (i.e., if it would be applied in the invention) we would specify a threshold value that would be in proportion to the size/intensity of a difference that would be considered as different from normal. The currently applied point of the ROC curve would be determined by the changing this threshold value (as an internal parameter). Such a threshold that determines the trade-off between sensitivity and specificity is a unique character of every medically relevant examination.

It is important to emphasise—and it is also characteristic of the significance of the advantages provided by the invention—that, as a result of the feedback of the ROC information the optimum of this trade-off is selected (recognised) intrinsically (i.e. within itself) by the system according to the invention. As a result of this, not every one of the differences depicted on the left of FIG. 15 appears in the right of the figure—which can be a depiction of an annotated image obtained as a result—as a structural difference to be shown, i.e., the system performs an effective selection (in this case, marking—in an annotated image constituting a preferred output—the detected lesions and other accumulations).

To put it in another way, the invention is more effective than known systems in finding the entities that are important to find, facilitating the work of the evaluating physician by providing them annotation results obtained this way. Based on the preferably applied classification, according to the invention we not only intend to shed light on the locations of the different from normal accumulations (generally: lesions), but a recommendation is also given to the physician what can be the given accumulation (in general, what type of structural difference it corresponds to). Besides that, after receiving the evaluated (annotated) result prepared for her/him, the physician can check (verify) and modify it.

As an alternative to the representation of the second lesion location data packet by the layer image 940 shown in FIG. 13 (without applying classification), the second lesion location data packet can also be produced applying classification, in which case the—for example, image—representation thereof can be conceived based on the accumulation image 945 and the classification image 950.

In such a case, therefore, the second lesion location data packet can essentially be considered to comprise the accumulations—i.e., data related to the that—which are shown in the classification image 950 in yellow and red, which are abnormal accumulations, i.e., the lesion candidates that proven to be lesions. However, it comprises only the abnormal accumulations (lesions), that is, not the skeleton that is present as a background (i.e., it can be considered to comprise, in a filtered manner, essentially the islands visible in the accumulation image 945). As it was referred to above, the auxiliary lesion image originating from the auxiliary unit preferably already comprises information corresponding to thus filtered portion of the accumulations (generally, structural differences); classification (that is, some kind of filtering) is applied in the annotator such that these can be compared in the ROC unit. However, the diagnostic value is assured by the ROC unit both with and without the application of classification.

It is important to note in respect of the annotator that the physician's task in relation to the invention typically consists of two parts. Firstly, the physician can detect in a medical record what is that is different from normal and can describe them. This step can be aided by the system according to the invention. This is followed by the physician giving his/her opinion based on expertise (knowledge), and optionally, on earlier medical records. In the framework of the invention no interference in the latter step is intended, i.e., in accordance with the above we intend to aid the evaluating physician in detecting the accumulations different from normal (generally: lesions).

The result can also be compared with the results obtained for earlier images (scans, recordings)—if they are available—if any differences are visible with respect to them. It can be determined, for example, whether a therapy was successful or not, or the information can be applied for suggesting a new therapy.

III. Auxiliary unit: in relation of the given example, the role of this component is to generate artificial, synthetic images based on an image database comprising normal and different from normal accumulations, which synthetic images are characterised by that they are indistinguishable by a trained physician from images of real recordings; and also, to generate the lesion layer image that form the input of the ROC unit.

Figure 16:
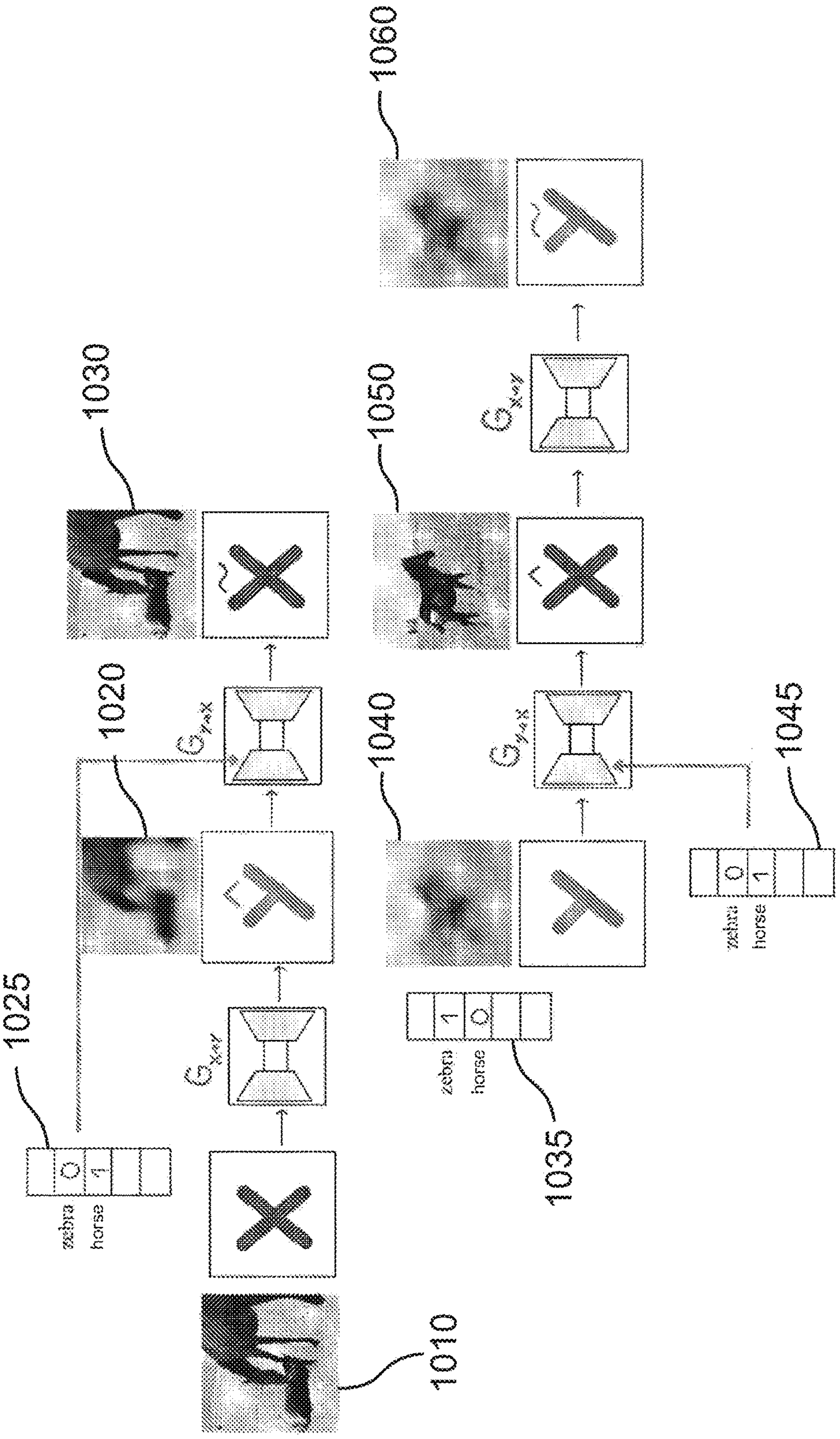
FIG. 16 is an illustrative flow diagram corresponding to an embodiment of the invention.

In the present example, during the training process of the auxiliary unit a special CycleGAN neural network is constructed. The CycleGAN network is adapted for providing a transformation between two databases of unpaired images having features classifiable into distinct groups; by training it, transformation operators transforming one set of the images into the other are produced. The parametrised CycleGAN neural network applied in this example is based on Gx→y and Gy→x operators, an implementation of which is illustrated in FIG. 16 (furthermore about on CycleGAN see for example: https://towardsdatascience.com/cyclegan-how-machine-learning-learns-unpaired-image-to-image-translation-3fa8d9a6aa1d). The present CycleGAN approach applies different operators than in FIG. 8 that also have different roles.

In the case of the present example, lesion generation in the accumulation layer image is performed in the auxiliary unit (component) by means of a parametrised, super-resolution CycleGAN network. The Gx→y network of this neural network system is trained for synthesising a lower-resolution image Y from an image X having good resolution. The Gy→x operator of the CycleGAN network is trained to perform the inverse operation, i.e., it generates an appropriately high-resolution image from a lower-resolution image representation Y. The L1 norm is applied in the loss functions of the generator and discriminator networks.

In the system illustrated in FIG. 16, the operators (networks) Gx→y and Gy→x are described with images comprising horses and zebras. The images of horses and zebras are included here in relation to the corresponding CycleGAN application for the sake of demonstration enabling better understanding; according to the example, in a real application bone scintigraphy images comprising normal and different from normal accumulations are applied, or, in the case of a different application, other images comprising normal and different from normal accumulations are applied.

From the interim low-resolution showing image representations marked with ^ in the top row (first, second, and third low-resolution images 1020, 1040, 1060; the latter is included in FIG. 16 only to illustrate the cyclical nature of the process and it is irrelevant from the aspect of the present application) such high-resolution images are synthesised, depending on the parameter value (i.e., second and third high resolution images 1030 and 1050 are obtained by synthesisation), which are most similar to the corresponding training image database (see first and third parameter blocks 1025 and 1045 fed into the operator Gy→x that are adapted to specify that a horse image is to be synthesised; the second parameter block 1035 corresponding to the second low-resolution image 1040 indicates that the image in question shows a zebra).

The transformation operator is thus a parametrised operator. The operator Y→X generates a sharp image from a low-resolution image representation. The kind of this sharp image is significantly affected (i.e., is essentially determined) by the parameter. As a result of the training, with a parameter value "horse=1" the operator will generate images similar to the group of horses, while with a "zebra=1" value images similar to the group of zebra images will be generated. That is, we do not know how the patterns specific to horses and zebras are introduced, but the weights of the neural network implementing the transformation (or other machine learning algorithm or machine learning based operator; as with many other units, this one is also described with a neural network but can be generalised similarly to the others) are adjusted such that the neural network synthesises images similar to horses or zebras.

It can be observed in the synthesised images, for example in the bottom row of FIG. 16, that in the case of the horse shown in the high-resolution image 1050 not only the stripes have disappeared compared to a zebra, but such an image is produced wherein the synthesised horse is as similar as possible in all details (body spots, mane) to the horse images of the image database. The same can be observed in the top row, while therein can also be seen an initial first high-resolution image 1010, to which the second high-resolution image 1030 is of course very similar, this however only proves that the transformation works well—thanks to the appropriate training—because the image 1030 is a synthesised image.

Referring to the analogy, like a given texture on the bodies of horses and zebras, the lesions also show up at specific locations in an image (at some portion of the skeleton). This is because a neural network and an appropriately high number of training images are required such that the network can learn that lesions do not appear at arbitrary locations. Analogously to that, the stripes of a zebra also do not appear at arbitrary locations and they are not of arbitrary kind: for example, there are no chequered zebras, the stripes always "follow" the surface of the animal's body, they usually do not undulate, etc. Applying this method, therefore, like in the exemplary case involving horses/zebras, the neural network will learn non-local type structures also in the case of the lesions.

In this example, the CycleGAN is applied for implementing the functionality of the auxiliary unit, so we will be able to generate images comprising normal accumulations as well as images comprising different from normal accumulations (the generation of horse or zebra features from the low-resolution images by the Gy→x can be considered analogous with synthesising normal or abnormal accumulations into an image). In this example, one image is transformed into the other by the simultaneous operation of two operators, i.e., these operators also undergo joint training.

A similar transformation is carried out in the case of horses and zebras like in the case of locating lesions. Like the images showing lesions, each image showing a horse is different from every other image. We can only determine which pixels belong to the horse and which belong to the background thanks to the "neural network" of our eyes/brain. Similarly, there is no difference in complexity between the bone scintigraphy application and the transmutation task involving horses/zebras.

Turning now to the present example, in the real clinical application the database comprising horses is replaced with bone scintigraphy scans containing only normal accumulations, while the image database of the zebras is replaced with assorted, different from normal images of an image database (e.g. showing various bone metastases); the CycleGAN will be applied for performing transformation between these. The extra information included in the parameter blocks 1025, 1045 (which constitutes an input for the Gy→x operation) may be of many kind. It can therefore indicate/include (the first bullet point below specifies its present function as indicated in FIG. 16; other points indicate that further information can also be applied at this point, either as extra or alternative information)

- the class into which the given image is grouped (this is compulsory comprised), i.e., healthy/diseased image, more precisely, image comprising normal as well as different from normal accumulations;
- a lesion-marking matrix (or simply lesion matrix) that specifies in the intermediate, reduced-resolution image representation the location at which we intend to synthesise a lesion, or, instead of this:
- structural medical record information, which specifies the anatomical structure to which we would like to synthesise a different from normal accumulation (for example, the L1 vertebra);
- a number or vector generated by a random number generator (it can denote the intensity of the lesion and/or its location inside the anatomical structure).

As a result of that, such an image is generated, utilising the trained Gx→y and Gy→x networks as nonlinear image transformation operators, from an image comprising normal accumulations which image

- is similar to but is not the same as the initial image (for example the high-resolution images 1010 and 1030 in FIG. 16);
- comprises lesions at various (but realistic), locations, in real local structures (this can be analogous to the generation of high-resolution images 1050 in FIG. 16); and
- a layer image of the lesions is also produced (it is required for the ROC analysis and joint training).

The results of operating such a trained network—based on the network illustrated in FIG. 16—are presented in FIGS. 17A-17F in a bone scintigraphy application.

Figure 17A:
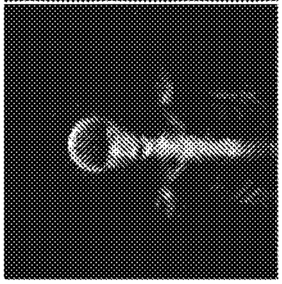
FIGS. 17A-17F illustrate various exemplary steps of lesion synthetisation.
Figure 17B:
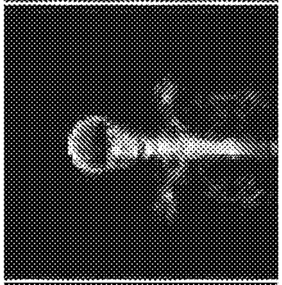
Figure 17C:
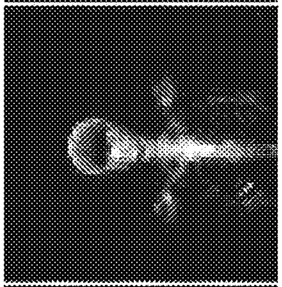
Figure 17D:
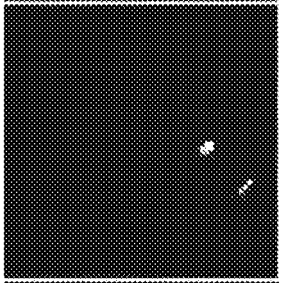
Figure 17E:
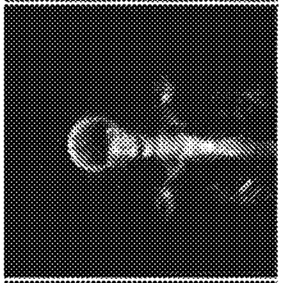

FIGS. 17A-17F show, from left to right: an initial image 960 comprising normal accumulations selected for the transformation (FIG. 17A), a representation of a low-resolution image 962 transformed utilising the Gx→y operator (FIG. 17B), an intermediate image representation 964 comprising different from normal accumulations specified by the parametrised lesion matrix 966 (FIG. 17C, wherein the activity of the left ribcage and the sternum has been modified with respect to FIG. 17B), and the lesion matrix 966 (FIG. 17D). The result image is an image 968 comprising different from normal accumulations that has been restored to the original resolution applying the Gy→x operator (FIG. 17E), and the corresponding lesion layer image 970 is also shown (FIG. 17F, where the portions associated with the accumulations are located in correspondence with the content shown in FIG. 17D—a point-like feature and another one to the left of it and below it as seen in the figure—as FIG. 17F only shows the lesions, it can be an example for the auxiliary lesion image).

The following additional observations can be made in relation to FIGS. 17A-17F: The lesion matrix 966 shows the shape (location) of the lesion to be placed onto the low-resolution image 962. Thus, a lesion with such a location needs to be synthesised (i.e., placed into the image 962). Thanks to the applied training, the lesion will be placed at the correct location (i.e., on the bone and not for example "in the air") by the neural network performing the synthesisation.

In this case, the location and the intensity of the lesions can essentially be chosen when accumulation is placed into the image 962, here a respective accumulation is placed on the ribcage and on the sternum. The network generates the image 968 corresponding to FIG. 17E. By subtracting from this the original image according to FIG. 17A, the layer image is obtained, i.e., FIG. 17F equals FIG. 17E minus FIG. 17A (i.e., in this case, the auxiliary lesion image—as the image representation of the first lesion location data packet—can also be obtained in this way, since an initial image comprising the normal accumulations is available).

The contents of the lesion matrix 966, i.e., the shape of the lesion to be placed is also determined by an algorithm (the neural network responsible for synthesis). This for example generates a random matrix (the lesion matrix 966) based on the low-resolution image 962, which matrix determines the location of the lesion. By placing the lesion into the image, the intermediate image representation 964 is obtained, from which the image 968 restored to original resolution is generated applying further steps of the algorithm. The image 968 is examined by the discriminator (discriminator subunit) at the last step of the synthesisation process, whether the synthesised image is appropriate or cannot be considered appropriate (i.e., if it differs—can be discriminated—from the real images).

As it is apparent already from the comparison of the lesion matrix 966 and the lesion layer image 970 (and also in the image 968 obtained as a result), the contents of the lesion matrix have not been carried over one-to-one into the image 968 (for example the intensity of the lesions have changed with respect to the lesion matrix 966). Accordingly, as with the example of FIG. 16, content change (in this case, the synthesisation of lesions) will not be local.

The concept behind FIGS. 17A-17F is only different from FIG. 16 in that the parameter is a matrix rather than a scalar. It is thus not a single number, but also specifies that where, what kind of the lesion should be located; the information provided by this modifies the image—either the entire image or only a portion of it—but the information will not remain local, for example the lesion will be introduced with varying intensity.

Figure 17F:
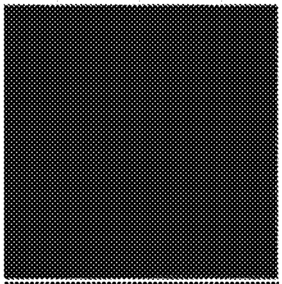

In the case of FIGS. 17A-17F, the GAN generator is applied for generating the parameter matrix (FIG. 17D; specifying the locations of the lesions), which is followed by the step of generating the pseudo abnormal image (FIG. 17E) and the layer image (FIG. 17F). It is noted that in the case of the G y→x operator the parameter can be a scalar, for example horse or zebra, but can also be an image matrix containing for 64*64 1 or 0 values. The process is therefore illustrated in FIG. 16 in a simplified way.

FIGS. 3A-3B and FIGS. 17A-17F (by the help of FIG. 16) illustrate two exemplary approaches to generating the pseudo images, and also illustrate the information that is available about the location of the lesions (in FIGS. 3A-3B, abnormal accumulations). The pseudo images and the lesions in them can also be generated in various other ways (if there are lesions in them, of course our aim is basically to generate pseudo images having lesions, but for example it can be advantageous from the aspect of training to have pseudo images that do not have lesions).

FIGS. 3A-3B and FIGS. 17A-17F illustrate that in these approaches the visual material related only to the lesions (that is, the visual representation of the lesions) is available. As it was also mentioned above, such cases are also conceivable wherein no image representation can be assigned to the first lesion location data packet determining the location of the at least one lesion possibly present in the pseudo image, or wherein such image representation is simply not assigned thereto, i.e., the first lesion location data packet is transferred to the ROC unit in a way other than an image representation (this may have arbitrary reason, but in certain cases such a representation can be obtained in this way which can be more effectively compared with the second lesion location data packet in the ROC unit). Based on the analogy of FIGS. 17A-17F, for example, the data packet can have a non-image (e.g., not specifically image or not exclusively image) representation which contains information on lesion location available in the form of a matrix, and in addition to that, information on the intensity of each lesion is also available.

Accordingly, even the lesion matrix—which is also generated by the generator subunit—also may be suited for being transferred to the ROC unit as a first lesion location data packet (i.e., the information included in FIG. 17D). However, the lesion matrix does not comprise information on the intensity of the lesions contained by the pseudo image. It is therefore more preferable to transfer to the ROC unit—as a first lesion location data packet—for example, the auxiliary lesion image illustrated in FIG. 17F.

In such a case the ROC unit is preferably able to fine-tune the comparison. This is possible because in case intensity data are assigned to the lesions of the first lesion location data packet, then for the examination of corresponding lesions the group classification of the lesion belonging to the particular intensity data can be taken into consideration. If, for example, a lesion in the first lesion location data packet has such an intensity that it only barely shows up in the image, and it is grouped as uncertain in the second lesion location data packet, then it is after all a detection that is correctly classified in the second lesion location data packet. However, for example a penalty will be given in the ROC unit if the first lesion location data packet contains a high-intensity lesion that is not found by the annotator in the second lesion location data packet (its presence in the uncertain group is considered an extenuating circumstance; however, accordingly, such a situation may also occur that the first or second lesion location data packet contains a lesion that has no counterpart in the other packet).

In an embodiment, therefore in the first lesion location data packet respective intensity data are assigned to each of the one or more lesion possibly present (the intensity data may also be called intensity information; such intensity data are applied for specifying the intensity of a lesion), respective classification (grouping) information is assigned to each of the one or more lesion possibly classified into the first annotation group and into the second annotation group, and the classification information is incorporated into the second lesion location data packet (i.e., in this way essentially the information specifying the group into which the given lesion has been classified by the annotator will be included in the data packet), and by the ROC unit, in the course of the comparison, for the one or more lesion possibly present in the first lesion location data packet and in the second lesion location data packet, the intensity data and the classification information, respectively, are taken into consideration.

Lesions may even have spatially varying intensity, which can also be described by the intensity data and, when a given lesion is being compared with the classification information for example an average value or other intensity parameter (e.g., maximum intensity) is assigned to it. Thus, this extra information can be taken into consideration also in this case.

In the approach according to FIGS. 3A-3B and FIGS. 17A-17F, therefore, an image representation is available regarding the lesion locations. In the approach according to FIGS. 3A-3B it is generated directly (as the images 315 and 340), while in the approach according to FIGS. 17A-17F it can be obtained with the help of the final image and the original image (by subtraction). However, with the machine learning algorithms (for example, neural networks) the lesions are not additively placed into the pseudo image (these are much more complex algorithms; instead, the initial image is transformed into an image that already contains the lesion together with its environment), but an image representation can also be obtained also in this approach (which does not involve the direct generation of the image representation of the lesion locations). Such a case is also conceivable where this cannot be obtained, for example if it is not generated directly, or the image prior to generating the lesions is not available.

In the example illustrated in FIGS. 17A-17F, an accumulation is marked on a structural element (for example, on a bone segment). The accumulation can also be placed onto the low-resolution image for example by a neural network that—on the basis of the physician-annotated/marked images—"knows" where the lesions are located, with what kind of distribution, and their typical sizes.

In addition to the exemplary solution described above, in other embodiments the auxiliary component can be implemented applying GAN systems (see FIGS. 3A and 3B) and other neural network systems, such as variational autoencoder-type solutions (see above).

In sum, it can be maintained that the horses and zebras are referred to for illustration only; in our example, they represent the group of images comprising normal accumulations and accumulations that are different from normal.

In FIG. 16 a system is shown, where the two operators, Gx→y and Gy→x, of the CycleGAN are trained to synthesise, utilising the two types of image database (horses—normal accumulations and zebras—accumulations different from normal), a horse in the case of a "horse" parameter and a zebra similar to the "zebra" group in case of a "zebra" parameter. In this case, therefore, the networks are parametrised, i.e., their behaviour depends on the parameter value. The operation of the generating is thus controlled by a single parameter. An extra parameter that can be specified is the type of the animal, which can be related to the "diseased-non-diseased/abnormal-non-abnormal" classification. The generated intermediate representation differs in a third property: blurry-sharp.

This solution also enables us to simply initialise lifelike lesions to anatomical structures, in varying number and with varying intensity, and thereby making it possible to generate images with different from normal distribution that include the widest possible spectrum of lesions (from the all-but-invisible to the markedly visible), i.e., images that are from a medical point of view essentially indistinguishable from the real images.

For this, a preferred solution is given by the utilisation of the above-mentioned "Super Resolution"-type networks (see also below). Naturally, the processes presented in FIGS. 3A and 3B and their arbitrary alternative can also be included here as the algorithm implementing the auxiliary unit. The essential feature is that the auxiliary unit also generates the layer image (generally: lesion image), so that way the "ground truth" is known for the ROC unit (for the results arriving from the annotator), and it is also able to plot the ROC curve, see above. In FIG. 16, therefore, a framework applicable in the auxiliary unit is illustrated in detail.

During operation the system needs low resolution images that are as similar to the training database corresponding to the parameter as possible, that is, the appropriate content goes (to the right place) onto the low-resolution image by means of this operation.

Preferably, two types of image database are required: one that comprises only normal accumulations, and another image group in which the physician has detected accumulations different from normal. The low-resolution representation can be generated simply from the image groups (in the embodiments according to FIGS. 3A-3B we start from a noise vector, noise image, while in this case from a low-resolution image). In this case, this super-resolution is essentially a preferable solution, an auxiliary functionality, which works in this case because the difference from the normal of the different from normal manifest themselves at the level of fine details.

FIG. 16 is thus adapted for illustrating the example. The horses and zebras can be replaced with any image classes, where replacing only one feature (replacing one type of animal with another of a similar type) is not sufficient for obtaining an image characteristic of the other class, as in the case of horses and zebras the body spots and the mane must also be modified.

The contents of the image are changed completely by the transformation, i.e., the low-resolution image is restored to the appropriate resolution such that the affected portions of the image (but the background, not specifically) will be similar to the target image database. That is, in addition to their stripes, zebras may have other features that are not "horse-like," and a lesion is also a more complex shape on an unchanging background.

This is important because it cannot be stated that the healthy patient images (images comprising normal accumulations) differ only in recorded activity from images of patients expectedly living with certain diseases (being different from normal images comprising for example bone metastases), since for example the differences in tissue structure and the typical locations of elevated-activity regions all correspond to such abnormal images and it is in the image sets as hidden information. The neural networks implementing the auxiliary unit have the character that these features do not have to be input (programmed) in a predetermined manner, but the network automatically recognise them and apply them in the synthesis.

In relation to FIG. 16 it is noted that in the embodiment according to FIG. 3A the generator subunit 350*a* operates in such a way that it "knows" the healthy images selected by physicians (a set) and is able to generate similar images from a random input (cf. the low-resolution horse-zebra images in FIG. 16).

In view of the horse-zebra analogy illustrated in FIG. 16 it is essentially possible to apply noisy and low-resolution images as a starting point. The images can be generated from noise (see FIG. 3B), i.e., it can be learned by the artificial intelligence (machine learning algorithm, for example neural network) implementing the generator subunit. This task is easier to perform if a healthy medical training image 310 database is available.

By analogy with the method illustrated in FIG. 16, in the case of FIGS. 3A-3B it can be considered as if the task was made easier, i.e., if the requirement was not the generation of any type of horse image that the system is able to transform into zebra images, only that the transformation (transmutation) can be successfully performed for the few thousand horse images that are available.

It is accordingly it is supported by the above and by other similar solutions that FIGS. 3A-3B and FIG. 16 give only present preferred embodiments of the auxiliary unit, i.e., other realisations thereof are also conceivable. In FIG. 16 a parametrised CycleGAN implementation is illustrated (that is, in the present embodiment illustrated by FIG. 16 the CycleGAN is applied in the auxiliary unit, as opposed to FIG. 8 where it is applied for performing the transformation between the previous and the novel images), with FIGS. 3A-3B illustrating a GAN implementation. In respect of the CycleGAN method, reference is made to the document cited above (Jun-Yan Zhu et al. Unpaired Image-to-Image translation using Cycle-Consistent Adversarial Networks (2017), arXiv: 1703.10593v7, 24 Aug. 2020). In FIG. 3*a* of this document there can be seen that according the solution shown in FIG. 16 two generators and two discriminators are included, i.e., four interdependent neural networks are trained simultaneously.

In FIG. 3B, subtraction is applied for deriving the healthy images (an analogous process is represented also in FIGS. 17A-17F). In the case of FIG. 3A there is no subtraction. This may be an advantage because in certain cases the non-healthy and healthy images cannot be subtracted from each other, i.e., the embodiment according to FIG. 3A also provides a solution for such a case. An example for such a situation is e.g. a CT scan, in which case a tumour will cause not only a modified absorption rate and in giving more light (showing higher absorption) but the structure itself may change because the tumour also transforms the surrounding tissues.

To sum up about the auxiliary unit, it can be maintained that in the case that it is GAN-based, the generating is verified by a single discriminator (or even separate healthy and non-healthy discriminators). Conversely, in a CycleGAN system (see above), there are already 2 generators and 2 discriminators, i.e., these have a more complex system. Systems of generators and discriminators that are even more complex than that can also be conceived.

The manner of obtaining synthesised images in a CycleGAN framework is also apparent from the related description included above. Accordingly, in addition to its application for the previous-to-novel image transformation illustrated in FIG. 8, the CycleGAN can also be applied for implementing the auxiliary unit, while the discriminator expediently applied therein can be utilised for implementing the discriminator subunit.

GAN substantially utilises one-direction generating, while CycleGAN applies a cyclical generating (in many cases between two groups, which can be a useful analogy here due to the healthy-abnormal). FIGS. 17A-17F can represent the only direction of the GAN, but they may also fit into the cyclical scheme of CycleGAN.

CycleGAN implements a generator that transforms one image to another, and it has the significant advantage that the images need not be paired together. For example, in case it is presented with blurred and sharp images (but not paired blurred and sharp images) it will be able to sharpen the blurred images. This is why its other application is preferable: healthy and diseased images of the same patient are usually not available, or, in the alternative application, there is a low chance of receiving a training database wherein measurements of the same patient recorded utilising the base collimator and a different one are included (cf. the description related to FIG. 8).

Thus, to sum up what has been set forth about the auxiliary unit, it can be said that various ways of generating pseudo images, i.e. of synthesising abnormal accumulations into the images have been presented; i.e., in a direct manner in FIGS. 3A-3B and in FIGS. 17A-17F, and analogously in FIG. 16 and on a related note, also in a cyclical system, in FIG. 8. In addition to the methods described above, other solutions are also available for generating pseudo images, i.e., for synthesising content conforming to the regulations.

In the system according to the invention, the main component IV is the ROC unit, which, also in the present example, is adapted for receiving the lesion layer images originating in the auxiliary unit (an example of which is shown in FIG. 17F). Further, by feeding to the image processing chain a synthetic diseased image that is consistent with the layer image and is also produced by the auxiliary unit and passing it through the image processing component and the annotator, the lesions illustrated in FIG. 15 are found (detected) and classified by the system. They are then compared with the lesion layer image by the ROC unit that can unequivocally identify where the processing-annotation branch has made mistakes. By performing these actions for a larger number (typically hundreds or a few thousand) of synthesised images the real positive recognition rate (sensitivity) and the false positive failure rate (1−specificity) can be obtained.

The above-mentioned study (Julian B. Tilbury et al., *Receiver Operating Characteristic Analysis for Intelligent Medical Systems—A New Approach for Finding Confidence Intervals*, IEEE TRANSACTIONS ON BIOMEDICAL ENGINEERING, VOL. 47, NO. 7, July 2000.) sets forth the mathematically proven approach that specifies how the entire ROC curve—together with its confidence intervals—can be determined on the basis of the failure rates specified above, "measured" by the auxiliary unit utilising synthesised images and correspond to a single point of the ROC curve.

The accurate determination of the ROC curves and the possibility to calculate the confidence intervals allows us—for example in the situation illustrated in FIG. 7—to establish the degree by which the activity injected to the patient can be reduced without significantly affecting the diagnostic value of the system (and more particularly, in the case illustrated by the example, of the filter) applied for aiding evaluation.

A summary in certain aspects is provided below.

The invention preferably has a so-called "quality assurance" aspect, which is a significant and distinguishing character (feature) that is basically provided by the invention with the help of the following features:

By reintroducing (feeding back) information generated by the ROC unit into the training process (see the role played by the AUC parameter in joint training).

With the help of a (preferably GAN-based) emulation branch based on the auxiliary unit, which allows precisely that the ROC curve, and, accordingly, the AUC parameter, can be estimated accurately (this is the branch based on processing and annotating the pseudo images generated by the generator subunit of the auxiliary unit).

By the entire construction, i.e., by the assembly formed by the feedback of the AUC parameter calculated from the ROC curve and the (for example, GAN-based) emulation branch based on the auxiliary unit, and also by the preferably applied methods described above directed at improving robustness (on further features see the description of FIGS. 7-10) that allow for:

continuously testing the quality/efficacy of the system, and, if it is found that for example due to changes in the local population (i.e., that on what kind of population the system is applied), due to replacing the camera collimator, or due to a modified examination protocol the diagnostic value of the image processing system is significantly deteriorated, then applying a suitable intervention, i.e., for example transforming the input by a suitable CycleGAN network (UK, KU transformations), while at the same time, in a highly advantageous manner, avoiding the costly and time-consuming medical re-verification of the system.

In a particularly preferable manner, this allows us to ensure the reliable operation of all systems implementing the invention—for example, deployed in hospitals—even in quickly changing and diverse situations. It is noted here that achieving the reliable operation in conventional ways, by known means and methods would be so costly that would prohibit the commercial application of such systems. This is one of the reasons why systems that have even similar functionality to the invention are essentially not available, because this range of problems is not solved by the known approaches. The concept according to the invention offers an effective solution proposal to these issues.

In other words, thanks to the configuration method the system according to the invention is preferably able to behave in a robust manner in the following cases that all have high practical importance:

collimator replacement;

recalibration of the camera (uniformity, linearity, centre-of-rotation, geometrical calibration);

change of camera type;

different patient examination protocol (injected activity, measurement time);

different patient population.

The system according to the invention is therefore able to assure the clinical (diagnostic) value of the applied image processing component without requiring re-verification (which would be extremely costly), which greatly improves the significance of the invention as presently there are no known similar, cost-effective methods that would be able to provide that.

In relation to the training of the system the following summary can be provided:

there is a system of machine learning modules (neural networks) where each module undergoes individual pre-training;

in addition to that, each individual module (network) has a medically interpretable output (for example, the output of a filter is an image filtered in an edge-retaining manner, and the annotator outputs an image where the accumulations are marked); and the loss functions of the standalone networks applied for processing and annotation also receive the AUC parameter as a complementary parameter applied for post-training the system.

In the following, a delimitation of the invention from the prior art is provided.

In relation to US 2019/0073569 A1 the following observations can be made: The tasks performed by the two networks described in US 2019/0073569 A1 are typically performed in the invention by the preferably applied annotator. That is, according to this document AUC feedback can only affect these tasks. In contrast to that, in the invention, in addition to being applied in the training of the annotator, the AUC parameter also plays a role in training the processing unit in the framework of joint training applied according to the invention. Accordingly, the standalone training of the processing unit and the annotator followed by their joint training cannot be learned from US 2019/0073569 A1.

In addition to that, of course, another major difference compared to US 2019/0073569 A1 in the solution according to the invention lies in the role played by the auxiliary unit in joint training and during operation. Furthermore, the invention can be preferably applied for whole body (see FIGS. 12-15).

Paragraph [0017] of US 2019/0073569 A1 relates to the feedback of the AUC parameter into the loss function of the discussed classification network (giving the probability of differences into malignant and benign classes) in order to correct the instability caused by the imbalanced training dataset.

Although the prior art approach mentioned above estimates an ROC curve, the resulting estimate has a relatively high error rate because whether a difference is malignant or benign can in most cases be safely determined only by a histopathological examination. In this prior art approach, therefore, ROC curves (i.e., true and false positive rates) are estimated without knowing the real, the "truth" (i.e., knowing which lesions are malignant and benign) about the applied examinations (conversely, in the case of the invention the ROC unit receives the abnormal accumulation layer as a "ground truth"). This in turn results in that the ROC/AUC feedback cannot be effective either because it is burdened with significant error.

Thus, the simulation branch based on the auxiliary unit applied in joint training in the invention—that is, joint training performed with the help of pseudo images—removes this latent error from the system, and thereby the AUC feedback is expected to significantly better assist in measuring and preserving the diagnostic value. This is a significant addition and solution path which the invention has compared to the above prior art document.

In US 2018/0286038 A1 the AUC parameter is utilised for training a single module (the classification module); this is because in this prior art approach only a single trainable module is included—in contrast to the present invention, wherein during joint training the AUC parameter is fed back to affect the training of the processing unit and the annotator. Accordingly, in the approach according to US 2018/0286038 A1 the invention's fundamental features—i.e., that the modules to be trained are first trained in a standalone manner and are then undergo joint training—are formally impossible to interpret. Besides that, US 2018/0286038 A1 also does not address the role the auxiliary unit included in the solution according to the invention performs during training and operation.

In the case of the invention, the standalone neural networks being in the processing chain, such as for example the processing unit (e.g., filter) and the annotator included downstream of it (which preferably also has a classification functions) are subjected to pre-training independently of each other. The loss function utilised for pre-training is constructed such that it ensures that the partial networks have outputs that are valuable by themselves (i.e., can be interpreted and examined individually). An example for that is that the filter must generate from a noisy image such an image that is as similar to its low-noise counterpart as possible, and is also medically relevant in the details of the image.

By including, in the case of the invention, the AUC as a diagnostically relevant parameter in the training of certain components (the neural networks thereof) with a given weight, it for example becomes possible that the filter thereby subjected to further training can separate (pick up) from the noise the changes different from normal and thus support the early recognition of disease. To summarise, an important component of our invention is independent pre-training followed by post-training (joint training); these are not included in the above-mentioned prior art document.

Paragraph [0077] of US 2018/0286038 A1 discloses an approach wherein the AUC information is fed back to a given decision making layer of the deep network (see the decision-making layer 138 in FIG. 5 of the document). With regard to this aspect, the difference with respect to this aspect is that in the invention the networks are standalone ones (that is, they are pre-trained separately, and they also retain their own functionalities during joint training and during the use of the system), so they possess their own interpretable intermediate outputs that can be medically evaluated and verified, i.e., in the invention the AUC parameter is not fed back to an internal representation of a deep network (where, as in the prior art approach, its effects are untraceable).

In paragraph [0078] of the document it is mentioned that the AUC parameter feedback applied according to the document results in an unfavourable gradient behaviour, i.e., noise is introduced into the multi-variable non-linear hypersurface representing the training process, as a results of which it is necessary for them to apply a genetic algorithm. Genetic algorithms run extremely slowly, i.e., their search for a local optimum is so slow that it essentially makes it impossible to perform the training process. Accordingly, the requirement of utilising a genetic algorithm in the prior art approach has a disadvantage.

Conversely, in the case of the invention, thanks also to pre-training and to the well controllable intermediate outputs, the total training process based on these features—and also applying joint training—is significantly faster and is rendered more stable, i.e., it is not necessary to apply genetic algorithms.

In case of the invention, the feedback of ROC information—i.e., of the AUC parameter obtained by the ROC unit—is applied not only to the last element of the processing chain, but also to the processing unit (e.g., filter network), as a result of which it is able to change in such a way that it enhances clinically relevant information.

In the case of the invention, furthermore, ROC-based joint training is based on the auxiliary unit (for example, a GAN network), which is a principal element of the inventive idea, and ensures the operational robustness of the system even for image sets that are slightly different from earlier trainings. This aspect is not even touched upon in the prior art document cited above (as it was mentioned above, joint training cannot be derived from it), and accordingly the idea spelled out therein significantly differs from the inventive concept.

The aspects set forth in paragraph [0077] of US 2018/0286038 A1 that were already analysed above in relation to the inventive concept will now be examined in light of the example that was described in detail above.

As we spelled out in the description of the example of the image processing component, as a result of joint training, the behaviour of the filter changes, i.e., it is less prone to remove from the filtered/synthesised image the real, different from normal accumulations, and it does not place onto it false positive accumulations, in spite of the fact that based on the local noise structure of the noise input image such accumulations are probable.

In this context, therefore, feeding back the ROC information (AUC parameter) in case of the invention—i.e., embedding feedback of the ROC information into the disclosed system, as it was presented in the examples described in detail—ensures that information relevant for medical diagnosis is not lost during the image processing step, the network does not generate "into the noise" such false information that could result in an erroneous diagnosis, as well as the rate of these is set to the lowest possible.

The approach applied according to the invention is completely different from the one described paragraph [0077] of the prior art document analysed above, where feeding back the ROC information is mentioned. On the one hand, the key components presented here (annotator, auxiliary unit) are absent there, and on the other hand there, as it was mentioned above, the reintroduction of the ROC information into one of the processing layers of the deep neural network encodes this additional information in an abstract way. In contrast to that, in the case of the invention, as it is illustrated also in FIGS. 11A-11F, 12, and 13, preferably every step has a result that is visually valuable (has diagnostic relevance) and can be verified medically, in connection with the manner of standalone training and joint training applied in the invention.

Furthermore, according to the invention each subsystem (processing, annotator and auxiliary units) is trained separately (pre-training) before the joint training, which is a very important technical step because it ensures that the network can achieve significantly higher accuracy and also—based on the ROC curve—significantly higher AUC values (i.e., it has a very pronounced advantageous effect) compared with the case where this pre-training step and the possibility of the separate visual evaluation of each constituent network would be omitted.

This is therefore a particularly important advantage of the invention with respect to the genetic algorithm described in paragraph and constitutes an essential difference (the decision to apply a genetic algorithm indicates precisely that an appropriate stable solution has not been found). At the same time, this solution, preferably applied by the invention, also supports the adjustment of the topological parameters of deep networks—in the example described in detail, U-NET—i.e., for example, the number of layers or the depth parameter of U-NET, in such a manner that the network is really optimal for the specific tasks.

In relation to US 2020/0175397 A1 the following observations can be made. The manner of estimating the ROC curve applied for evaluating the quality of the system according to this prior art approach is described in paragraphs [0025] and [0035] of the document. In paragraph it is indicated that the fall of the AUC parameter below a certain threshold indicates that the system no longer complies with the requirements; in such a case the system parameters are re-optimised. In addition to the differences set forth below, the prior art approach is also different from the invention in these aspects.

In relation to US 2020/0175397 A1 we also emphasise that the prior art approach involves improving the accuracy of a classifier applying among others information obtained on the basis of the ROC curve. However, the method according to the invention preferably involves a system of neural networks and also includes training of an annotator and a first processing step, for example image filtering, the operation of which is also affected by the ROC analysis applied according to the invention.

On the other hand, it is also important to emphasise that in the case of the invention the performance of the neural network system is preferably controlled by a GAN-based portion (generally: the auxiliary unit and the discriminator subunit thereof) into which we feed a significant portion of the medical knowledge (see for example FIGS. 3A-3B). This allows the preservation of diagnostic value even if, for example, medical images that are very different from the training database of the network have to be examined, for example because certain characteristics of the image recording apparatus applied for generating the medical image have been modified (see above in relation to FIG. 8). This solution, resulting in a robust operation, is preferably also applied in the invention beside the approach based on ROC analysis. It is important to emphasise therefore that in the case of the invention the ROC analysis is not merely an indication means as in the prior art approach cited above, i.e., it has a much greater role.

As it was set forth in relation to the example described in detail above, the ROC unit working on the layer image generated by the auxiliary unit (assistant unit) and on the image processed from the synthesised image input to the image processing chain (i.e., in the example, the filter and the annotator) generates the ROC curve, the integral thereof (AUC), and their confidence intervals.

In US 2019/0073569 A1 the ROC information is applied only for verification, while in the case of the invention the information obtained according to the above is incorporated into the joint training (see the exemplary manner shown in FIG. 15), thereby modifying the operation of the filter (image filter) and the annotator. Accordingly, there are preferably such suspected lesion locations that for example will already not be marked by the annotator as suspected, different from normal accumulations but would otherwise be marked as such.

The GAN system disclosed in WO 2019/241155 A1 first applies healthy tissue structures for segmenting the region of interest, and then replaces these with abnormal regions, which can be seen in disease showing images. The stated field of application of the GAN thus produced are those situations wherein due to certain rare pathologies the training image database is unbalanced. In such cases, the discrimination accuracy of the classification networks can be significantly improved for example by complementing the rare pathologies by images comprising simulated abnormalities. It is noted that the GAN synthesising abnormal differences and the layer images thereof that is featured in the inventive idea is only a preferable means for testing the clinical value of our processing and classification (annotator) machine learning units, and for reintroducing the results to the system (such an aspect is not disclosed by the prior art approaches).

WO 2019/241155 A1 discloses GAN systems adapted for placing abnormal regions, lesions, or for example cardiac muscle differences onto healthy patient images (see also below for a discussion of this document). In US 2020/0134446 A1 a local evaluator compares the performance of a DNN trained on local scans and a DNN' trained on synthesised images generated by the GAN.

Further GAN applications are disclosed in CN 110580695 A, CN 110808095 A, US 2019/0369191 A1, US 2020/0265318 A1, WO 2018/232388 A1, and WO 2019/238804 A1. CycleGAN applications are disclosed in US 2019/0205334 A1, US 2019/0333219 A1 and US 2019/0392580 A1. Still further GAN-based approaches directed fundamentally at image correction are disclosed in EP 3447721 A1, US 2019/0164288 A1, U.S. Pat. No. 10,387,765 B2, US 2020/0034948 A1, and WO 2019/147767 A1.

The above GAN-based systems have not been applied in a manner similar to the invention, i.e., in a joint training system utilising pseudo images generated by a preferably GAN-based module, passing the images through the units involved in the training method (processing unit, annotator) such that they can be applied for calculating an AUC parameter and that the joint training can be performed while preserving diagnostic value. In other words, in the above-mentioned approaches the GAN is not included in such applications wherein it would be involved in the training process like in the invention.

It is added that in the other documents disclosing other GAN and CycleGAN solutions listed above and recently the GAN and CycleGAN frameworks are applied as means adapted for performing significantly different tasks than in the invention, i.e., for example for direct image reconstruction.

According to the invention, the GAN is preferably applied for generating synthetic data (pseudo images) that are utilised for measuring the performance of the given machine learning module (for example, neural network), in our case a noise filter and an annotator. However, in relation to GAN our inventive idea basically concerns reintroducing (feeding back) the relevant measures (ROC/AUC) of the GAN system's performance into the training process. It can be ensured precisely by this that the trained or trans-trained (see FIG. 8) neural networks remain valuable from a medical point of view. Such an aspect is not addressed in the prior art approaches.

In the case of the invention, furthermore, GAN training applies not only the images available at a particular venue (location; in contrast to for example US 2020/0134446 A1) but an annotated image database specially annotated by physicians, so in the case of the invention a significant portion of medical expertise is introduced into the GAN. Our inventive idea preferably has the important feature that it "injects" medical expertise into the neural networks of the system in this special manner, allowing us to ensure in a cost-effective way that the trans-trained network in case of changes of the training database remain medically verified furthermore (see FIG. 8).

The invention is, of course, not limited to the preferred embodiments described in detail above, but further variants, modifications and developments are possible within the scope of protection determined by the claims.

The invention claimed is:

1. A training method for training a system adapted for aiding evaluation of an input medical image, wherein the system comprises a processing unit based on machine learning, adapted for generating a processed image from an input medical image, and an auxiliary unit having a discriminator subunit based on machine learning, adapted for determining a discriminability result by subjecting the input medical image to a discriminability test, and, in the course of the training method, applying such an auxiliary unit which has a generator subunit based on machine learning, adapted for generating auxiliary pseudo images and first lesion location data packets corresponding to each, respectively, and determining location of one or more lesion possibly present in the respective auxiliary pseudo images, and applying, furthermore, an annotator unit based on machine learning, adapted for identifying a lesion and for generating an annotation result dataset comprising a second lesion location data packet determining location of the one or more lesion possibly identified, and a ROC unit adapted for determining an AUC parameter characteristic of a diagnostic value, the training method comprising the following steps:

training in a pre-training step the processing unit applying processing unit pre-training, the annotator unit applying annotator unit pre-training, and the discriminator subunit and generator subunit of the auxiliary unit applying auxiliary unit pre-training, wherein the processing unit pre-training, the annotator unit pre-training, and the auxiliary unit pre-training are independent of each other, in a first cycle of joint training after the pre-training step, for respective joint-training auxiliary pseudo images generated by the generator subunit of the auxiliary unit trained applying auxiliary unit pre-training, by transferring to the ROC unit a second lesion location data packet determined by successive application of the processing unit and the annotator unit, and a respective first lesion location data packet corresponding to each joint-training auxiliary pseudo image, determining a value of the AUC parameter by means of the ROC unit for the joint-training auxiliary pseudo images based on a comparison of the first lesion location data packet and the second lesion location data packet generated for each of the joint-training auxiliary pseudo images, and in at least one further cycle of the joint training performing training of the processing unit and of the annotator unit applying a value of the AUC parameter determined in the previous cycle in a respective AUC parameter dependent term of a processing unit joint-training loss function of the processing unit and of an annotator unit joint-training loss function of the annotator unit, and then, by transferring to the ROC unit for the joint-training auxiliary pseudo images a respective second lesion location data packet determined by the successive application of the processing unit and the annotator unit, and a respective first lesion location data packet corresponding to each of the joint-training auxiliary pseudo images, determining a value of the AUC parameter.

2. The training method according to claim 1, characterised in that for determining the second lesion location data packet, a search step is performed by means of the annotator unit on a joint-training processed image obtained by means of the processing unit from the joint-training auxiliary pseudo image, for determining location of a lesion candidate, and in case a lesion candidate is found on the joint-training processed image in the search step, classifying each of the one or more lesion candidate identified as lesion either into a first annotation group of safely identifiable lesion or into a second annotation group of uncertainly identifiable lesion, or classifying into a third annotation group of lesion candidate different from a lesion, and if there is a lesion classified into the first annotation group and/or into the second annotation group, then only location of one or more lesion classified into the first annotation group and into the second annotation group are determined in the second lesion location data packet.

3. The training method according to claim 2, characterised by in the first lesion location data packet respective intensity data are assigned to each of the one or more lesion possibly present, assigning respective classification information to each of the one or more lesion possibly classified into the first annotation group and into the second annotation group, and incorporating the classification information into the second lesion location data packet, and taking into consideration by the ROC unit, in the course of the comparison, for the one or more lesion possibly present in the first lesion location data packet and in the second lesion location data packet, the intensity data and the classification information, respectively.

4. The training method according to claim 1, characterised in that, in the course of the auxiliary unit pre-training, training of the generator subunit and the discriminator subunit of the auxiliary unit is performed by means of a generator subunit pre-training loss function and a discriminator subunit pre-training loss function corresponding to the training, respectively, after performing the following steps multiple times:

generating first auxiliary pre-training pseudo images by means of the generator subunit based on a noise input by the help of healthy medical training images, by means of the discriminator subunit inputting out of first auxiliary pre-training pseudo images or abnormal medical training images, performing a discriminability test determining a discriminability result, then, by investigating correctness of the discriminability result, determining an evaluation result about it, and applying in the generator subunit pre-training loss function and in the discriminator subunit pre-training loss function a term being dependent on the evaluation result.

5. The training method according to claim 1, characterised by applying for a system which comprises an auxiliary unit which has a discriminator subunit configured by a first assistant discriminator subunit and a second assistant discriminator subunit, and in the course of the auxiliary unit pre-training, training of the generator subunit, the first assistant discriminator subunit and the second assistant discriminator subunit of the auxiliary unit is performed by means of a generator subunit pre-training loss function, as well as a first assistant discriminator subunit pre-training loss function and a second assistant discriminator subunit pre-training loss function corresponding to the training, respectively, after performing the following steps multiple times:

generating second auxiliary pre-training pseudo images and auxiliary pre-training lesion images determined by a first lesion location data packet corresponding thereto by means of the generator subunit based on a noise input, by means of the first assistant discriminator subunit inputting out of the second auxiliary pre-training pseudo images or abnormal medical training images, performing a discriminability test determining a first discriminability result, and by means of the second assistant discriminator subunit inputting differences generated by subtracting from the second auxiliary pre-training pseudo images the corresponding respective auxiliary pre-training lesion images, or inputting healthy medical training images, performing a discriminability test determining a second discriminability result, then, by investigating correctness of the first discriminability result and of the second discriminability result, determining a first evaluation result and second evaluation result about them, respectively, and, applying in the generator subunit pre-training loss function respective terms being dependent on the first evaluation result and on the second evaluation result, and applying in the first assistant discriminator subunit pre-training loss function a term being dependent on the first evaluation result, and applying in the second assistant discriminator subunit pre-training loss function a term being dependent on the second evaluation result.

6. The training method according to claim 1, characterised by applying, as a processing unit, a filter unit-transforming the input medical image into a lowered-noise filtered processed image.

7. The training method according to claim 6, characterised in that in the course of a filter unit pre-training performed as processing unit pre-training, training of the filter unit is performed by means of the filter unit pre-training loss function corresponding to the training, after performing the following steps multiple times:

by means of the filter unit generating a lowered-noise filtered pre-training image based on a higher-noise training image, generating a first difference result by comparing the filtered pre-training image and the lower-noise training image corresponding to the higher-noise training image, and applying in the filter unit pre-training loss function a term being dependent on the first difference result.

8. The training method according to claim 1, characterised in that in the course of the annotator unit pre-training, training of the annotator unit is performed by means of an annotator unit pre-training loss function corresponding to the training, after performing the following steps multiple times:

by means of the annotator unit generating an annotated pre-training image based on an annotation input training image, generating a second difference result by comparing the annotated pre-training image and an annotated training image corresponding to the annotation input training image, and applying in the annotator unit pre-training loss function a term being dependent on the second difference result.

9. The training method according to claim 1, characterised in that after the joint training, in course of a reduction proportion checking, for one or more parameter values of a reduction parameter being greater than one, generating reduced signal-to-noise ratio images by subsampling checking auxiliary pseudo images generated by means of the auxiliary unit by parameter values of the reduction parameter, by transferring to the ROC unit second lesion location data packets determined by the successive application of the processing unit and the annotator unit on the reduced signal-to-noise ratio images, and also respective first lesion location data packets corresponding to each of the checking auxiliary pseudo images, determining a value of the AUC parameter corresponding to the parameter value of the reduction parameter, based on the values of the AUC parameter corresponding to the respective reduction parameter values, a highest value being diagnostically safe is determined from among the one or more parameter values of the reduction parameter.

10. The training method according to claim 9, characterised in that the reduction proportion checking is carried out applying parameter values of the reduction parameter between two and one hundred.

11. The training method according to claim 10, characterised in that the reduction proportion checking is carried out applying the first, second, and third powers of two as the parameter values of the reduction parameter.

12. A system for aiding evaluation of an input medical image, the system is trained by means of the training method according to claim 1 and comprises the processing unit and the auxiliary unit having the discriminator subunit.

13. The system according to claim 12, characterised by comprising the annotator unit.

14. The system according to claim 13, characterised by comprising the ROC unit.

15. The system according to claim 14, characterised in that the discriminator subunit is adapted for issuing a discriminability warning in the case of a discriminability result corresponding to discriminability.

16. A configuration method for configuring the system according to claim 15 in case of issuing a discriminability warning, wherein, by collecting a plurality of discriminability warnings, applying a plurality of input medical images before issuing the first one of the discriminability warnings as first type input medical images and a plurality of further input medical images having discriminability warnings as second type input medical images, in the course of the method training, in a transformation-training step, a first transformation unit adapted for transforming the respective first type input medical images, applying configuration training with the help of the plurality of first type input medical images and the plurality of second type input medical images, and training a second transformation unit adapted for transforming the respective second type input medical images, wherein a transformation carried out by means of the first transformation unit is adapted for eliminating discriminability of the first type input medical image from the second type images, and a transformation carried out with the second transformation unit is adapted for eliminating discriminability of the second type input medical image from the first type images, in a first diagnostic value verification step, performing steps of the joint training on joint-training auxiliary pseudo images originating from the auxiliary unit such that the joint-training auxiliary pseudo images are transferred to the processing unit being subjected the first transformation unit to them, and, for each of the joint-training auxiliary pseudo images a second lesion location data packet determined by the successive application of the processing unit and the annotator unit, and a respective first lesion location data packet corresponding to each of the joint-training auxiliary pseudo images are transferred to the ROC unit, and by determining the AUC parameter by means of the ROC unit, checking preservation of the diagnostic value, wherein in case preservation of the diagnostic value can be established, a signal related to unchanged further usability of the system is issued, or, in case preservation of the diagnostic value cannot be established, then in a second diagnostic value verification step, the steps of the joint training are performed on the joint-training auxiliary pseudo images originating from the auxiliary unit such that the joint-training auxiliary pseudo images are transferred to the processing unit subjecting the first transformation unit and the second transformation unit successively to them, and, for each of the joint-training auxiliary pseudo images a second lesion location data packet determined by the successive application of the processing unit and the annotator unit, and a respective first lesion location data packet corresponding to each of the joint-training auxiliary pseudo images are transferred to the ROC unit, and by determining the AUC parameter by means of the ROC unit, checking preservation of the diagnostic value, wherein in case preservation of the diagnostic value can be established, then the system is configured by including the second transformation unit upstream of the processing unit for transforming the input medical image for the processing unit, or in case preservation of the diagnostic value cannot be established, then a newly training warning indicating necessity of newly training the system is issued.

* * * * *